US012807718B2

(12) United States Patent
Liu et al.

(10) Patent No.: US 12,807,718 B2

(45) Date of Patent: Nov. 24, 2026

(54) ANTI-ADENOSINE RECEPTOR (A2AR) ANTIBODIES

(71) Applicants: NA Biotech Corp, Worcester, MA (US); Adept Biopharmaceutical and Technology, Ltd., Shenzhen (CN)

(72) Inventors: Shuying Liu, Hopkinton, MA (US); Xinyan Zhao, Bedford, MA (US); Changyun Hu, Belmont, MA (US)

(73) Assignees: Adept Therapeutics Inc., Bedford, MA (US); Adept Biopharmaceutical and Technology, Ltd., Shenzhen (CN)

( * ) Notice: Subject to any disclaimer, the term of this patent is extended or adjusted under 35 U.S.C. 154(b) by 682 days.

(21) Appl. No.: 18/028,917

(22) PCT Filed: Sep. 30, 2021

(86) PCT No.: PCT/US2021/052819

§ 371 (c)(1),
(2) Date: Mar. 28, 2023

(87) PCT Pub. No.: WO2022/072601

PCT Pub. Date: Apr. 7, 2022

(65) Prior Publication Data

US 2023/0340132 A1 Oct. 26, 2023

Related U.S. Application Data

(60) Provisional application No. 63/085,612, filed on Sep. 30, 2020.

(51) Int. Cl.

| | |
|---|---|
| ***C07K 16/28*** | (2006.01) |
| ***A61P 35/00*** | (2006.01) |
| ***C12N 15/63*** | (2006.01) |

(52) U.S. Cl.

CPC ............ *C07K 16/286* (2013.01); *A61P 35/00* (2018.01); *C12N 15/63* (2013.01); *C07K 2317/24* (2013.01); *C07K 2317/565* (2013.01)

(58) Field of Classification Search

None

See application file for complete search history.

(56) References Cited

U.S. PATENT DOCUMENTS

| | | | | |
|---|---|---|---|---|
| 7,943,743 B2 * | 5/2011 | Korman | .................. | A61P 31/18 530/388.15 |
| 9,212,224 B2 * | 12/2015 | Cogswell | ........... | C07K 16/2803 |
| 2014/0322236 A1 | 10/2014 | Chambers et al. | | |
| 2019/0202912 A1 | 7/2019 | Liu et al. | | |

FOREIGN PATENT DOCUMENTS

| | | | | |
|---|---|---|---|---|
| JP | 2011-97869 A | 5/2011 | | |
| WO | 2013/040358 A2 | 3/2013 | | |
| WO | WO-2019062642 A1 * | 4/2019 | ........... | G01N 33/575 |
| WO | WO-2020185739 A1 * | 9/2020 | .............. | A61P 35/00 |

OTHER PUBLICATIONS

Mittal et al. Cancer Research. 74(14): 3652-3658; Published: Jul. 15, 2014 (Year: 2014).*

Leone et al. Computational and Structural Biotechnology Journal. 13: 265-272; Published: Apr. 8, 2015 (Year: 2015).*

Hanahan et al. Cell. 144(5): 646-674; Published: Mar. 4, 2011 (Year: 2011).*

Pitot et al. Cancer. 73(3): 962-970; Published: Aug. 1, 1993 (Year: 1993).*

GenBank Accession No. AAX90222, immunoglobulin heavy chain, partial [Mus musculus]. 2 pages, Jul. 26, 2016.

GenBank Accession No. ORZ06894, alpha/beta hydrolase fold-domain-containing protein [Absidia repens]. 2 pages, Apr. 20, 2017.

International Search Report and Written Opinion for Application No. PCT/US2021/052819, dated Feb. 3, 2022, 12 pages.

Hu et al., A Novel Antagonist Monoclonal Antibody Against Human Adenosine Receptor 2A (A2AR) for Cancer Immunotherapies. J Immunother Cancer. 2023;11(Suppl 1):A537, Abstract 478.

Hu et al., Potent and Selective A2AR Monoclonal Antibody Antagonist for the Treatment of Cancer. Poster Abstracts of the 2023 Chinese Antibody Society Annual Conference. Jul. 24, 2023;6(Suppl 1):15, Abstract tbad014010.

Wang et al., Discovery of a potent, selective, and tumor-suppressing antibody antagonist of adenosine A2A receptor. PLoS One. Jun. 5, 2024;19(6):e0301223, 13 pages.

Willingham et al., Targeting the A2AR in cancer; early lessons from the clinic. Curr Opin Pharmacol. Aug. 2020;53:126-133.

* cited by examiner

*Primary Examiner* — Gregory S Emch

*Assistant Examiner* — Katherine Ann Holtzman

(74) *Attorney, Agent, or Firm* — McCarter & English, LLP; Marcie B. Clarke

(57) ABSTRACT

The present invention provides anti-A2aR antigen binding molecules, including antibodies and the antigen binding fragment thereof, and methods for using the same for treating a variety of diseases associated with aberrant adenosine signaling, including cancers, chronic diseases, chronic infections, autoimmune diseases, inflammatory diseases, neurodegenerative diseases, and fibrotic diseases.

20 Claims, 7 Drawing Sheets

Specification includes a Sequence Listing.

ANTI-ADENOSINE RECEPTOR (A2AR) ANTIBODIES

RELATED APPLICATIONS

This application is a 35 U.S.C. § 371 national stage filing of International Application No. PCT/US2021/052819, filed on Sep. 30, 2021, which claims priority of U.S. Provisional Application No. 63/085,612, filed on Sep. 30, 2020. The entire contents of each of the aforementioned applications are expressly incorporated herein by reference in their entirety as part of the disclosure of the present application.

SEQUENCE LISTING

The instant application contains a Sequence Listing which has been submitted electronically in ASCII format and is hereby incorporated by reference in its entirety. Said ASCII copy, created on Mar. 28, 2023, is named 136546-00101_SL.txt and is 30,632 bytes in size.

FIELDS

The present invention relates to antibodies for cancer treatment and, in particular, to adenosine receptor A2aR antibodies for cancer immunotherapy.

BACKGROUND

The immune system plays an important role in the identification and elimination of neoplastic cells. Tumor cells use various mechanisms for evading the immune-mediated destruction of tumor cells. Among those pathways, tumor cells exploit adenosine signaling pathways to circumvent immune defenses by increasing adenosine levels and responsiveness to adenosine, a highly effective inhibitor of effector T cell function.

Adenosine is a purine nucleoside, resulting from the degradation of adenosine triphosphate (ATP). Under adverse conditions, including hypoxia, ischemia, inflammation, or cancer, the extracellular levels of adenosine increase significantly. Once released, adenosine activates cellular signaling pathways through the engagement of the four known G-protein-coupled receptors, adenosine A1 receptor subtype (A1R), adenosine A2A receptor subtype (A2aR), adenosine A2B receptor subtype (A2bR) and adenosine A3 receptor subtype (A3R).

Adenosine levels are largely controlled by the activities of CD39 and CD73. CD39 and CD73 are two ecto-enzymes that work together in a two-step reaction to convert pro-inflammatory ATP into immunosuppressive adenosine. CD39 hydrolyzes ATP into AMP, which is further hydrolyzed by CD73 into adenosine, which can readily enter most cells. Further, as tumor cells undergo cell death as a result of metabolic or hypoxic stress, they release intracellular stores of ATP (to which cells are generally impermeable) into the extracellular space.

Within the tumor microenvironment, adenosine produced by CD73 promotes tumor cell growth and survival, while suppressing antitumor immune responses. Cancer cells exhibit high levels of CD73 expression in tumor tissue and their accumulation has been linked to poor overall survival and poor recurrence-free survival in patients suffering from breast and ovarian cancer. CD73 and adenosine support growth-promoting neovascularization, metastasis, and survival in cancer cells. Adenosine binds A2A (or A2A) receptors (A2aRs) on T cells and activates an intracellular signaling cascade leading to the suppression of T cell activation and function. A2aR is a member of the adenosine receptor group of G-protein-coupled receptors that also includes A1R, A2bR and A3R, and is an anti-inflammatory effector of extracellular adenosine through its predominant expression on the cells in the brain and lymphoid tissues.

The presence of adenosine at abnormally high concentrations in the immune microenvironment leads to the activation of A2aR and represents a negative feedback loop by which tumors can evade immune recognition. In particular, adenosine-mediated activation of A2aR enables tumors to escape immune surveillance by inhibiting IFNγ production, and suppressing the activity of multiple anti-tumor immune cells, including $CD8^{+}$T cells, dendritic cells, natural killer cells, and M1 macrophages, while enhancing the activity of immunosuppressive cell types, including myeloid-derived suppressor cells (MDSCs) and T-regulatory ($T_{reg}$) cells. Activation of A2aRs on tumor cells has also been suggested to promote tumor cell metastasis.

While several A2A receptor small molecule antagonists have progressed to clinical trials for the treatment of Parkinson's disease and cancers, A2aR blockade by biologics drug candidate in the context of cancer therapy is still lacking. Mice treated with A2aR antagonists, such as ZM241385, showed significant delay in tumor growth due to reduced immunosuppression on effector T cells. This was further highlighted by A2aR knockout mice that showed increased tumor rejection. Furthermore, A2aR blockade by small molecule antagonist was shown to have synergistic effect on increasing immune response when combined with PD-1/PD-L1 or CTLA-4 inhibition with monoclonal antibodies as compared to the blockade of a single PD-1/PD-L1 or CTLA-4 pathway alone.

Consequently, modulating A2aR activity, adenosine concentration, and/or CD39/CD73 expression and activation of effector immune cells in the tumor microenvironment presents as an attractive therapeutic strategy to limit tumor progression, improve antitumor immune responses, avoid therapy-induced immune deviation, and potentially limit normal tissue toxicity. There is a need in the art for compositions and methods that treat a cancer by modulating, e.g., inhibiting, A2aR activity of an immune cell.

SUMMARY

The present invention provides antigen binding molecules, e.g., anti-A2aR antibodies or antigen binding fragments thereof, for modulating the activity (e.g., enhancing or inhibiting the activity) of A2aR by specifically binding to an A2aR. The A2aR may be on the surface of a cell, e.g., a mammalian cell, such as an immune cell of a mammal, e.g., a mouse immune cell, a cynomolgus immune cell or a human immune cell. The present invention also provides methods of using the antigen binding molecules, e.g., anti-A2aR antibodies or antigen binding fragments thereof of the invention, for modulating, e.g., inhibiting, the activity of an A2aR or for treating a subject who would benefit from modulating, e.g., inhibiting, the activity of an A2aR, e.g., a subject suffering or prone to suffering from an A2aR-associated disease.

Accordingly, in one aspect, the present invention provides an isolated antigen binding molecule, e.g., an antibody or antigen-binding fragment thereof, that binds to human adenosine A2A receptor (A2aR). The antibody includes a heavy chain variable (VH) domain comprising from N-terminus to C-terminus, three heavy chain complementarity-determining regions (CDRs), HCDR1, HCDR2, and HCDR3; and a light chain variable (VL) domain comprising from N-terminus to C-terminus, three light chain complementarity-determining regions (CDRs), LCDR1, LCDR2, and LCDR3; wherein (a) the HCDR1 comprises an amino acid sequence $X_1$-$X_2$-W-M-N(SEQ ID NO: 8), wherein $X_1$ is S or R, and $X_2$ is Y or F; (b) the HCDR2 comprises an amino acid sequence R-I-D-P-$X_3$-D-S-E-$X_4$-$X_5$-Y-$X_6$-H-K-F-W-$X_7$ (SEQ ID NO: 9), wherein $X_3$ is S or Y, $X_4$ is A or T, $X_5$ is H or Q, $X_6$ is H or N, and $X_7$ is D or G; (c) the HCDR3 comprises an amino acid sequence SLYGKGDY (SEQ ID NO: 3); (d) the LCDR1 comprises an amino acid sequence R-S-S-Q-S-$X_{17}$-V-H-$X_{18}$-N-G-N-T-Y-L-E (SEQ ID NO: 30), wherein $X_{17}$ is L or I, $X_{18}$ is R or S; (e) the LCDR2 comprises an amino acid sequence K-V-S-N-R-F-S(SEQ ID NO: 26); and (f) the LCDR3 comprises an amino acid sequence $X_{19}$-Q-G-S-H-V-P-L-T (SEQ ID NO: 31), wherein $X_{19}$ is Y or F.

In various aspects of the invention and embodiments thereof, the antibody is an antigen binding fragment of the antibody. In various aspects of the invention and embodiments thereof, the human A2aR comprises a sequence as set forth in SEQ ID NO: 50.

In one embodiment, (a) the HCDR1 comprises an amino acid sequence selected from the group consisting of SEQ ID NOs: 1, 4, and 6; (b) the HCDR2 comprises an amino acid sequence selected from the group consisting of SEQ ID NOs: 2, 5, and 7; (c) the HCDR3 comprises an amino acid sequence as set forth in SEQ ID NO: 3; (d) the LCDR1 comprises an amino acid sequence as set forth in SEQ ID NO: 25 or 28; (e) the LCDR2 comprises an amino acid sequence as set forth in SEQ ID NO: 26; and (f) the LCDR3 comprises an amino acid sequence as set forth in SEQ ID NO: 27 or 29.

In another embodiment, the isolated antigen binding molecule, e.g., the antibody, includes (a) the HCDR1 comprising an amino acid sequence set forth in SEQ ID NO: 1, the HCDR2 comprising an amino acid sequence set forth in SEQ ID NO: 2, the HCDR3 comprising an amino acid sequence set forth in SEQ ID NO: 3, the LCDR1 comprising an amino acid sequence set forth in SEQ ID NO: 25, the LCDR2 comprising an amino acid sequence set forth in SEQ ID NO: 26, and the LCDR3 comprising an amino acid sequence set forth in SEQ ID NO: 27; (b) the HCDR1 comprising an amino acid sequence set forth in SEQ ID NO: 4, the HCDR2 comprising an amino acid sequence set forth in SEQ ID NO: 5, the HCDR3 comprising an amino acid sequence set forth in SEQ ID NO: 3, the LCDR1 comprising an amino acid sequence set forth in SEQ ID NO: 28, the LCDR2 comprising an amino acid sequence set forth in SEQ ID NO: 26, and the LCDR3 comprising an amino acid sequence set forth in SEQ ID NO: 29; or (c) the HCDR1 comprising an amino acid sequence set forth in SEQ ID NO: 6, the HCDR2 comprising an amino acid sequence set forth in SEQ ID NO: 7, the HCDR3 comprising an amino acid sequence set forth in SEQ ID NO: 3, the LCDR1 comprising an amino acid sequence set forth in SEQ ID NO: 25, the LCDR2 comprising an amino acid sequence set forth in SEQ ID NO: 26, and the LCDR3 comprising an amino acid sequence set forth in SEQ ID NO: 29.

In still another embodiment, (a) the HCDR1 comprises an amino acid sequence selected from the group consisting of SEQ ID NOs: 21, 22, 23, and 24; and (b) the HCDR3 comprises an amino acid sequence selected from the group consisting of SEQ ID NOs: 12, 15, and 20.

In yet another embodiment, the antigen binding molecule, e.g., the antibody includes (a) a heavy chain variable region (HCVR) comprising an amino acid sequence selected from the group consisting of SEQ ID NOs: 35, 36, 37, 38, 39, and 40; and (b) a light chain variable region (LCVR) comprising an amino acid sequence selected from the group consisting of SEQ ID NOs: 41, 42, and 43.

In one embodiment, the antigen binding molecule, e.g., the antibody, includes: (a) the HCVR comprising an amino acid sequence set forth in SEQ ID NO: 35 or 38, and the LCVR comprising an amino acid sequence set forth in SEQ ID NO: 41; (b) the HCVR comprising an amino acid sequence set forth in SEQ ID NO: 36 or 39, and the LCVR comprising an amino acid sequence set forth in SEQ ID NO: 42; or (c) the HCVR comprising an amino acid sequence set forth in SEQ ID NO: 37 or 40, and the LCVR comprising an amino acid sequence set forth in SEQ ID NO: 43.

In another aspect, the present invention provides an isolated antigen binding molecule, e.g., an antibody that binds to human adenosine A2A receptor (A2aR). The antigen binding molecule, e.g., the antibody includes a heavy chain variable (VH) domain comprising from N-terminus to C-terminus, three heavy chain complementarity-determining regions (CDRs), HCDR1, HCDR2, and HCDR3; and a light chain variable (VL) domain comprising from N-terminus to C-terminus, three light chain complementarity-determining regions (CDRs), LCDR1, LCDR2, and LCDR3; wherein (a) the HCDR1 comprises an amino acid sequence that is about 80%, 85%, 90%, 95%, 96%, 97%, 98%, 99% to about 100% identical to an amino acid sequence selected from the group consisting of SEQ ID NOS: 1, 4, and 6; (b) the HCDR2 comprises an amino acid sequence that is about 80%, 85%, 90%, 95%, 96%, 97%, 98%, 99% to about 100% identical to an amino acid sequence selected from the group consisting of SEQ ID NOS: 2, 5, and 7; (c) the HCDR3 comprises an amino acid sequence that is about 80%, 85%, 90%, 95%, 96%, 97%, 98%, 99% to about 100% identical to an amino acid sequence set forth in SEQ ID NO: 3; (d) the LCDR1 comprises an amino acid sequence that is about 80%, 85%, 90%, 95%, 96%, 97%, 98%, 99% to about 100% identical to an amino acid sequence selected from the group consisting of SEQ ID NOS: 25 and 28; (e) the LCDR2 comprises an amino acid sequence that is about 80%, 85%, 90%, 95%, 96%, 97%, 98%, 99% to about 100% identical to an amino acid sequence set forth in SEQ ID NO: 26, (f) the LCDR3 comprises an amino acid sequence that is about 80%, 85%, 90%, 95%, 96%, 97%, 98%, 99% to about 100% identical to an amino acid sequence selected from the group consisting of SEQ ID NOS: 27 and 29.

In one embodiment, (a) the HCDR1 comprises a sequence comprising 1, or 2 amino acid substitutions from SEQ ID NO: 1, 4, or 6; (b) the HCDR2 comprises a sequence comprising 1, 2, 3, 4 or 5 amino acid substitutions from SEQ ID NO: 2, 5, or 7; (c) the HCDR3 comprises a sequence as set forth in SEQ ID NO: 3 or a sequence comprising 1 or 2 amino acid substitutions from SEQ ID NO: 3; (d) the LCDR1 comprises a sequence comprising 1, 2, 3, or 4 amino acid substitutions from SEQ ID NO: 25 or 28; (e) the LCDR2 comprises a sequence as set forth in SEQ ID NO: 26 or a sequence comprising 1 or 2 amino acid substitutions from SEQ ID NO: 26; and (f) the LCDR3 comprises a sequence comprising 1 or 2 amino acid substitutions from SEQ ID NO: 27 or 29. In another embodiment, the amino acid substitution is a conservative substitution. In another embodiment, (a) the HCDR1 comprises an amino acid substitution at position 1 or 2 of the HCDR1; (b) the HCDR2 comprises an amino acid substitution at position 5, 9, 10, 12 or 17 of the HCDR2; (c) the LCDR 1 comprises an amino acid substitution at position 6, or 9 of the LCDR1; or (d) the LCDR3 comprises and amino acid substitution at position 1 of the LCDR3. In one embodiment, the amino acid substitution is a conservative substitution. In one embodiment, the amino acid substitution is a conservative substitution. In still another embodiment, the HCDR1, HCDR2, HCDR3, LCDR1, LCDR2, and LCDR3 are defined based on Kabat numbering scheme.

In one embodiment, (a) the HCDR1 comprises a sequence comprising 1, 2, or 3 amino acid substitutions from SEQ ID NO: 10, 13, or 16; (b) the HCDR2 comprises a sequence comprising 1, 2, or 3 amino acid substitutions from SEQ ID NO: 11, 14, or 17; (c) the HCDR3 comprises a sequence comprising 1, 2, or 3 amino acid substitutions from SEQ ID NO: 12, or 15; (d) the LCDR1 comprises a sequence comprising 1, 2, 3, or 4 amino acid substitutions from SEQ ID NO: 32, or 33; and (e) the LCDR3 comprises a sequence comprising 1 or 2 amino acid substitutions from SEQ ID NO: 27 or 29. In another embodiment, the amino acid substitution is a conservative substitution. In another embodiment, (a) the HCDR1 comprises an amino acid substitution at position 3, 6, or 7 of the HCDR1; (b) the HCDR2 comprises an amino acid substitution at position 4, or 8 of the HCDR2; (c) the HCDR3 comprises an amino acid substitution at position 1 of the HCDR3 (d) the LCDR1 comprises an amino acid substitution at position 3, or 6 of the LCDR1; or (e) the LCDR3 comprises and amino acid substitution at position 1 of the LCDR3. In one embodiment, the amino acid substitution is a conservative substitution. In still another embodiment, the HCDR1, HCDR2, HCDR3, LCDR1, LCDR2, and LCDR3 are defined based on IMGT numbering scheme.

In still another aspect, the present invention provides an antigen binding molecule, e.g., an antibody. The antibody includes (a) a heavy chain variable region (HCVR) comprising an amino acid sequence that is about 80%, 85%, 90%, 95%, 96%, 97%, 98%, 99% to about 100% identical to an amino acid sequence selected from the group consisting of SEQ ID NOs: 35, 36, and 37; and (b) a light chain variable region (LCVR) comprising an amino acid sequence that is about 80%, 85%, 90%, 95%, 96%, 97%, 98%, 99% to about 100% identical to an amino acid sequence selected from the group consisting of SEQ ID NOs: 41, 42, and 43.

In one embodiment, (a) the HCVR comprises a sequence comprising 1, 2, 3, 4, 5, 6, 7, 8, 9, 10, 11, or 12 amino acid substitutions from SEQ ID NO: 35, 36, and 37; and (b) the LCVR comprises a sequence comprising 1, 2, 3, 4, 5, 6, 7, 8, 9, or 10 amino acid substitutions from SEQ ID NO: 41, 42, and 43. In another embodiment, the amino acid substitution is a conservative substitution.

In one aspect, the present invention provides an antigen binding molecule, e.g., an antibody, that binds human adenosine A2A receptor (A2aR). The antibody includes (a) a heavy chain variable region (HCVR) comprising an amino acid sequence as set forth in SEQ ID NO: 35 or 38; and (b) a light chain variable region (LCVR) comprising an amino acid sequence as set forth in SEQ ID NO: 41.

In another aspect, the present invention provides an antigen binding molecule, e.g., an antibody, that binds human adenosine 2A receptor (human A2aR). The antibody includes a heavy chain variable region (HCVR) comprising an amino acid sequence as set forth in SEQ ID NO: 36 or 39; and (b) a light chain variable region (LCVR) comprising an amino acid sequence as set forth in SEQ ID NO: 42.

In still another aspect, the present invention provides an antigen binding molecule, e.g., an antibody, that binds human adenosine 2A receptor (human A2aR). The antibody includes a heavy chain variable region (HCVR) comprising an amino acid sequence as set forth in SEQ ID NO: 37 or 40; and (b) a light chain variable region (LCVR) comprising an amino acid sequence as set forth in SEQ ID NO: 43.

In one embodiment of various aspects of the invention, the N-terminus of the heavy chain and/or light chain of the antigen binding molecule, e.g., the antibody, is a pyroglutamate (pE) residue.

In another embodiment, (i) the antibody competes for binding to human A2aR with a monoclonal antibody selected from the group consisting of 1B5-3D7, 3F6-9G5, and 3F8-12E9; (ii) the antibody inhibits the activities of A2aR; (iii) the antibody enhances an immune response; (iv) the antibody specifically binds to a cell surface human A2aR; or (v) the antibody reduces cAMP concentration in a tissue; (vi) the antibody reduces protein kinase A activity; (vii) the antibody reduces the phosphorylation of the cAMP response elements of A2aR signal pathway; or (viii) any combination of (i)-(vii).

In one embodiment, the binding of the antibody to an A2aR, or a cell surface A2aR, is determined using flow cytometry-based assays as described in Example 5, 6, and 7, or substantial similar assays thereof. In another embodiment, the competition for binding to an A2aR or a cell surface A2aR by the antibody is determined using an assay known in the art such as the assay described in Harms, et al., Microtiter plate-based antibody-competition assay to determine binding affinities and plasma/blood stability of CXCR4 ligands, Scientific Reports, 2020:10:16036, doi.org/10.1038/s41598-020-73012-4, or substantial similar assay thereof. In still another embodiment, the inhibition of the activities of A2aR is determined using an assay as described in Example 4, or substantially similar assay thereof. In yet another embodiment, reduction of cAMP concentration is determined using an assay as described in Example 4, or substantially similar assay thereof. In one embodiment, the reduction in the protein kinase A activity and/or the reduction in the phosphorylation of the cAMP response elements of A2aR signal pathway is determined using a method described in Karege et al., A non-radioactive assay for the cAMP-dependent protein kinase activity in rat brain homogenates and age-related changes in hippocampus and cortex, Brain Res., 2001 Jun. 8; 903(1-2):86-93, doi: 10.1016/s0006-8993(01)02409-x, or substantially similar assay thereof. In another embodiment, the enhancement of an immune response is determined using methods well known in the art, such as the increase of concentration of inflammatory cytokines in a tissue, increase in the number of cytotoxic CD8+ T cells.

In one embodiment, the antibody inhibits, e.g., reduces, the activities of A2aR by at least about 10%, about 20%, about 30%, about 40%, about 50%, about 60%, about 70%, about 80%, about 90%, about 95%, or about 100%. In another embodiment, the antibody enhances an immune response by at least about 10%, about 20%, about 30%, about 40%, about 50%, about 60%, about 70%, about 80%, about 90%, about 95%, about 100%, about 1.5-fold, about 2-folds, about 4-folds, or more. In still another embodiment, the antibody reduces cAMP concentration in a tissue by at least about 10%, about 20%, about 30%, about 40%, about 50%, about 60%, about 70%, about 80%, about 90%, about 95%, or about 100%. In yet another embodiment, the antibody reduces protein kinase A activity by at least about 10%, about 20%, about 30%, about 40%, about 50%, about 60%, about 70%, about 80%, about 90%, about 95%, or about 100%. In one embodiment, the antibody reduces the phosphorylation of the cAMP response elements of A2aR signal pathway by at least about 10%, about 20%, about 30%, about 40%, about 50%, about 60%, about 70%, about 80%, about 90%, about 95%, or about 100%.

In still another embodiment, the antibody specifically binds to human A2aR and/or cynomolgus A2aR. In yet another embodiment, the antibody specifically binds to human A2aR and/or cynomolgus A2aR with similar affinity. In one embodiment, the antibody does not bind to non-primate A2aR or binds to non-primate A2aR with an affinity that is significantly lower than that of human A2aR and/or cynomolgus A2aR. In still another embodiment, the antibody reduces the production of intracellular cAMP. In one embodiment, the antibody reduces the concentration of cAMP in a tissue. In one embodiment, the antibody reduces the intracellular concentration of cAMP. In another embodiment, the antibody reduces the extracellular concentration of cAMP in a tissue. In various aspects of the invention and embodiments thereof, the cynomolgus A2aR comprises a sequence as set forth in SEQ ID NO: 51.

In one aspect, the present invention provides an isolated antigen binding molecule, e.g., an antibody, that competes for binding to human A2aR with an antibody of any aspect.

In one embodiment, the antigen binding molecule, e.g., the antibody, is a humanized antibody or a chimeric antibody. In another embodiment, the antibody comprises a heavy chain constant region of a class selected from IgA, IgD, IgE, IgG, or IgM. In still another embodiment, the antibody comprises a heavy chain constant region of the class IgG, and wherein the IgG is selected from the group consisting of IgG4, IgG1, IgG2, and IgG3.

In another aspect, the present invention provides an isolated polynucleotide encoding the antigen binding molecule, e.g., the antibody of any aspects and the various embodiments thereof, an HCVR thereof, an LCVR thereof, a light chain thereof, a heavy chain thereof, or an antigen binding fragment thereof.

In still another aspect, the present invention provides an expression vector that includes comprising the polynucleotide.

In yet another aspect, the present invention provides a recombinant cell that includes the polynucleotide or the expression vector.

In one aspect, the present invention provides a method of producing the antigen binding molecule, e.g., the antibody of any aspects and the various embodiments thereof. The method includes expressing the antibody in the recombinant cell and isolating the expressed antibody.

In one aspect, the present invention provides a pharmaceutical composition. The pharmaceutical composition includes the antigen binding molecule, e.g., the antibody, of any aspects and various embodiments thereof, and a pharmaceutically acceptable carrier or diluent.

In one embodiment, the antibody in the pharmaceutical composition is in an amount effective to (a) specifically bind to a cell surface human or cynomolgus A2aR; (b) reduces the cAMP concentration in a tissue; (c) inhibits the activities of human A2aR; (d) reduces the phosphorylation of the cAMP response elements of A2aR signal pathway; e) improve the immune response of an immune cell; f) reduce protein kinase A activity; and (g) any combination of (a)-(f). In another embodiment, the reduction of the cAMP concentration is a tissue is achieved via the reduction of intracellular cAMP production and/or the reduction of the intracellular and/or extracellular concentration of cAMP as compared to a baseline level. In still another embodiment, the inhibition of A2aR activities is achieved via the inhibition of the physiological activity of adenosine.

In one aspect, the present invention provides a method of inhibiting the activities of an A2aR expressed on a cell surface, comprising contacting the cell the isolated antibody of any aspect or the pharmaceutical composition of any aspect to the subject, thereby inhibiting the A2aR activity in the cell. In one embodiment, the inhibition of the A2aR results in the reduction of cAMP concentration in a tissue by at least about 10%, about 20%, about 30%, about 40%, about 50%, about 60%, about 70%, about 80%, about 90%, about 95%, or about 100%. In another embodiment, the method is used in treating a cancer or a neurodegenerative disease. In still another embodiment, the antigen binding molecule, e.g., the antibody, inhibits the A2aR activities by at least about 10%, about 20%, about 30%, about 40%, about 50%, about 60%, about 70%, about 80%, about 90%, about 95%, or about 100%. In another embodiment, the method is used in treating a cancer or a neurodegenerative disease.

In another aspect, the present invention provides a method of enhancing an immune response in a subject. The method includes administering an isolated antibody of any aspect or the pharmaceutical composition of any aspect to the subject, thereby enhancing the immune response in the subject. In one embodiment, the immune response includes, but is not limited to a) promoting effector T cell function; b) reducing $T_{reg}$ activity; c) preventing $T_{reg}$ expansion; d) enhancing NK cell function; e) promoting type 1 activation of antigen presenting cells; or f) reducing the immunosuppression in a tumor microenvironment. In certain embodiments, the methods of the invention increase an immune response by at least about 10%, about 20%, about 50%, about 60%, about 70%, about 80%, about 90%, about 1-fold, about 2-folds, about 4 folds, or more, as compared to a baseline level.

In still another aspect, the present invention provides a method of inhibiting growth of a tumor in a subject. The method includes administering an isolated antibody of any aspect or the pharmaceutical composition of any aspect to the subject, thereby inhibiting growth of the tumor.

In yet another aspect, the present invention provides a method of treating cancer in a subject, comprising administering an isolated antibody of any aspect or the pharmaceutical composition of aspect, thereby treating the cancer. In one embodiment, the cancer is any cancer described herein. In one particular embodiment, the cancer is selected from the group of triple negative breast cancer (TNBC), pancreatic ductal adenocarcinoma (PDAC), metastatic castration-resistant prostate (mCRPC), renal cell carcinoma (RCC), multiple myeloma, colorectal cancer (CRC), and diffuse large B-cell lymphoma (DLBCL).

In yet another aspect, the present invention provides a method of treating a neurodegenerative disease in a subject, comprising administering an isolated antibody of any aspect or the pharmaceutical composition of aspect, thereby treating the neurodegenerative disease.

In one embodiment, the method of any of above aspect results in activating T cells and directing them to kill a tumor target cell.

In another embodiment, the method of any of above aspect further includes administering an additional therapeutic agent. In one embodiment, the additional therapeutic agent includes any therapeutic agent described herein. In another embodiment, the additional therapeutic agent comprises an anti-tumor agent, radiotherapy, a chemotherapeutic agent, a surgery, a cancer vaccine, an agonist to a stimulatory receptor of an immune cell, a cytokine, a cell therapy, or a checkpoint inhibitor. In one embodiment, the additional therapeutic agent is an antibody, including multi-specific antibody, e.g., bispecific antibody.

In still another embodiment, checkpoint inhibitor is an agent that inhibits PD-1, PD-L1, TIGIT, CTLA-4, PD-1, PD-L1, PD-L2, LAG-3, TIM-3, neuritin, BTLA, CECAM-1, CECAM-5, IL-1R8, VISTA, LAIR1, LILRB1, LILRB2, LILRB3, LILRB4, LILRB5, CD96, CD112R, CD 160, 2B4, TGFβ-R, KIR, NKG2A, and any combination thereof. In yet another embodiment, the checkpoint inhibitor is an agent that inhibits the interaction between PD-1 and PD-L1 and is selected from the group consisting of pembrolizumab, nivolumab, atezolizumab, avelumab, durvalumab, BMS-936559, sintilimab, toripalimab, tislelizumab, camrelizumab, sugemalimab, penpulimab, cadonilimab, sulfamonomethoxine 1, and sulfamethizole 2. In one embodiment, the CTLA inhibitor is ipilimumab, cadonilimab, YH001 (Encure Biopharma).

In yet another embodiment, the additional therapeutic agent is an agonist to a stimulatory receptor of an immune cell selected from OX40, CD2, CD27, CDS, ICAM-1, LFA-1, ICOS (CD278), 4-1 BB (CD137), GITR, CD28, CD30, CD40, BAFFR, HVEM, CD7, LIGHT, NKG2C, NKG2D, SLAMF7, NKp46, NKp80, CD160, B7-H3, CD83 ligand, and any combination thereof.

In one embodiment, the additional therapeutic agent is formulated in the same pharmaceutical composition as the antibody. In another embodiment, the additional therapeutic agent is formulated in a different pharmaceutical composition from the antibody.

In still another embodiment, the additional therapeutic agent is administered prior to the antigen binding molecule, e.g., antibody, of various aspect. In yet another embodiment, the additional therapeutic agent is administered subsequent to the antigen biding molecule, e.g., antibody, subsequently to administering the antibody. In another embodiment, the additional therapeutic agent is administered concurrently with the antigen binding molecule, e.g., the antibody.

In one aspect, the present invention provides a kit. The kit includes the pharmaceutical composition include the pharmaceutic composition of any aspect. In one embodiment, the pharmaceutical composition further comprising any one or more of the additional therapeutic agents described herein.

DETAILED DESCRIPTION

Figure 1:
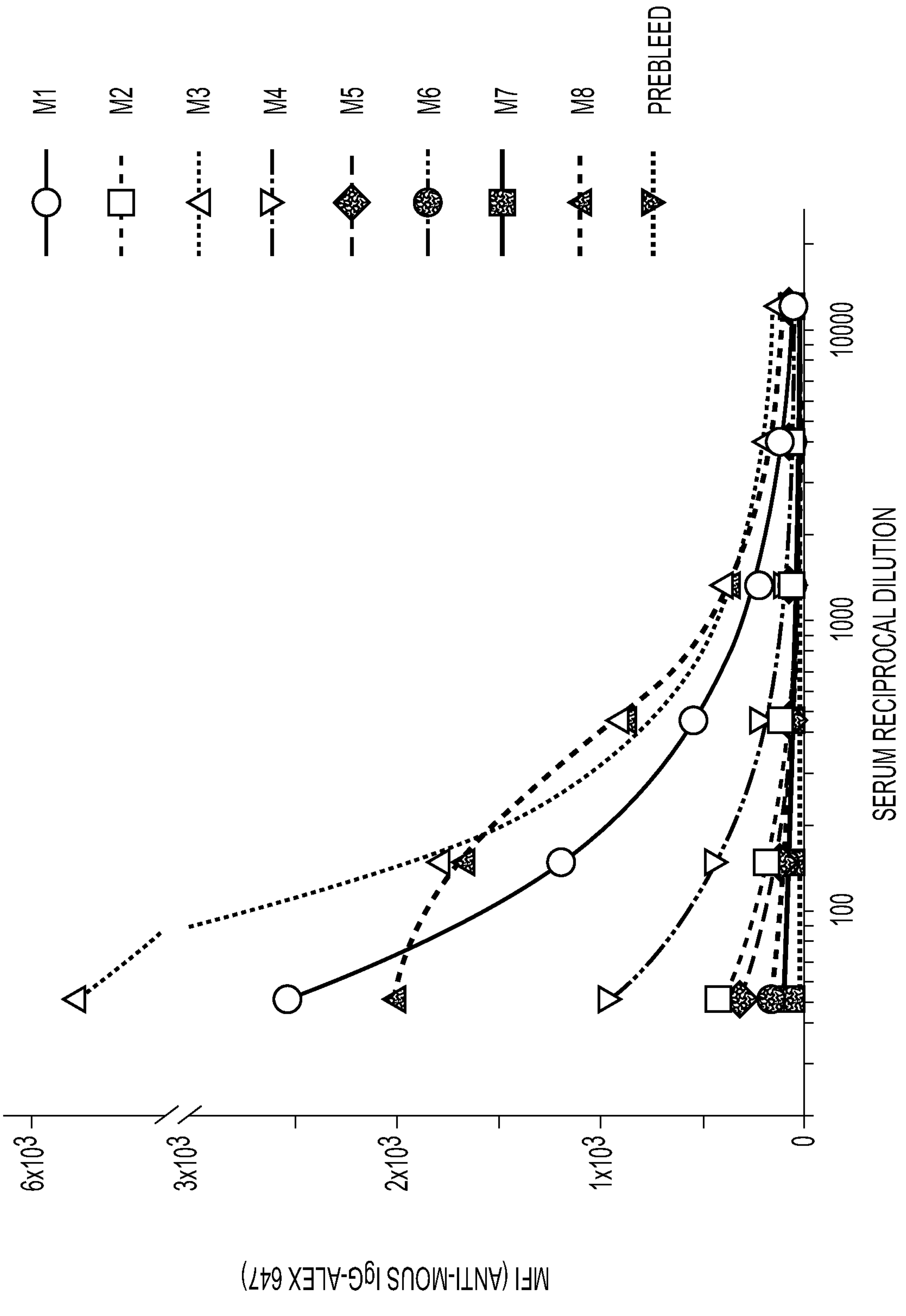
FIG. 1 is a graph showing antibody titers against human A2aR in mouse sera (one curve representing one mouse serum) induced by human A2aR-encoding DNA immunization. Sera from eight mice (M1-M8) were tested for antibody titers determined through binding to human A2aR-overexpressing Expi293 cells by flow cytometry assay. MFI: mean fluorescence intensity.

The invention and accompanying drawings will now be discussed to enable one skilled in the art to practice the present invention. The skilled artisan will understand, however, that the inventions described below can be practiced without employing these specific details, or that they can be used for purposes other than those described herein. Indeed, they can be modified and can be used in conjunction with products and techniques known to those of skill in the art considering the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

It will be appreciated that reference throughout this specification to aspects, features, advantages, or similar language does not imply that all the aspects and advantages may be realized with the present invention should be or are in any single embodiment of the invention. Rather, language referring to the aspects and advantages is understood to mean that a specific aspect, feature, advantage, or characteristic described in connection with an embodiment is included in at least one embodiment of the present invention. Thus, discussion of the aspects and advantages, and similar language, throughout this specification may, but do not necessarily, refer to the same embodiment.

The described aspects, features, advantages, and characteristics of the invention may be combined in any suitable manner in one or more further embodiments. Furthermore, one skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention.

Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present invention. The described aspects and embodiments of the application are not limited to the methods and materials described.

Further, with respect to the teachings in the present invention, any cited references, any issued patent or patent application publication described in this application is expressly incorporated by reference herein.

I. DEFINITIONS

In order that the present invention may be more readily understood, certain terms are first defined. In addition, it should be noted that whenever a value or range of values of a parameter are recited, it is intended that values and ranges intermediate to the recited values are also intended to be part of this invention.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

Where the phrases "in one embodiment", "in another embodiment" "in other embodiments", "in some embodiments" or "in certain embodiments" are used, the present disclosure should be construed as embracing combinations of any of the features defining the different embodiments described therein, unless the features are not combinable with one another, are mutually exclusive, or are expressly disclaimed herein.

The term "about" or "approximately" usually means within 10%, preferably within 5%, or more preferably within 1%, of a given value or range.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" (i.e., the value), "greater than or equal to" (i.e., the value) and possible ranges between values are also disclosed, as appropriately understood by the skilled artisan. For example, if the value "10" is disclosed the "less than or equal to 10" as well as "greater than or equal to 10" is also disclosed.

As used herein, the term "agent" is used with reference to any substance, compound (e.g., molecule), supramolecular complex, material, or combination or mixture thereof. A compound may be any agent that can be represented by a chemical formula, chemical structure, or sequence. Example of agents, include, e.g., small molecules, polypeptides, nucleic acids (e.g., RNAi agents, antisense oligonucleotide, aptamers), lipids, polysaccharides, etc. In general, agents may be obtained using any suitable method known in the art. The ordinary skilled artisan will select an appropriate method based, e.g., on the nature of the agent. An agent may be at least partly purified. In some embodiments an agent may be provided as part of a composition, which may contain, e.g., a counter-ion, aqueous or non-aqueous diluent or carrier, buffer, preservative, or other ingredient, in addition to the agent, in various embodiments. In some embodiments an agent may be provided as a salt, ester, hydrate, or solvate. In some embodiments an agent is cell-permeable, e.g., within the range of typical agents that are taken up by cells and acts intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates (e.g., with water (i.e., hydrates) or common solvents) and/or may have different crystalline forms (e.g., polymorphs) or different tautomeric forms. Embodiments exhibiting such alternative protonation states, configurations, solvates, and forms are encompassed by the present disclosure where applicable.

In certain embodiment and depending on the context, an "agent" also includes a method of treatment, such as radiotherapy, chemotherapy, or surgery.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gin; Q), Glycine (Gly; G); histidine (His; H), isoleucine (He; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "antagonist" or "inhibitor" refers to a substance that prevents, blocks, inhibits, neutralizes, or reduces a biological activity or effect of another molecule, such as a receptor.

The term "agonist" refers to a substance which promotes (i.e., induces, causes, enhances, or increases) the biological activity or effect of another molecule. The term agonist encompasses substances which bind receptor, such as an antibody, and substances which promote receptor function without binding thereto (e.g., by activating an associated protein).

The term "antibody", as used herein, means any antigen binding molecule or molecular complex comprising at least one complementarity determining region (CDR) that specifically binds to or interacts with a particular antigen (e.g., A2aR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, $C_H1$, $C_H2$ and $C_H3$. Each light chain comprises a light chain variable region (abbreviated herein as LCVR or VL) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-A2aR antibody (or antigen binding fragment thereof) may be identical to the murine or human germ line sequences, or may be naturally or artificially modified. An amino acid consensus sequence may be defined based on a side-by-side analysis of two or more CDRs.

The term "antibody", as used herein, also includes antigen binding fragments of full antibody molecules. The terms "antigen binding portion" of an antibody, "antigen binding fragment" of an antibody, and the like, as used herein, include any naturally occurring, enzymatically obtainable, synthetic, or genetically engineered polypeptide or glycoprotein that specifically binds an antigen to form a complex. Antigen binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen binding fragment," as used herein.

An antigen binding fragment of an antibody will typically comprise at least one variable domain. The variable domain may be of any size or amino acid composition and will generally comprise at least one CDR which is adjacent to or in frame with one or more framework sequences. In antigen binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen binding fragment of an antibody may contain a monomeric $V_H$ or $V_L$ domain.

In certain embodiments, an antigen binding fragment of an antibody may contain at least one variable domain covalently linked to at least one constant domain. Non-limiting, exemplary configurations of variable and constant domains that may be found within an antigen binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (iX) $V_L$-$C_H2$; (X) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen binding fragments may be monospecific or multispecific (e.g., bispecific). A multispecific antigen binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen binding fragment of an antibody of the present invention using routine techniques available in the art.

The antibodies of the invention may be isolated antibodies. An "isolated" molecule, such as an isolated antibody or an isolated polypeptide, as used herein, means a molecule, e.g., an antibody, that has been identified and separated and/or recovered from at least one component of its natural environment. For example, a molecule, e.g., an antibody, that has been separated or removed from at least one component of an organism, or from a tissue or cell in which the antibody naturally exists or is naturally produced, is an "isolated" molecule, e.g., antibody, for purposes of the present invention. An isolated molecule, e.g., an antibody also includes a molecule, e.g., an antibody in situ within a recombinant cell. In certain embodiments, isolated molecules, e.g., antibodies, are molecules, e.g., antibodies that have been subjected to at least one purification or isolation step. According to certain embodiments, an isolated molecule, e.g., antibody may be substantially free of other cellular material and/or chemicals.

The present invention also includes one-arm antibodies that bind A2aR. As used herein, a "one-arm antibody" means an antigen binding molecule comprising a single antibody heavy chain and a single antibody light chain. The one-arm antibodies of the present invention may comprise any of the HCVR/LCVR or CDR amino acid sequences as set forth in Tables 1-9.

The anti-A2aR antibodies herein, or the antigen binding domains thereof, may comprise one or more amino acid substitutions, insertions and/or deletions in the framework and/or CDR regions of the heavy and light chain variable domains as compared to the corresponding germline sequences from which the antigen binding molecules or antigen binding domains were derived. Such mutations can be readily ascertained by comparing the amino acid sequences disclosed herein to germline sequences available from, for example, public antibody sequence databases. The present invention includes antibodies, and the antigen binding domains thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen binding fragments, which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the frameworks and/or CDR residue(s) are mutated to the corresponding residue(s) of a different germline sequence (i.e., a germline sequence that is different from the germline sequence from which the antibody was originally derived). Furthermore, the antibodies, or the antigen binding domains thereof, of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies, or the antigen binding fragments thereof, that contain one or more germline mutations can be easily tested for one or more desired property such as, improved binding specificity, increased binding affinity, improved or enhanced antagonistic or agonistic biological properties (as the case may be), reduced immunogenicity, etc. Antibodies, or the antigen binding fragments thereof, obtained in this general manner are encompassed within the present invention.

The present invention also includes anti-A2aR antibodies comprising variants of any of the HCVR, LCVR, and/or CDR amino acid sequences disclosed herein. Exemplary variants included within this aspect of the invention include variants of any of the HCVR, LCVR, and/or CDR amino acid sequences disclosed herein having one or more conservative substitutions. For example, the present invention includes anti-A2aR antibodies and antigen binding proteins having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in the Tables herein.

Light chains are classified as either kappa or lambdamko (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

As used herein, the term "light chain constant region" or "CL" are used interchangeably herein with reference to amino acid sequences derived from an antibody light chain. Preferably, the light chain constant region comprises at least one of a constant kappa domain or constant lambda domain.

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In some embodiments, a polypeptide of the disclosure comprises a polypeptide chain comprising a CH3 domain. Further, an antibody for use in the disclosure may lack at least a portion of a CH2 domain (e.g., all or part of a CH2 domain). It should be understood that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

A "light chain-heavy chain pair" refers to the collection of a light chain and heavy chain that can form a dimer through a disulfide bond between the CL domain of the light chain and the CH1 domain of the heavy chain.

The subunit structures and three-dimensional configurations of the constant regions of the various immunoglobulin classes are well known. As used herein, the term "VH domain" includes the N terminal variable domain of an immunoglobulin heavy chain and the term "CH1 domain" includes the first (most N terminal) constant region domain of an immunoglobulin heavy chain. The CH1 domain is adjacent to the VH domain and is N-terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system). The CH2 domain is unique in that it is not closely paired with another domain. Rather, two N-linked branched carbohydrate chains are interposed between the two CH2 domains of an intact native IgG molecule. The CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains.

As used herein the term "disulfide bond" includes a covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et a. (1997) Nucleic Acids Res. 25:3389-402.

The term "antibody" encompasses various broad classes of polypeptides that can be distinguished biochemically. Those skilled in the art will appreciate that heavy chains are classified as alpha, delta, epsilon, gamma, and mu, or $\alpha$, $\delta$, $\varepsilon$, $\gamma$ and $\mu$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are within the scope of the present disclosure, the following discussion will generally be directed to the IgG class of immunoglobulin molecules.

Antibodies of the disclosure include, but are not limited to, polyclonal, monoclonal, multispecific, bispecific, trispecific, human, humanized, primatized, chimeric and single chain antibodies. Antibodies disclosed herein may be from any animal origin, including birds and mammals. Preferably, the antibodies are human, murine, donkey, rabbit, goat, guinea pig, camel, llama, horse, or chicken antibodies. In some embodiments, the variable region may be condricthoid in origin (e.g., from sharks).

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR). In order to reconstitute the binding affinity and specificity of the parental antibody, the substitution of framework residues from the parental antibody (i.e., the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

As used herein, the phrase "chimeric antibody", refers to an antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

A "single-chain fragment variable" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker.

With regard to IgGs, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration where the light chains bracket the heavy chains starting at the mouth of the "Y" and continuing through the variable region.

The term "variant," as used herein, refers to a polypeptide, e.g., an antibody, or a polynucleotide, that is derived by incorporation of one or more amino acid or nucleotide insertions, substitutions, or deletions in a precursor polypeptide or polynucleotide (e.g., "parent" polypeptide or polynucleotide). In certain embodiments, a variant polypeptide or polynucleotide has at least about 85% amino acid or nucleotide sequence identity, e.g., about 90%, about 91%, about 92%, about 93%, about 94%, about 95%, about 96%, about 97%, about 98%, about 99%, or about 100%, amino acid or nucleotide sequence identity to the entire amino acid or nucleotide sequence of a parent polypeptide or polynucleotide. A variant of a protein or peptide maintains substantially the structures, functions or activities of the protein. For example, a variant of an antibody maintains the function or activities of specifically binding to its antigen and/or modulate, e.g., inhibit, the activities of the antigen. In the case of a polynucleotide, a variant thereof maintains its function or activities of the parent polynucleotide. For example, a variant polynucleotide may encode a protein or peptide that has similar functions or activities of the polypeptide encoded by the parent polynucleotide. The term "sequence identity," as used herein, refers to a comparison between pairs of nucleic acid or polypeptide molecules, i.e., the relatedness between two amino acid sequences or between two nucleotide sequences. In general, the sequences are aligned so that the highest order match is obtained. Methods for determining sequence identity are known and can be determined by commercially available computer programs that can calculate the percentage of identity between two or more sequences. A typical example of such a computer program is BLAST, or CLUSTAL.

As used herein, the terms "specific binding" or "specifically binds" refer to an ability to discriminate between possible binding partners in the environment in which binding is to occur. In some embodiments, an antibody that interacts, e.g., preferentially interacts, with one particular antigen when other potential antibodies are present is said to "bind specifically" to the antigen with which it interacts. In some embodiments, specific binding is assessed by detecting or determining the degree of association between the antibody and its targeted antigen; in some embodiments, specific binding is assessed by detecting or determining degree of dissociation of an antibody-antigen complex. In some embodiments, specific binding is assessed by detecting or determining ability of the antibody to compete with an alternative interaction between its target and another antibody. In some embodiments, specific binding is assessed by performing such detections or determinations across a range of concentrations. In general, an antibody binds to an epitope via its antigen binding domain, and that the binding entails some complementarity between the antigen binding domain and the epitope. Thus, an antibody is said to "specifically bind" to an epitope when it binds to that epitope via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B", or antibody "A" may be said to bind to epitope "C" with a higher specificity than it has for related epitope "D". In some embodiments, an antibody or an antibody fragment "has specificity to" an antigen if the antibody or the antigen binding fragment thereof forms a complex with the antigen with a dissociation constant ($K_d$) of $10^{-6}$M or less, $10^{-7}$M or less, $10^{-8}$M or less, $10^{-9}$M or less, or $10^{-10}$M or less. In certain embodiments, the specific binding of the antigen binding molecules, e.g., anti-human A2aR antibodies or antigen binding fragment thereof, can be shown by the preferential binding of the antigen binding molecules to human A2aR expressed on a cell surface using assays described in Examples 4-7, or substantially similar methods.

As used herein, the term "A2aR" refers to the adenosine type A2A receptor. Unless indicated otherwise, such as by specific reference to human A2aR, the term "A2aR" includes all mammalian species of native A2aR from, e.g., human, primate, rodent, canine, feline, equine, and bovine. The nucleotide and amino acid sequence of A2aR is known and may be found in, for example, GenBank Accession Nos. NP_000666.2, NP 033760.2, XP_038954384.1, EHH65694.1, EAW59658.1, XP_015313061.1, NP_445746.3, and XP_001095531.1, the entire contents of each of which are incorporated herein by reference. The following is an exemplary human A2aR amino acid sequence:

(SEQ ID NO: 50)
MPIMGSSVYITVELAIAVLAILGNVLVCWAVWLNSNLQNVTNYFVVSLA

AADIAVGVLAIPFAITISTGFCAACHGCLFIACFVLVLTQSSIFSLLAI

AIDRYIAIRIPLRYNGLVTGTRAKGIIAICWVLSFAIGLTPMLGWNNCG

QPKEGKNHSQGCGEGQVACLFEDVVPMNYMVYFNFFACVLVPLLLMLGV

YLRIFLAARRQLKQMESQPLPGERARSTLQKEVHAAKSLAIIVGLFALC

WLPLHIINCFTFFCPDCSHAPLWLMYLAIVLSHTNSVVNPFIYAYRIRE

FRQTFRKIIRSHVLRQQEPFKAAGTSARVLAAHGSDGEQVSLRLNGHPP

GVWANGSAPHPERRPNGYALGLVSGGSAQESQGNTGLPDVELLSHELKG

VCPEPPGLDDPLAQDGAGVS

An exemplary cynomolgus A2aR amino acid sequence is shown below:

(SEQ ID NO: 51)
VPIMGSSVYITVELAIAVLAILGNVLVCWAVWLNSNLQNVTNYFVVSLA

AADIAVGVLAIPFAITISTGFCAACHGCLFIACFVLVLTQSSIFSLLAI

AIDRYIAIRIPLRYNGLVTGTRAKGIIAICWVLSFAIGLTPMLGWNNCG

QPKEGKNHSQGCGEGQVACLFEDVVPMNYMVYFNFFACVLVPLLLMLGV

YLRIFLAARRQLKQMESQPLPGERARSTLQKEVHAAKSLAIIVGLFALC

WLPLHIINCFTFFCPDCNHAPLWLMYLAIVLSHTNSVVNPFIYAYRIRE

FRQTFRKIIRSHVLRQQEPFKAAGTSARVLAAHGSDGEQVSLRLNGHPP

GVWANGSAPHPERRPNGYALGLVSGGSTQESQGNTSLPDVELLSHELKG

VCPEPPGLDDPLAQGGAGVS

The term "anti-A2aR antibody," or "A2aR antibody" refers to an antibody or polypeptide that specifically binds to A2aR. In certain embodiments, the anti-A2aR antibody is able to inhibit A2aR biological activity and/or downstream signal pathways mediated by A2aR. Anti-A2aR antibodies encompass antibodies or polypeptides contain one or more antigen binding domains in the form of CDRs or variable regions. In certain embodiments, anti-A2aR antibodies of the invention block, antagonize, suppress or reduce (to any degree including significantly) A2aR biological activity, including downstream events mediated by A2aR, such as A2aR binding and downstream signaling, stimulation of tumor growth, inhibition of anti-tumor immune responses, and immunosuppression in immune-compromised disease states.

The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

As used herein, the term "recombinant" refers to polypeptides or polynucleotides that do not exist naturally and which may be created by combining polynucleotides or polypeptides in arrangements that would not normally occur together.

When describing polypeptide domain arrangements with hyphens between individual domains (e.g., CH2-CH3), it should be understood that the order of the listed domains is from the N-terminus to the C-terminus.

The term "immunoconjugate" refers to an antibody which is fused by covalent linkage to a peptide or small molecule drug. The peptide or small molecule drug can be linked to the C-terminus of a constant heavy chain or to the N-terminus of a variable light and/or heavy chain.

The term "inhibit," "inhibition," "reduce," and "reduction," in the context of the level of A2aR activity, refers to a statistically significant decrease in such level. The decrease can be, for example, at least 20%, 25%, 30%, 35%, 40%, 45%, 50%, 55%, 60%, 65%, 70%, 75%, 80%, 85%, 90%, or 95%, or below the level of detection for the detection method. For example, the inhibition or reduction of the A2aR activity can be determined by a decrease of intracellular cAMP concentration using the method as described in Example 4.

The terms "treat" and "treatment" refer to the amelioration of one or more symptoms associated with a disease or disorder. As such, these terms refer to any indicia of success in the therapy or amelioration of an injury, disease, pathology or condition, including prevention or delay of the onset of one or more symptoms of the disease or disorder; lessening of the severity or frequency of one or more symptoms of the disease or disorder; any objective or subjective parameter such as abatement; remission; diminishing of symptoms or making the injury, pathology or condition more tolerable to the patient; slowing in the rate of degeneration or decline; making the final point of degeneration less debilitating; and/or improving a patient's physical or mental well-being. "Treating" and treatment" may also include prophylactic treatment.

The phrases "to a patient in need thereof", "to a patient in need of treatment" or "a subject in need of treatment" includes subjects, such as mammalian subjects, that would benefit from administration of the antibodies of the present disclosure for treatment of a cell proliferative disorder.

The term "prevent" refers to a decrease in the occurrence of disease symptoms (e.g., associated with A2aR activity or function thereof) in a patient. As indicated above, the prevention may be complete (no detectable symptoms) or partial, such that fewer symptoms are observed than would likely occur absent treatment.

The terms "therapeutically effective amount", "pharmacologically effective amount", and "physiologically effective amount" are used interchangeably to mean the amount of an active agent sufficient to ameliorate at least one symptom of the disease or disorder. For example, for the given parameter, a therapeutically effective amount will show an increase or decrease of at least 5%, 10%, 15%, 20%, 25%, 40%, 50%, 60%, 75%, 80%, 90%, 95%, 99%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. The precise amount will depend upon numerous factors, e.g., the particular active agent, the components and physical characteristics of the composition, intended patient population, patient considerations, including weight, sex and the like, and can readily be determined by one skilled in the art, based upon the information provided herein or otherwise available in the relevant literature.

The terms, "improve," "increase," or "reduce," as used in this context, indicate values or parameters relative to a baseline/control/reference measurement, such as a measurement in a cell or a tissue prior to initiation of the treatment described herein, or a measurement in a cell or a tissue in the absence of the treatment described herein, a measurement in the same individual prior to initiation of the treatment described herein, or a measurement in a control individual (or a standard measurement derived from multiple control individuals, such as the average value of the multiple control individuals) in the absence of the treatment described herein.

A "control individual" is an individual with similar condition, e.g., an individual afflicted with the same cell proliferative disorder as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

The term "cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm, cancer or tumor.

The term "cancer" refers to any one of a variety of malignant neoplasms characterized by the proliferation of cells that have the capability to invade surrounding tissue and/or metastasize to new colonization sites, and includes carcinomas, sarcomas, adenocarcinomas, melanomas, leukemias, lymphomas, germ cell tumors and blastomas, including both solid and lymphoid cancers. Exemplary cancers that may be treated in accordance with the compositions and methods of the present invention include cancers of the brain, bladder, breast, cervix, colon, head and neck, kidney, lung, non-small cell lung, mesothelioma, ovary, prostate, stomach and uterus, leukemia, and medulloblastoma.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, pancreatic ductal adenocarcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

The term "lymphoma" refers to a group of cancers affecting hematopoietic and lymphoid tissues, which begins in lymphocytes, the blood cells that are found primarily in lymph nodes, spleen, thymus, and bone marrow. Two main types of lymphoma are non-Hodgkin's lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas include, but are not limited to, cutaneous T-cell lymphoma, peripheral T-cell lymphoma, anaplastic large cell lymphoma, mycosis fungoides, and precursor T-lymphoblastic lymphoma.

The term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Additional cancers include, for example, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

II. A2AR ANTIBODIES AND ANTIGEN BINDING PROTEINS

The present invention provides A2aR antigen binding molecules that bind specifically to A2aR. As used herein, the term "antigen binding molecule" refers to a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen binding molecule is an antibody or an antigen binding fragment thereof, as those terms are defined elsewhere herein. In certain embodiments, the antigen binding molecules of the present invention inhibit one or more of its biological functions of A2aR.

In certain embodiments, the A2aR is a human A2aR. An exemplary human A2aR has the amino acid sequence as set forth in SEQ ID NO: 50. In some embodiments, the A2aR is a cynomolgus A2aR. An exemplary cynomolgus A2aR has the amino acid sequence as set forth in SEQ ID NO: 51.

1. The Sequences of Exemplary Antigen Binding Molecules

The A2aR antigen binding molecules may be in the form of monoclonal antibodies; one or more polypeptide fragment(s) containing one or more A2aR antigen binding domains; or one or more nucleic acids encoding one or more A2aR binding domains.

In various exemplary embodiments of the present invention, an antigen binding molecules, e.g., an anti-A2aR antibodies or antigen binding fragments thereof, includes (1) a heavy chain variable region, wherein the heavy chain variable region comprises three complementarity determining regions (HCDRs): HCDR1, HCDR2 and HCDR3, wherein HCDR1 has an amino acid sequence that is about 80%, 85%, 90%, 95%, 96%, 97%, 98%, 99% to about 100% identical to an amino acid sequence selected from the group consisting of SEQ ID NOs: 1, 4, and 6; wherein HCDR2 has an amino acid sequence that is about 80%, 85%, 90%, 95%, 96%, 97%, 98%, 99% to about 100% identical to an amino acid sequence selected from the group consisting of SEQ ID NOs: 2, 5, and 7, and wherein HCDR3 has an amino acid sequence that is about 80%, 85%, 90%, 95%, 96%, 97%, 98%, 99% to about 100% identical to an amino acid sequence set forth in SEQ ID NO: 3; and (2) a light chain variable region, wherein the light chain variable region comprises three complementarity determining regions (LCDRs): LCDR1, LCDR2 and LCDR3, wherein LCDR1 has an amino acid sequence that is about 80%, 85%, 90%, 95%, 96%, 97%, 98%, 99% to about 100% identical to an amino acid sequence selected from the group consisting of SEQ ID NOs: 25 and 28; wherein LCDR2 has an amino acid sequence that is about 80%, 85%, 90%, 95%, 96%, 97%, 98%, 99% to about 100% identical to an amino acid sequence set forth in SEQ ID NO: 26, and wherein LCDR3 has an amino acid sequence that is about 80%, 85%, 90%, 95%, 96%, 97%, 98%, 99% to about 100% identical to an amino acid sequence selected from the group consisting of SEQ ID NOs: 27 and 29; wherein the antigen binding molecule binds specifically to human A2aR. Exemplary HCDR– and LCDR amino acid sequences corresponding to the exemplary anti-human A2aR monoclonal antibodies disclosed in the present invention are shown in Tables 1-5.

The amino acid sequence boundaries of a CDR can be determined by one of skill in the art using any of a number of known numbering schemes, including those described by Kabat et al., supra ("Kabat" numbering scheme); Al-Lazikani et al., 1997, J. Mol. Biol., 273:927-948 ("Chothia" numbering scheme); MacCallum et al., 1996, J. Mol. Biol. 262:732-745 ("Contact" numbering scheme); Lefranc et al., Dev. Comp. Immunol., 2003, 27:55-77 ("IMGT" numbering scheme); and Honegge and Pluckthun, J. Mol. Biol, 2001, 309:657-70 ("AHo" numbering scheme); each of which is incorporated by reference in its entirety. Tables 1 and 2 show the sequences of heavy chain CDRs of exemplary antibodies of the invention according to Kabat numbering scheme and IMGT numbering scheme, respectively. Table 3 shows the sequences of heavy chain CDRs of exemplary antibodies of the invention, in which the CDR sequences are defined by combining the CDRs based on Kabat and IMGT numbering schemes. Tables 4 and 5 show the sequences of light chain CDRs of exemplary antibodies of the invention according to Kabat numbering scheme and IMGT numbering scheme.

In certain embodiments, the present invention includes antigen binding molecules, e.g., anti-A2aR antibodies or antigen binding fragments thereof, comprising CDRs which are defined based on Kabat and IMGT numbering scheme, or the combination thereof. Accordingly, in certain embodiments, the present invention includes antigen binding molecules, e.g., anti-A2aR antibodies or antigen binding fragments thereof, comprising (1) a HCDR1 having an amino acid sequence selected from the HCDR1 sequences listed in Table 2; (2) a HCDR2 having an amino acid sequence selected from the HCDR2 sequences listed in Table 2; (3) a HCDR3 having an amino acid sequence selected from the HCDR3 sequences listed in Table 2; (4) a LCDR1 having an amino acid sequence selected from the LCDR1 sequences listed in Table 5; (5) a LCDR2 having an amino acid sequence selected from the LCDR2 sequences listed in Table 5; and (6) a LCDR3 having an amino acid sequence selected from the LCDR3 sequences listed in Table 5.

In certain embodiments, the present invention includes antigen binding molecules, e.g., anti-A2aR antibodies or antigen binding fragments thereof, comprising (1) a HCDR1 having an amino acid sequence selected from the HCDR1 sequences listed in Table 3; (2) a HCDR2 having an amino acid sequence selected from the HCDR2 sequences listed in Table 3; (3) a HCDR3 having an amino acid sequence selected from the HCDR3 sequences listed in Table 3; (4) a LCDR1 having an amino acid sequence selected from the LCDR1 sequences listed in Table 4; (5) a LCDR2 having an amino acid sequence selected from the LCDR2 sequences listed in Table 4; and (6) a LCDR3 having an amino acid sequence selected from the LCDR3 sequences listed in Table 4.

As used herein, a "position" in a CDR refers to the amino acid counted from the N-terminus of the CDR. For example, position 1 in HCDR1 refers to the first amino acid in HCDR1. Accordingly, in mAB 1B5-3D7, position 1 of HCDR1 based on Kabat numbering scheme is an arginine (R).

TABLE 1

Amino Acid Sequences of Heavy Chain CDRs of Exemplary Antibodies (Kabat Numbering Scheme)

| mAb | HCDR1 | SEQ ID NO: | HCDR2 | SEQ ID NO: | HCDR3 | SEQ ID NO: |
|---|---|---|---|---|---|---|
| 1B5-3D7 | RFWMN | 1 | RIDPYDSETQYNHKFWD | 2 | SLYGKGDY | 3 |
| 3F6-9G5 | SYWMN | 4 | RIDPSDSEAHYHHKFWG | 5 | SLYGKGDY | 3 |
| 3F8-12E9 | RYWMN | 6 | RIDPSDSETHYNHKFWG | 7 | SLYGKGDY | 3 |
| N/A | $X_1X_2$WMN | 8 | RIDP$X_3$DSE$X_4X_5$Y$X_6$HKFW$X_7$ | 9 | | |

As used in herein, $X_1$ is S or R, $X_2$ is Y or F, $X_3$ is S or Y, $X_4$ is A or T, $X_5$ is H or Q, $X_6$ is H or N, and $X_7$ is D or G.

TABLE 2

Amino Acid Sequences of Heavy Chain CDRs of Exemplary Antibodies (IMGT Numbering Scheme)

| mAb | HCDR1 | SEQ ID NO: | HCDR2 | SEQ ID NO: | HCDR3 | SEQ ID NO: |
|---|---|---|---|---|---|---|
| 1B5-3D7 | GFTFTRFW | 10 | IDPYDSET | 11 | GRSLYGKGDY | 12 |
| 3F6-9G5 | GFAFTSYW | 13 | IDPSDSEA | 14 | LRSLYGKGDY | 15 |
| 3F8-12E9 | GFTFTRYW | 16 | IDPSDSET | 17 | LRSLYGKGDY | 15 |
| N/A | GF$X_8$FT$X_9X_{10}$W | 18 | IDP$X_{11}$DSE$X_{12}$ | 19 | $X_{13}$RSLYGKGDY | 20 |

As used in herein, $X_8$ is A or T, $X_9$ is R or S, $X_{10}$ is For Y, $X_{11}$—is S or Y, $X_{12}$ is A or T, and $X_{13}$—is G or L.

TABLE 3

Amino Acid Sequences of Heavy Chain CDRs of Exemplary Antibodies (Combing Kabat and IMGT Numbering Scheme)

| mAb | HCDR1 | SEQ ID NO: | HCDR2 | SEQ ID NO: | HCDR3 | SEQ ID NO: |
|---|---|---|---|---|---|---|
| 1B5-3D7 | GFTFTRFWMN | 21 | RIDPYDSETQYNHKFWD | 2 | GRSLYGKGDY | 12 |
| 3F6-9G5 | GFAFTSYWMN | 22 | RIDPSDSEAHYHHKFWG | 5 | LRSLYGKGDY | 15 |
| 3F8-12E9 | GFTFTRYWMN | 23 | RIDPSDSETHYNHKFWG | 7 | LRSLYGKGDY | 15 |
| N/A | GF$X_{14}$FT$X_{15}X_{16}$WMN | 24 | RIDP$X_3$DSE$X_4X_5$Y$X_6$HKFW$X_7$ | 9 | $X_{13}$RSLYGKGDY | 20 |

As used in herein, $X_{14}$ is A or T, $X_{15}$ is R or S, and $X_{16}$ is F or Y.

TABLE 4

Amino Acid Sequences Light Chain CDRs of Exemplary Antigen Binding Molecules (Kabat Numbering Scheme)

| mAb | LCDR1 | SEQ ID NO: | LCDR2 | SEQ ID NO: | LCDR3 | SEQ ID NO: |
|---|---|---|---|---|---|---|
| 1B5-3D7 | RSSQSIVHSNGNTYLE | 25 | KVSNRFS | 26 | FQGSHVPLT | 27 |
| 3F6-9G5 | RSSQSLVHRNGNTYLE | 28 | KVSNRFS | 26 | YQGSHVPLT | 29 |
| 3F8-12E9 | RSSQSIVHSNGNTYLE | 25 | KVSNRFS | 26 | YQGSHVPLT | 29 |
| N/A | RSSQS$X_{17}$VH$X_{18}$NGNTYLE | 30 | | | $X_{19}$QGSHVPLT | 31 |

As used in herein, $X_{17}$ is L or I, $X_{18}$ is R or S, and $X_{19}$ is Y or F.

TABLE 5

Amino Acid Sequences Light Chain CDRs of Exemplary Antigen Binding Molecules (IMGT Numbering Scheme)

| mAb | LCDR1 | SEQ ID NO: | LCDR2 | SEQ ID NO: | LCDR3 | SEQ ID NO: |
|---|---|---|---|---|---|---|
| 1B5-3D7 | QSIVHSNGNTY | 32 | KVS | N/A | FQGSHVPLT | 27 |
| 3F6-9G5 | QSLVHRNGNTY | 33 | KVS | N/A | YQGSHVPLT | 29 |
| 3F8-12E9 | QSIVHSNGNTY | 32 | KVS | N/A | YQGSHVPLT | 29 |
| N/A | QS$X_{20}$VH$X_{21}$NGNTY | 34 | | | $X_{19}$QGSHVPLT | 31 |

As used in herein, $X_{20}$ is L or I, and $X_{21}$ is R or S.

In some embodiments, the antibody, or the antigen binding fragment thereof, comprises: (1) a heavy chain variable region (HCVR) having an amino acid sequence that is about 80%, 85%, 90%, 95%, 96%, 97%, 98%, 99% to about 100% identical to an amino acid sequence selected from the group consisting of SEQ ID NOs: 35, 36, and 37; and (2) a light chain variable region (LCVR) having an amino acid sequence that is about 80%, 85%, 90%, 95%, 96%, 97%, 98%, 99% to about 100% identical to an amino acid sequence selected from the group consisting of SEQ ID NOs: 41, 42, and 43, wherein the antibody, or the antigen binding fragment thereof, binds specifically to human A2aR. Exemplary HCVR- and LCVR amino acid sequences corresponding to the exemplary anti-human A2aR monoclonal antibodies disclosed in the present invention are shown in Tables 6-8. Tables 9 and 10 show the exemplary nucleotide sequences of the DNAs that encode the HCVR and LCVR, respectively, of the exemplary anti-human A2aR antibody of the present invention.

TABLE 6

Amino Acid Sequences of HCVRs of Exemplary Antigen Binding Molecules

| mAbs | HCVR Sequences | SEQ ID NOs |
|---|---|---|
| 1B5-3D7 | QVQLQQPGTELVKPGAPVKLSCK TSGFTFTRFWMNWVRQRPGRGLE WIGRIDPYDSETQYNHKFWDRAT LTVDKSSSTVYIQLSSLTSEDSA VYYCGRSLYGKGDYWGQGTTLTV SS | 35 |
| 3F6-9G5 | QVQLQQPGTELVKPGAPVRLSCK ASGFAFTSYWMNWVRQRPGRGLE WIGRIDPSDSEAHYHHKFWGKAT LTVDKSSSTVYIQLNGLTSEDSA VYYCLRSLYGKGDYWGHGTTLTV SS | 36 |
| 3F8-12E | QVQLQQPGTELVKPGAPVKLSCK ASGFTFTRYWMNWVKQRPGRGLE WIGRIDPSDSETHYNHKFWGKAT LTVDKSSSTAYIQLNSLTSEDSA VYYCLRSLYGKGDYWGQGTTLTV SS | 37 |

TABLE 7

Amino Acid Sequences of Pyroglutamylated HCVRs of Exemplary Antigen Binding Molecules

| mAbs | Pyroglutamylated HCVR Sequences | SEQ ID NOs |
|---|---|---|
| 1B5-3D7 | pEVQLQQPGTELVKPGAPVKLSCKTSGFTFTRFWMNWVRQRPGRGLEWIGRIDPYDSETQYNHKFWDRATLTVDKSSSTVYIQLSSLTSEDSAVYYCGRSLYGKGDYWGQGTTLTVSS | 38 |
| 3F6-9G5 | pEVQLQQPGTELVKPGAPVRLSCKASGFAFTSYWMNWVRQRPGRGLEWIGRIDPSDSEAHYHHKFWGKATLTVDKSSSTVYIQLNGLTSEDSAVYYCLRSLYGKGDYWGHGTTLTVSS | 39 |
| 3F8-12E9 | pEVQLQQPGTELVKPGAPVKLSCKASGFTFTRYWMNWVKQRPGRGLEWIGRIDPSDSETHYNHKFWGKATLTVDKSSSTAYIQLNSLTSEDSAVYYCLRSLYGKGDYWGQGTTLTVSS | 40 |

TABLE 8

Amino Acid Sequences of LCVRs of Exemplary Antigen Binding Molecules

| mAbs | LCVR Sequences | SEQ ID NOs |
|---|---|---|
| 1B5-3D7 | DVLMTQSPLSLPVSLGDQASISCRSSQSIVHSNGNTYLEWYLQRPGQSPKLLIYKVSNRFSGVPDRFSGSGSGTYFTLRISRVEAEDLGIYYCFQGSHVPLTFGSGTTLELK | 41 |
| 3F6-9G5 | DVLMTQTPLSLSVRLGDQASISCRSSQSLVHRNGNTYLEWYLQRPGQSPKLLIYKVSNRFSGVPDRFSGSGSGTDFTLKISRVEAEDLGVYYCYQGSHVPLTFGSGTKLEIK | 42 |
| 3F8-12E9 | DVLMTQTPLSLSVGLGDQASISCRSSQSIVHSNGNTYLEWYLQRPGQSPKLLIYKVSNRFSGVPDRFSGSGSGTDFTLKISRVEAEDLGVYYCYQGSHVPLTFGSGTKLEIK | 43 |

TABLE 9

Nucleotides Sequences Encoding HCVRs of Exemplary Antigen Binding Molecules

| mAbs | Sequences | SEQ ID NOs |
|---|---|---|
| 1B5-3D7 | CAGGTCCAACTTCAGCAGCCTGGGACTGAACTTGTGAAGCCTGGGGCTCCAGTGAAGCTGTCCTGTAAGACTTCTGGCTTCACCTTCACCAGGTTCTGGATGAACTGGGTGAGGCAGAGGCCTGGACGAGGCCTCGAGTGGATTGGAAGGATTGATCCTTACGATAGTGAAACTCAATATAATCACAAATTCTGGGACAGGGCCACACTGACTGTTGACAAATCCTCCAGCACAGTCTACATCCAACTCAGCAGCCTGACATCTGAGGACTCTGCGGTCTATTACTGTGGAAGATCCCTATATGGTAAAGGGGACTACTGGGGCCAAGGCACCACTCTCACAGTCTCCTCA | 44 |
| 3F6-9G5 | CAGGTCCAACTGCAGCAGCCTGGGACTGAGCTTGTGAAGCCTGGGGCTCCAGTGAGGCTGTCCTGCAAGGCTTCTGGCTTCGCCTTCACCAGCTACTGGATGAACTGGGTGAGGCAGAGGCCTGGACGAGGCCTCGAGTGGATTGGAAGGATTGATCCTTCCGATAGTGAAGCTCACTATCATCATAAATTCTGGGGCAAGGCCACACTGACTGTTGACAAATCCTCCAGCACCGTTTACATCCAGCTCAACGGCCTGACATCTGAGGACTCTGCGGTCTATTACTGTCTAAGATCCCTATATGGTAAAGGGGACTACTGGGGCCATGGCACCACTCTCACAGTCTCCTCA | 45 |
| 3F8-12E9 | CAGGTCCAACTGCAGCAGCCTGGGACTGAGCTTGTGAAGCCTGGGGCTCCAGTGAAGCTGTCCTGCAAGGCTTCTGGCTTCACCTTCACCCGCTACTGGATGAACTGGGTGAAGCAGAGGCCTGGACGAGGCCTCGAGTGGATTGGAAGGATTGATCCTTCCGATAGTGAAACTCACTATAATCATAAATTCTGGGGCAAGGCCACACTGACTGTTGACAAATCCTCCAGCACAGCCTACATCCAACTCAACAGCCTGACATCTGAGGACTCTGCGGTCTATTACTGTCTAAGATCCCTATATGGTAAAGGGGACTACTGGGGCCAAGGCACCACTCTCACAGTCTCCTCA | 46 |

TABLE 10

Nucleotides Sequences Encoding LCVRs of Exemplary Antigen Binding Molecules

| mAbs | Sequences | SEQ ID NOS |
|---|---|---|
| 1B5-3D7 | GATGTTTTGATGACCCAGTCTCCACTCTCCCTGCCTGTCAGTCTTGGAGATCAAGCCTCCATCTCTTGCAGATCTAGTCAGAGCATTGTACATAGTAATGGAAACACCTATTTAGAATGGTACCTGCAGAGACCAGGCCAGTCTCCAAAACTCCTGATCTACAAAGTTTCCAACCGATTTTCTGGGGTCCCAGACAGGTTCAGTGGCAGTGGATCAGGGACATATTTCACACTCAGGATCAGCAGAGTGGAGGCTGAAGATCTGGGAATTTATTACTGCTTTCAAGGTTCACATGTTCCTCTCACGTTCGGCTCGGGGACAACATTGGAACTAAAA | 47 |

TABLE 10-continued

| Nucleotides Sequences Encoding LCVRs of Exemplary Antigen Binding Molecules | | |
|---|---|---|
| mAbs | Sequences | SEQ ID NOS |
| 3F6-9G5 | GATGTTTTGATGACCCAAACCCC ACTCTCCCTGTCTGTCAGACTTG GAGATCAAGCCTCCATCTCTTGC AGATCTAGTCAGAGTCTTGTACA TAGAAATGGAAACACCTATTTAG AATGGTACCTGCAGAGACCAGGC CAGTCTCCAAAGCTCCTGATCTA CAAGGTTTCCAACCGATTTTCTG GGGTCCCAGACAGGTTCAGTGGC AGTGGATCAGGGACAGATTTCAC ACTCAAGATCAGCAGAGTGGAGG CTGAAGATCTGGGAGTTTATTAC TGCTATCAAGGTTCACATGTTCC TCTCACGTTCGGCTCGGGGACAA AATTGGAAATAAAA | 48 |
| 3F8-12E9 | GATGTTTTGATGACCCAAACTCC ACTCTCCCTGTCTGTCGGTCTTG GAGATCAAGCCTCCATCTCTTGC AGATCTAGTCAGAGTATTGTACA TAGTAATGGAAACACCTATTTAG AATGGTACCTGCAGAGACCAGGC CAGTCTCCAAAGCTCCTGATCTA CAAAGTTTCCAACCGATTTTCTG GGGTCCCAGACAGGTTCAGTGGC AGTGGATCAGGGACAGATTTCAC ACTCAAGATCAGCAGAGTGGAGG CTGAAGATCTGGGAGTTTATTAC TGCTATCAAGGTTCACATGTTCC TCTCACGTTCGGCTCGGGGACAA AATTGGAAATAAAA | 49 |

In certain embodiments, the antigen binding molecules of the present invention, e.g., an antibody or an antigen binding fragment thereof, are modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (See journal of Pharmaceutical Sciences, 2008, Vol. 97, p. 2426-2447, incorporated by reference in its entirety). Examples of an antigen binding molecule, e.g., an antibody or antigen binding fragment thereof which have undergone posttranslational modification include an antigen binding molecule, e.g., an antibody or antigen binding fragments thereof which have undergone pyroglutamylation at the N terminal of the heavy chain variable region and/or deletion of lysine at the C terminal of the heavy chain. The sequences of exemplary antigen binding molecules that undergo pyroglutamylation at the N-terminus is listed in Table 7. As used herein, "pE" refers to pyroglutamic acid when used to represent an amino acid in a polypeptide.

2. Variants of Antigen Binding Molecules

In certain embodiments, the A2aR antigen binding molecules of the present invention, e.g., the anti-A2aR antibodies, can be a monoclonal antibody, a chimeric antibody, a humanized antibody, a Fab, a $(Fab)_2$, a scFv or a multispecific antibody comprising additional binding specificities described herein.

Accordingly, in certain embodiments the anti-A2aR antibodies described herein may be linked to an Fc comprising one or more modifications, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or it may be modified to alter its glycosylation, to alter one or more functional properties of the antibody. More specifically, in certain embodiments, the antibodies in the present invention may include modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for C1q and/or (d) increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g., of the specific Fc region positions identified herein.

For uses where effector function is to be avoided altogether, e.g., when antigen binding alone is sufficient to generate the desired therapeutic benefit, and effector function only leads to (or increases the risk of) undesired side effects, IgG4 antibodies or ADCC-null version of IgG1 L234F, L235E, P331S may be used, or antibodies or fragments lacking the Fc region or a substantial portion thereof can be devised, or the Fc may be mutated to eliminate glycosylation altogether (e.g., N297A). Alternatively, a hybrid construct of human IgG2 (CH1 domain and hinge region) and human IgG4 (CH2 and CH3 domains) may be generated that is devoid of effector function, lacking the ability to bind FcγRs (like IgG2) and activate complement (like IgG4). When using an IgG4 constant domain, it is usually preferable to include the substitution S228P which mimics the hinge sequence in IgG1 and R409K mutation which prevents Fab arm exchange and thereby stabilizes IgG4 molecules, reducing Fab-arm exchange between the therapeutic antibody and endogenous IgG4 in the patient being treated.

In certain embodiments, the anti-A2aR antibody or fragment(s) thereof may be modified to provide increased biological half-life. Various approaches may be employed, including e.g., those that increase the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022. The numbering of residues in the Fc region is that of the EU index of Kabat. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g., if sequences differ between naturally occurring isotypes, or if multiple mutations may be substituted at the position, they are separated by slashes (e.g., "X/Y/Z").

Exemplary Fc variants that increase binding to FcRn and/or improve pharmacokinetic properties include substitutions at positions 259, 308, and 434, including for example 2591, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 305A, 307A, 31 IA, 312A, 378Q, 380A, 382A, 434A (Shields et al. (2001) J. Biol. Chem., 276(9):6591-6604), 252F, 252Y, 252W, 254T, 256Q, 256E, 256D, 433R, 434F, 434Y, 252Y/254T/256E, 433K/434F/436H (Dall'Acqua et al. (2002) J. Immunol., 169:5171-5180, Dall'Acqua et al. (2006) J. Biol. Chem., 281:23514-23524, and U.S. Pat. No. 8,367,805.

Modification of certain conserved residues in IgG Fc (1253, H310, Q311, H433, N434), such as the N434A variant (Yeung et al. (2009) J. Immunol. 182:7663), have been proposed as a way to increase FcRn affinity, thus increasing the half-life of the antibody in circulation (WO 98/023289). The combination Fc variant comprising M428L and N434S has been shown to increase FcRn binding and increase serum half-life up to five-fold (Zalevsky et al. (2010) Nat. Biotechnol. 28:157). The combination Fc variant comprising T307A, E380A and N434A modifications also extends half-life of IgG1 antibodies (Petkova et al. (2006) Int. Immunol. 18:1759). In addition, combination Fc variants comprising M252Y-M428L, M428L-N434H, M428L-N434F, M428L-N434Y, M428L-N434A, M428L-N434M, and M428L-N434S variants have also been shown to extend half-life (U.S. 2006/173170). Further, a combination Fc variant comprising M252Y, S254T and T256E was reported to increase half-life-nearly 4-fold. Dall'Acqua et al. (2006) J. Biol. Chem. 281:23514.

In certain embodiments, the A2aR antigen binding molecule of the present invention is a bispecific antibody, comprising: a first targeting domain that binds specifically to A2aR and a second targeting domain that binds specifically another epitope in A2aR or another protein. In some embodiments, the first targeting domain includes an antigen binding fragment from any of the A2aR antibodies of the present invention.

In certain embodiments, the antigen binding molecules, e.g., anti-A2aR antibodies or antigen binding fragments thereof, of the present invention are chemically conjugated to one or more therapeutically active peptides and/or small molecule drugs. The peptides or small molecule drugs can be attached, for example to reduced SH groups and/or to carbohydrate side chains. Methods for making covalent or non-covalent conjugates of peptides or small molecule drugs with antibodies are known in the art and any such known method may be utilized.

In some embodiments the peptide or small molecule drug is attached to the hinge region of a reduced antibody component via disulfide bond formation. Alternatively, such agents can be attached using a heterobifunctional cross-linkers, such as N-succinyl 3-(2-pyridyldithio)propionate (SPDP). General techniques for such conjugation are well-known in the art. In some embodiments, the peptide or small molecule drug is conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent. Methods for conjugating peptide inhibitors or small molecule drugs to antibodies via antibody carbohydrate moieties is well-known to those of skill in the art. For example, in one embodiment, the method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate. Exemplary methods for conjugating small molecule drugs and peptides to antibodies are described in U.S. Patent Application Publication No. 2014/0356385.

The A2aR antibodies, including fragments thereof and multi-specific forms therefrom, may range in size from 50 kD to 300 kD, from 50 kD to 250 kD, from 60 kD to 250 kD, from 80 kDa to 250 kD, from 100 kD to 250 kD, from 125 kD to 250 kD, from 150 kD to 250 kD, from 60 kD to 225 kD, from 75 kD to 225 kD, from 100 kD to 225 kD, from 125 kD to 225 kD, from 150 kD to 225 kD, from 60 kD to 200 kD, from 75 kD to 200 kD, from 100 kD to 125 kD to 200 kD, from 150 kD to 200 kD, from 60 kD to 150 kD, from 75 kD to 150 kD, from 100 kD to 150 kD, from 60 kD to 125 kD, from 75 kD to 125 kD, from 75 kD to 100 kD, or any range encompassed by any combination of whole numbers listed in the above cited ranges or any ranges specified by any combination of whole numbers between any of the above cited ranges.

3. Biological Characteristics of the Antibodies and Antigen Binding Molecules

The present invention includes antibodies and antigen binding fragments thereof that bind human and cynomolgus A2aR.

The present invention includes A2aR antigen binding molecules, e.g., A2aR antibodies or the antigen binding fragments thereof, which are capable of specifically binding to human and cynomolgus A2aR expressed on a cell surface and inhibits the A2aR activities or functions. According to certain embodiments, the antigen binding molecules blocks the interaction between the human A2aR expressed on a cell surface and A2aR agonist. The extent to which an A2aR antigen binding protein, e.g., an A2aR antibody or an antigen binding fragment thereof, inhibits the activities of the A2aR, can be assessed by the assays described in Example 4, or a substantially similar assay. The present invention includes antigen binding molecules, e.g., antibodies, which blocks the interaction between human A2aR expressed on a cell surface and an A2aR agonist with an $IC_{50}$ value from $4.5\times10^{-9}$ M to about $1.5\times10^{-9}$ M, or less, as determined using an assay as set forth in Example 4, or a substantially similar assay.

The present invention includes A2aR antigen binding molecules, e.g., A2aR antibodies, which bind to human A2aR expressed on a cell surface specifically. In certain embodiments, the binding of the antigen binding molecules of the present invention to a human adenosine receptor other than A2aR or A2aR from certain non-human mammal, e.g., murine A2aR is either undetectable or weak, as determined using an assay as set forth in Example 5, or a substantially similar assay.

The present invention includes A2aR antigen binding molecules, e.g., A2aR antibodies or antigen binding fragments thereof, which specifically bind to non-human primate A2aR, e.g., cynomolgus A2aR, expressed on a cell surface. In certain embodiment, the A2aR antigen binding molecules, e.g. A2aR antibodies or antigen binding fragments therefore, bind to a non-human primate A2aR with similar affinity, as determined using an assay as set forth in Example 7, or a substantially similar assay.

The present invention includes A2aR antigen binding molecules, e.g., A2aR antibodies or antigen binding fragments thereof, which specifically bind to endogenous human and non-human primate A2aR, e.g., cynomolgus A2aR, expressed on the surface of human or non-human primate immune cells. In certain embodiment, the A2aR antigen binding molecules, e.g. A2aR antibodies or antigen binding fragments therefore, bind to a human or non-human primate A2aR expressed on the surface of immune cells in periphery blood mononuclear cells (PBMC), as determined using an assay as set forth in Example 7, or a substantially similar assay.

4. Species Selectivity and Species Cross-Reactivity

The present invention, according to certain embodiments, provides antigen binding molecules that bind to human A2aR but not to A2aR from other species. The present invention also includes antigen binding molecules that bind to human A2aR and to A2aR from one or more non-human species, e.g., non-human primates.

According to certain exemplary embodiments of the invention, antigen binding molecules are provided which bind to human A2aR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee A2aR. For example, in a particular exemplary embodiment of the present invention, antigen binding molecules are provided comprising an antigen binding domain that binds human A2aR and non-human primate, e.g., cynomolgus A2aR.

III. THERAPEUTIC USE OF THE ANTI-A2AR ANTIGEN BINDING MOLECULES

The anti-A2aR antigen binding molecules of the present invention, including antibodies, antigen binding fragment thereof, and multispecific antibodies thereof, have numerous in vitro, in vivo and ex vivo utilities associated with enhancement of immune responses by blocking signaling by adenosine and other signaling pathways in the treatment of cancers. Without wishing to be bound by any theory, it is hypothesized that the antigen binding molecules of the present invention, e.g., anti-A2aR antibodies or antigen binding fragments thereof, binds to A2aR expressed on cell surface and inhibits the activities thereof, e.g., reducing the intracellular cAMP concentration as a result of inhibition of the A2aR activity. Accordingly, the antigen binding molecules of the invention (and therapeutic compositions comprising the same) are useful, inter alia, for treating any disease or disorder in which inhibition of A2aR activities, e.g., stimulation and/or activation of an immune response, would be beneficial. In view of the widespread expression of A2aR and the pleiotropic effects mediated by adenosine and A2aR, the anti-A2aR antigen binding molecules, e.g., antibodies or the antigen binding fragments thereof of the present invention may be used individually or in combination with a variety of active agents for treating a broad scope of diseases or disorders, including a variety of cancers.

Accordingly, the present invention provides a method of reducing the intracellular cAMP concentration in a cell, including contacting the cell with the antigen binding molecules of the present invention, e.g., anti-A2aR antibodies or antigen binding fragment thereof, with a cell. The reduction of intracellular cAMP concentration can be measure by a method as described in Example 4, or a substantially similar method. In certain embodiment, the methods of the invention reduce the concentration of the intracellular cAMP by at least about 10%, about 20%, about 50%, about 60%, about 70%, about 80%, about 90%, about 95%, or more, as compared to a baseline level.

In some embodiments, the antigen binding molecules, e.g., anti-A2aR antibodies or antigen binding fragments thereof, of the present invention are administered to cells in culture (in vitro) or to human subjects, in vivo or ex vivo, to enhance immunity in a variety of diseases. Accordingly, in one embodiment, a method for stimulating an immune response in a subject in need thereof includes administering to the subject an anti-A2aR antibody, antigen binding fragments thereof (e.g., anti-A2aR HCVRs and LCVRs) or multispecific anti-A2aR antibodies described herein, such that an immune response is enhanced, stimulated, up-regulated in the subject, for example, to inhibit tumor growth, stimulate anti-tumor T-cell immunity and/or stimulate anti-microbial immunity.

In one aspect, a method for enhancing an immune response (e.g., T cell response) in a subject includes the step of administering an anti-A2aR antibody described herein to a subject such that an immune response (e.g., T cell response) in the subject is enhanced. In some embodiments, the subject is a tumor-bearing subject and an immune response against the tumor is enhanced. A tumor may be a solid tumor or a liquid tumor, e.g., a hematological malignancy. In certain embodiments, the tumor is an immunogenic tumor. In other embodiments, a tumor is non-immunogenic. In other embodiments, the subject is pathogen-bearing subject in which an immune response against the pathogen is enhanced as a consequence of administering an anti-A2aR antibody described herein. The immune response includes, but is not limited to, a) promoting effector T cell function; b) reducing Treg activity; c) preventing Treg expansion; d) enhancing NK cell function; or e) promoting type 1 activation of antigen presenting cells.

In certain embodiments, the methods of the invention increase immune response by at least about 10%, about 20%, about 50%, about 60%, about 70%, about 80%, about 90%, about 1-fold, about 2-folds, about 4 folds, or more, as compared to a baseline level.

Preferred subjects include human patients in whom enhancement of an immune response would be desirable. The methods are particularly suitable for treating human patients having a disorder that can be treated by augmenting an immune response (e.g., the T-cell mediated immune response). The methods are particularly suitable for treatment of cancer, chronic infections and chronic inflammatory disease conditions. Preferably, the antibodies for use in the disclosed methods described herein are human or humanized antibodies.

In one embodiment, a method for inhibiting the growth of tumor cells in a subject comprises administering to the subject an anti-A2aR antibody described herein such that growth of the tumor is inhibited in the subject. The inhibition of tumor growth can be measured by various methods. The tumor growth can be measured using methods, e.g., as described in Talkington, A and Durrett, R, Estimating Tumor Growth Rates in vivo, Bull Math Biol., 2015 October: 77 (10): 1934-54, available at https://www.ncbi.nlm.nih.gov/pmc/articles/PMC4764475/, the entire contents of which are incorporated herein by reference. The inhibition of tumor growth can also be measured by the reduction of tumor size. In certain embodiment, the methods of the invention inhibit the tumor growth by at least about 10%, about 20%, about 50%, about 60%, about 70%, about 80%, about 90%, about 95%, or more, as compared to a baseline level.

In certain embodiment, the antigen binding molecules of the present invention, e.g., anti-A2aR antibodies or antigen binding fragments thereof, can be used in a method to reduce the immunosuppression in a tumor microenvironment. Such reduction can be measured by various methods. For example, the level immunosuppression in a tumor microenvironment can be measured by the presence and/or abundance of certain biomarkers in the tumor, such as PD-L1, CD73, IL-10, or TGF-β. The level of immunosuppression can also be measure by the ratio of CD8+ cytotoxic T cells to regulatory T ($T_{reg}$) cells in a tumor. In general, immunosuppression decreases the ration of CD8+ cytotoxic T cells to $T_{reg}$. In certain embodiments, the antigen binding molecules of the present invention, e.g., anti-A2aR antibodies or antigen binding fragments thereof, reduces the level of the immunosuppression in a tumor microenvironment by at least about 10%, about 20%, about 50%, about 60%, about 70%, about 80%, about 90%, about 95%, or more, as compared to a baseline level.

Also encompassed herein are methods for depleting $T_{reg}$ cells from the tumor microenvironment of a subject with a tumor, e.g., cancerous tumor, comprising administering to the subject a therapeutically effective amount of an anti-A2aR antibody described herein that comprises an Fc that stimulates depletion of $T_{reg}$ cells in the tumor microenvironment. An Fc may, for example, be an Fc with a suitable effector function or an enhanced effector function conferred by one or more activating Fc receptors.

In certain preferred embodiments, $T_{reg}$ depletion occurs without significant depletion or inhibition of $T_{eff}$ in the tumor microenvironment, and without significant depletion or inhibition of $T_{eff}$ cells and $T_{reg}$ cells outside of the tumor microenvironment. In certain embodiments, the subject has higher levels of A2aR on $T_{reg}$ cells than on $T_{eff}$ cells in the tumor microenvironment. In certain embodiments, anti-A2aR antibodies may deplete $T_{regs}$ in tumors and/or $T_{regs}$ in tumor infiltrating lymphocytes (TILs).

In certain preferred embodiments, the subject has a cell proliferative disease or cancer. Blocking of adenosine signaling through A2aR with the antigen binding molecules, e.g., anti-A2aR antibodies or antigen binding fragments thereof, of the present invention can enhance the immune response to cancerous cells in the patient. Therefore, the present invention provides methods for treating a subject having cancer, comprising administering to the subject an anti-A2aR antigen binding molecule, e.g., an antibody or the antigen binding fragment thereof, as described herein, such that the subject is treated, e.g., such that growth of a cancerous tumor is inhibited or reduced and/or that the tumor regresses. The anti-A2aR antibody can be used alone to inhibit the growth of cancerous tumors. Alternatively, the anti-A2aR antibody can be used in conjunction with targeting one or more other active agents, e.g., other anti-cancer targets, immunogenic agents, standard cancer treatments, or other antibodies, as described below. The antigen binding molecules of the present invention may be used to treat, e.g., primary and/or metastatic tumors. The present invention also includes methods for treating residual cancer in a subject. As used herein, the term "residual cancer" means the existence or persistence of one or more cancerous cells in a subject following treatment with an anti-cancer therapy.

Accordingly, in one aspect, a method of treating cancer includes the step of administering to a subject in need thereof, a therapeutically effective amount of an anti-A2aR antibody as described herein. Preferably, the antibody inhibits the activity of human anti-A2aR and includes one or more HCVRs and LCVRs described herein. Further, the anti-A2aR antigen binding molecules, e.g., antibodies for use in this method may include chimeric or humanized non-human anti-A2aR antibodies therefrom. The efficacy of treating a cancer can be measured by various methods. For example, the efficacy of treating a cancer can be measured by improvements in survival, or reduction in tumor size. In certain embodiments, the methods of the invention increase the efficacy of treating a cancer by at least about 10%, about 20%, about 50%, about 60%, about 70%, about 80%, about 90%, about 95%, about 1-fold, about 2 folds, about 4 folds, or more, as compared to a baseline level. The baseline level, as used in the context of cancer treatment, refers to the efficacy using a placebo if the A2aR antigen binding molecule of the invention is the sole therapeutic agent, or the efficacy using a placebo or an additional therapeutic agent if the A2aR antigen binding molecule of the invention is used in combination with the additional therapeutic agent.

Cancers whose growth may be inhibited using the antibodies of the invention include a broad variety of cancers, especially those that are unresponsive or that have a tendency to become unresponsive to monotherapies with other antibodies or chemotherapeutic agents. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CIVIL), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NEIL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

In some embodiments, treatment of a cancer patient with an anti-A2aR antibody and/or other active agents according to the present invention may lead to a long-term durable response relative to the current standard of care, including long term survival of at least 1, 2, 3, 4, 5, 10 or more years and/or recurrence free survival of at least 1, 2, 3, 4, 5, or 10 or more years. In certain embodiments, treatment of a cancer patient with an anti-A2aR antibody and/or other active agents according to the present invention prevents recurrence of cancer or delays recurrence of cancer by, e.g., 1, 2, 3, 4, 5, or 10 or more years. The anti-A2aR treatment can be used as a primary or secondary line of treatment.

Bone marrow transplantation is currently being used to treat a variety of tumors of hematopoietic origin. While graft versus host disease is a consequence of this treatment, A2aR inhibition may be used to increase the effectiveness of the donor engrafted tumor specific T cells by reducing graft vs. tumor responses.

In some embodiments, ex vivo activation in the presence of anti-A2aR antibodies and expansion of antigen specific T cells and adoptive transfer of these cells into recipients may be employed to stimulate antigen-specific T cells against cancers or viral infections by increasing the frequency and activity of the adoptively transferred T cells.

Suitable routes for administering the antigen binding molecules, e.g., anti-A2aR antibodies or antigen binding fragment thereof, of the present invention (e.g., humanized monoclonal antibodies, multi-specific antibodies, and immunoconjugates) described herein in vivo, ex vivo or in vitro are well known in the art and can be selected by those of ordinary skill. For example, the antibody compositions can be administered by parenteral injection (e.g., intravenous or subcutaneous). Suitable dosages will depend on the age and weight of the subject and the concentration and/or formulation of the antibody composition as further described below.

Increased A2aR activities has been implicated in neurodegenerative diseases. Accordingly, in certain embodiments, the present invention provides a method of treating a neurodegenerative disease, comprising administering the antigen binding molecules, e.g., anti-A2aR antibodies or antigen binding fragment thereof, of the present invention to a subject in need thereof, thereby treating the neurodegenerative disease.

IV. COMBINATION THERAPIES

In another aspect, the present invention provides therapeutic compositions and combination therapies for enhancing antigen-specific T cell responses, reducing immunosuppression, and/or reducing tumor growth in a subject. The present invention includes compositions and therapeutic formulations comprising any of the exemplary antigen binding molecules, e.g., herein in combination with one or more additional therapeutical agents, and methods of treatment comprising administering such combinations to subjects in need thereof. The term "additional therapeutic agent," as used herein, refers to any agents, which can be used to treat a disease or disorder, and any method of treatment for certain disease or disorder. For example, radiotherapy and surgery are deemed as "additional therapeutic agent" when they are used in combination with the antigen binding molecules, e.g., anti-A2aR antibodies or antigen binding fragment thereof, of the invention.

In certain embodiments, the additional therapeutic agent may be an A2aR antagonist that is different to the antigen binding molecule, e.g., anti-A2aR antibodies or antigen binding fragment thereof, of the present invention. Exemplary A2aR antagonist includes, but is not limited to AZD4635 (AstraZeneca), NIR178 (Novartis), AB928 (Arcus), CPI-444 (Corvus), EOS850 (iTeos), MK-3814 (Merck Sharp and Dolme).

In one embodiment, the additional therapeutic agent may be administered in the form of an antibody or antibody fragment(s) thereof, which are directed against another adenosine signaling pathway member, such as A1aR, A2bR, A3R, CD39, CD73 antagonist, or a combination thereof. Exemplary CD39 antagonists include, but are not limited to, Exemplary anti-CD39 antibodies and their antigen binding sites are described in U.S. Pat. Nos. 10,738,128, 10,662,253 and 10,556,959. Exemplary small molecule CD73 antagonists include, but are not limited to, AB421, MEDI9447, and BMS-986179. Exemplary anti-CD73 antibodies and their antigen binding sites are described in U.S. Pat. Nos. 10,766,966, 10,584,169, 10,556,968 and 10,167,343.

In some embodiments, the anti-A2aR antigen binding molecule, e.g., an anti-A2aR antibody or antigen binding fragment thereof, of the present invention is co-administered with one or more additional therapeutical agents in amount(s) effective in stimulating an immune response and/or apoptosis so as to further enhance, stimulate or upregulate an immune response and/or apoptosis in a subject. In addition, the one or more additional therapeutically active agents are administered prior to or subsequent to treatment with the anti-A2aR antibody.

In certain embodiments, the anti-A2aR antibodies described herein are administered in combination with or concurrently combined with one or other more other active agents, such as anti-cancer antibodies or polypeptides, chemotherapeutic agents, and radiotoxic agents. In other embodiments, the anti-A2aR antibodies described herein are administered in combination with or concurrently combined with a standard cancer treatment, such as surgery or radiation.

Co-administration of the anti-A2aR antibodies with these active agents or treatment modalities may address clinical deficiencies with regard to drug resistance, changes in the antigenicity of the tumor cells that render them unreactive with the antibody, and toxicities (by administering lower doses of one or more agents). A2aR inhibition is particularly well suited for use when combined with otherwise refractory chemotherapeutic regimes. In these instances, it may be possible to achieve enhanced efficacy, but to reduce the dose of chemotherapeutic reagent administered (Mokyr et al. (1998) Cancer Research 58: 5301-5304). The rationale for A2aR inhibition with radiation or chemotherapy is predicated on promoting cell death as a consequence of the cytotoxic action of radiation and most chemotherapeutic compounds, which can further result in increased levels of tumor antigen in the antigen presentation pathway. Other combination therapies that may act additively or synergistically with A2aR inhibition through cell death are surgery and hormone deprivation or inhibition. Each of these protocols further creates a source of tumor antigen in the host.

In some embodiments the anti-A2aR antibodies described herein are linked to another active agent in the form of an immuno-complex, immunoconjugate, or fusion protein. Alternatively, the anti-A2aR antibodies can be administered separate from the other active agent. In this case, the anti-A2aR antibodies and other antagonists can be administered before, after or concurrently with the other active agent or they may be co-administered with other known therapies, e.g., other anti-cancer agents, radiation etc. Accordingly, the present invention provides compositions and methods for providing two or more anti-cancer agents operating additively or synergistically via different mechanisms to beneficially provide both cytotoxic and immunoprotective effects in human cancer cells.

For example, in some embodiments, the anti-A2aR antibodies described herein may be combined with an anti-cancer agent, such an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue or combination thereof.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary anthracycline antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/odine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone deacetylase inhibitors include, but are not limited to, vorinostat (Zolinza), valproic acid, romidepsin, entinostat abexinostat, givinostat, and mocetinostat.

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary phosphatidyl-inositol-3 kinase (PI3K) inhibitors include wortmannin an irreversible inhibitor of PI3K, demethoxyviridin a derivative of wortmannin, LY294002, a reversible inhibitor of PI3K; BKM120 (Buparlisib); Idelalisib (a PI3K Delta inhibitor); duvelisib (IPI-145, an inhibitor of PI3K delta and gamma); alpelisib (BYL719), an alpha-specific PI3K inhibitor; TGR 1202 (previously known as RP5264), an oral PI3K delta inhibitor; and copanlisib (BAY 80-6946), an inhibitor PI3Kα,δ isoforms predominantly.

Exemplary Akt inhibitors include, but are not limited to miltefosine, AZD5363, GDC-0068, MK2206, Perifosine, RX-0201, PBI-05204, GSK2141795, and SR13668.

Exemplary MTOR inhibitors include, but are not limited to, everolimus (Afinitor) or temsirolimus (Torisel); rapamune, ridaforolimus; deforolimus (AP23573), AZD8055 (AstraZeneca), OSI-027 (OSI), INK-128, BEZ235, PI-103, Torin1, PP242, PP30, Ku-0063794, WAY-600, WYE-687, WYE-354, and CC-223.

Exemplary proteasomal inhibitors include, but are not limited to, bortezomib (PS-341), ixazomib (MLN 2238), MLN 9708, delanzomib (CEP-18770), carfilzomib (PR-171), YU101, oprozomib (ONX-0912), marizomib (NPI-0052), and disufiram.

Exemplary PARP inhibitors include, but are not limited to, olaparib, iniparib, velaparib, BMN-673, BSI-201, AG014699, ABT-888, GP121016, MK4827, INO-1001, CEP-9722, PJ-34, Tiq-A, Phen, PF-01367338 and combinations thereof.

Exemplary Ras/MAPK pathway inhibitors include, but are not limited to, trametinib, selumetinib, cobimetinib, CI-1040, PD0325901, AS703026, R04987655, R05068760, AZD6244, GSK1120212, TAK-733, U0126, MEK162, and GDC-0973.

Exemplary centrosome declustering agents include, but are not limited to, griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof; CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, and N2-benzyl-5-nitro-2-furamide.

Exemplary multi-kinase inhibitors include, but are not limited to, regorafenib; sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In certain embodiments, A2aR inhibition is carried out in combination with CD3 stimulation (e.g., by co-incubation with a cell expressing membrane CD3) before, at the same time, or after treatment with an anti-A2aR antibody. For example, in one embodiment, a method of enhancing an antigen-specific T cell response includes the step of contacting a T cell with an anti-A2aR antibody described herein, and a CD3-expressing cell, such that an antigen-specific T cell response is enhanced and the A2aR-mediated immunosuppression is reduced. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 and/or interferon-γ production by the antigen-specific T cell is enhanced.

In some embodiments, the anti-A2aR antibody described herein may also be used in combination with bispecific antibodies that target Fcα or Fcγ receptor-expressing effectors cells to tumor cells (see, e.g., U.S. Pat. Nos. 5,922,845 and 5,837,243). Such bispecific antibodies can be used to target two separate antigens. For example, anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the inhibition of A2aR. Alternatively, antigen may be delivered directly to DCs by the use of bispecific antibodies that bind to tumor antigen and a dendritic cell specific cell surface marker.

In all of the above methods, A2aR inhibition can be combined with other forms of immunotherapy such as cytokine treatment (e.g., interferons, GM-CSF, G-CSF, IL-2), or bispecific antibody therapy using two different binding specificities to provide enhanced presentation of tumor antigens.

In some embodiments, the additional therapeutic agent for use in any of the foregoing methods of treatment, uses of an antigen binding molecule or uses of a pharmaceutical composition is an immunostimulatory agent selected from (a) an agent that blocks signaling of an inhibitory receptor (immune checkpoint) of an immune cell or a ligand thereof (immune checkpoint inhibitor) or a nucleic acid encoding such agent; (b) an agonist to a stimulatory receptor of an immune cell or a nucleic acid encoding such agonist; (c) a cytokine or a nucleic acid encoding a cytokine; (d) an oncolytic virus or a nucleic acid encoding an oncolytic virus; (e) a T cell expressing a chimeric antigen receptor; (f) a bi- or multi-specific T cell directed antibody or a nucleic acid encoding such antibody; (g) an anti-TGF-β antibody or a nucleic acid encoding such antibody; (h) a TGF-β trap or a nucleic acid encoding such trap; (i) a vaccine to a cancer-associated antigen, including such antigen or a nucleic acid encoding such antigen, (j) a cell therapy, and (k) combinations thereof. In some embodiments, the additional therapeutic agent is an agent that blocks signaling of an inhibitory receptor of an immune cell or a ligand thereof or a nucleic acid encoding such agent, and the inhibitory receptor or ligand thereof is selected from PD-1, PD-L1, TIGIT, CTLA-4, PD-1, PD-L1, PD-L2, LAG-3, TIM-3, neuritin, BTLA, CECAM-1, CECAM-5, IL-1R8, VISTA, LAIR1, LILRB1, LILRB2, LILRB3, LILRB4, LILRB5, CD96, CD112R, CD 160, 2B4, TGFβ-R, KIR, NKG2A and combinations thereof. In some embodiments, the additional therapeutic agent is an agonist to a stimulatory receptor of an immune cell or a nucleic acid encoding such agonist, and the stimulatory receptor of an immune cell is selected from OX40, CD2, CD27, CDS, ICAM-1, LFA-1 (CD11a/CD18), ICOS (CD278), 4-1BB (CD 137), GITR, CD28, CD30, CD40, BAFFR, HVEM, CD7, LIGHT, KG2C, SLAMF7, NKG2C, NKG2D, NKp46, NKp80, CD 160, B7-H3, CD83 ligand, and combinations thereof. In some embodiments, the additional therapeutic agent is a cytokine or a nucleic acid encoding a cytokine selected from IL-2, IL-5, IL-7, IL-12, IL-15, IL-21, and combinations thereof. In some embodiments, the additional therapeutic agent is an oncolytic virus or a nucleic acid encoding an oncolytic virus selected from herpes simplex virus, vesicular stomatitis virus, adenovirus, Newcastle disease virus, vaccinia virus, a maraba virus, and combinations thereof. In some embodiments, the additional therapeutic agent is a cell therapy. A cell therapy may include a T cell, NK cell, or macrophage with a chimeric antigen receptor (CAR). In some embodiments, the cell therapy includes a bi- or multi-specific T cell directed antibody.

In certain embodiments, the present invention provides a method of treating a disease or disorder, e.g., cancer, in a subject. The method includes administering antigen binding molecules, e.g., anti-A2aR antibodies or antigen binding fragment thereof, of the present invention alone or in combination with a second one or more additional therapeutical agents into the subject, wherein the subject has previously received a treatment with a first one or more additional therapeutical agents. In certain embodiment, the treatment with the first one or more additional therapeutical agents may show low efficacy in treating the disease in the subject. For example, the treatment with the first one or more therapeutic agents may be treatment with an anti-PD1 antibody, to which the subject may show resistance. In some embodiments, the second one or more additional therapeutic agents are the same as the first one or more additional therapeutic agents. In some embodiments, the second one or more additional therapeutic agents are different to the first one or more additional therapeutic agents.

In certain embodiment, the immune checkpoint inhibitor is an antibody that interacts specifically with an immune checkpoint. In some embodiments, the additional therapeutic agent comprises an immunostimulatory agent. In some aspects, the immune checkpoint inhibitor is selected from an anti-PD-1 antibody (e.g., pembrolizumab or nivolumab), and anti-PD-L antibody (e.g., atezolizumab), an and -CTLA-4 antibody (e.g., ipilimumab), and combinations thereof. In some aspects, the immune checkpoint inhibitor is pembrolizumab. In some aspects, the immune checkpoint inhibitor is nivolumab. In some aspects, the immune checkpoint inhibitor is atezolizumab.

In some embodiments, the additional therapeutic agent is an agent that inhibits the interaction between PD-1 and PD-L1. In some aspects, the additional therapeutic agent that inhibits the interaction between PD-1 and PD-L1 is selected from an antibody, a peptidomimetic and a small molecule. In some aspects, the additional therapeutic agent that inhibits the interaction between PD-1 and PD-L1 is selected from pembrolizumab, nivolumab, atezolizumab, avelumab, durvalumab, BMS-936559, sulfamonomethoxine 1, and sulfamethizole 2.

In some embodiments, the anti-A2aR antibody is administered in combination with or concurrently with an immunogenic agent. Non-limiting examples of immunogenic agents include cancer cells, tumor vaccines, and purified tumor antigens (including recombinant proteins, peptides, and carbohydrate molecules); an oncolytic virus; cells transfected with genes encoding immune stimulating cytokines etc.

In certain embodiments, the anti-A2aR antibody is administered together with an antigen of interest or an antigen known to be present in the subject to be treated (e.g., a tumor-bearing or virus-bearing subject) to enhance antigen-specific immunity. When an anti-A2aR antibody is administered together with another agent, the two can be administered separately or simultaneously.

In certain embodiments, the anti-A2aR antibodies described herein may be used to enhance antigen-specific immune responses by co-administration of one or more of any of these antibodies with an antigen of interest (e.g., a vaccine). Accordingly, in one embodiment, a method for enhancing an immune response to an antigen in a subject, includes the steps of administering to the subject: (i) the antigen; and (ii) an A2aR-based antibody such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

In view of the benefits associated with synergistic active agent compositions, in certain embodiments, each of the anti-A2aR antibody and the other active agents are administered to a subject in need thereof at subtherapeutic doses relative to the doses used in monotherapies with the same.

In certain embodiments, A2aR inhibition is combined with standard cancer treatments (e.g., surgery, radiation, and chemotherapy). In these instances, it may be possible to reduce the dose of chemotherapeutic reagent administered. It is believed that the combined use of A2aR inhibition and chemotherapy can enhance apoptosis and increase tumor antigen presentation for cytotoxic immunity. Other synergistic combination therapies include A2aR inhibition in combination with radiation, surgery or hormone deprivation or inhibition. Each of these protocols creates a source of tumor antigen in the host.

The additional therapeutical agent may be administered prior to, concurrent with, or after the administration of an antigen binding molecule of the present invention; (for purposes of the present disclosure, such administration regimens are considered the administration of an antigen binding molecule "in combination with" an additional therapeutically active component).

The present invention includes pharmaceutical compositions in which an antigen binding molecule of the present invention is co-formulated with one or more of the additional therapeutical agents as described elsewhere herein.

V. NUCLEIC ACIDS AND HOST CELLS FOR EXPRESSING ANTI-A2AR ANTIBODIES

In another aspect, the present invention provides nucleic acids encoding the antigen binding molecules, e.g., anti-A2aR antibodies or antigen binding fragments thereof, of the present invention, and expression vectors comprising such nucleic acids. In some embodiments, nucleic acids encode an HCVR and/or LCVR fragment of an antibody or fragment in accordance with the embodiments described herein, or any of the other antibodies and antibody fragments described herein.

DNA encoding an antigen binding site in a monoclonal antibody can be isolated and sequenced from the hybridoma cells using conventional procedures (e.g., by using oligonucleotide probes that are capable of binding specifically to genes encoding the heavy and light chains of the monoclonal antibodies). Alternatively, amino acid sequences from immunoglobulins of interest may be determined by direct protein sequencing, and suitable encoding nucleotide sequences can be designed according to a universal codon table. In other cases, nucleotide and amino acid sequences of antigen binding sites or other immunoglobulin sequences, including constant regions, hinge regions and the like may be obtained from published sources well known in the art.

Expression vectors may be used to synthesize the antibodies of the present disclosure in cultured cells in vitro or they may be directly administered to a patient to express the antibodies of the present disclosure in vivo or ex vivo. As used herein, an "expression vector" refers to a viral or non-viral vector comprising a polynucleotide encoding one or more antibodies of the present disclosure in a form suitable for expression from the polynucleotide(s) in a host cell for antibody preparation purposes or for direct administration as a therapeutic agent.

A nucleic acid sequence is "operably linked" to another nucleic acid sequence when the former is placed into a functional relationship with the latter. For example, a DNA for a presequence or signal peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a signal peptide, contiguous and in reading phase. However, enhancers do not have to be contiguous. Linking is accomplished by ligation at convenient restriction sites. If such sites do not exist, synthetic oligonucleotide adaptors or linkers may be used in accordance with conventional practice.

Nucleic acid sequences for expressing the antibodies of the present disclosure typically include an N terminal signal peptide sequence, which is removed from the mature protein. Since the signal peptide sequences can affect the levels of expression, the polynucleotides may encode any one of a variety of different N-terminal signal peptide sequences. It will be appreciated by those skilled in the art that the design of the expression vector can depend on such factors as the choice of the host cell to be transformed, the level of expression of protein desired, and the like.

The above described "regulatory sequences" refer to DNA sequences necessary for the expression of an operably linked coding sequence in one or more host organisms. The term "regulatory sequences" is intended to include promoters, enhancers and other expression control elements (e.g., polyadenylation signals). Regulatory sequences include those which direct constitutive expression of a nucleotide sequence in many types of host cells or those which direct expression of the nucleotide sequence only in certain host cells (e.g., tissue-specific regulatory sequences). Expression vectors generally contain sequences for transcriptional termination, and may additionally contain one or more elements positively affecting mRNA stability.

The expression vector contains one or more transcriptional regulatory elements, including promoters and/or enhancers, for directing the expression of antibodies of the present disclosure. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be construed broadly so as to include e.g., transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. A promoter may contain a genomic fragment or it may contain a chimera of one or more TREs combined together.

Preferred promoters are those capable of directing high-level expression in a target cell of interest. The promoters may include constitutive promoters (e.g., HCMV, SV40, elongation factor-1α (EF-1α)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the antibody producing cell. Cell or tissue-specific transcriptional regulatory elements (TREs) can be incorporated into expression vectors to restrict expression to desired cell types. Pol III promoters (H1 or U6) are particularly useful for expressing shRNAs from which siRNAs are expressed. An expression vector may be designed to facilitate expression of the antibodies of the present disclosure in one or more cell types.

An siRNA is a double-stranded RNA that can be engineered to induce sequence-specific post-transcriptional gene silencing of mRNAs. Synthetically produced siRNAs structurally mimic the types of siRNAs normally processed in cells by the enzyme Dicer. When expressed from an expression vector, the expression vector is engineered to transcribe a short double-stranded hairpin-like RNA (shRNA) that is processed into a targeted siRNA inside the cell. Synthetic siRNAs and shRNAs may be designed using well known algorithms and synthesized using a conventional DNA/RNA synthesizer.

To co-express the individual chains of the antibodies of the present disclosure, a suitable splice donor and splice acceptor sequences may be incorporated for expressing both products. Alternatively, an internal ribosome binding sequence (IRES) or a 2A peptide sequence, may be employed for expressing multiple products from one promoter. An IRES provides a structure to which the ribosome can bind that does not need to be at the 5' end of the mRNA. It can therefore direct a ribosome to initiate translation at a second initiation codon within a mRNA, allowing more than one polypeptide to be produced from a single mRNA. A 2A peptide contains short sequences mediating co-translational self-cleavage of the peptides upstream and downstream from the 2A site, allowing production of two different proteins from a single transcript in equimolar amounts. CHYSEL is a non-limiting example of a 2A peptide, which causes a translating eukaryotic ribosome to release the growing polypeptide chain that it is synthesizing without dissociating from the mRNA. The ribosome continues translating, thereby producing a second polypeptide.

An expression vector may comprise a viral vector or a non-viral vector. A viral vector may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In some embodiments, expression of the antibody chains is under the control of the regulatory element such as a tissue specific or ubiquitous promoter. In some embodiments, a ubiquitous promoter such as a CMV promoter, CMV-chicken beta-actin hybrid (CAG) promoter, a tissue specific or tumor-specific promoter to control the expression of a particular antibody heavy or light chain or single-chain derivative therefrom.

Non-viral expression vectors can be utilized for non-viral gene transfer, either by direct injection of naked DNA or by encapsulating the antibody-encoding polynucleotides in liposomes, microparticles, microcapsules, virus-like particles, or erythrocyte ghosts. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

VI. METHODS FOR PRODUCING ANTI-A2AR ANTIBODIES

In another aspect, the present invention provides host cells transformed with the anti-A2aR HCVRs and/or LCVRs encoding nucleic acids or expression vectors. The host cells can be any bacterial or eukaryotic cell capable of expressing the anti-A2aR HCVRs and/or LCVRs encoding nucleic acids or expression vectors or any of the other co-administered antibodies or antagonists described herein.

In another aspect, a method of producing an antibody of the present disclosure comprises culturing a host cell transformed with one or anti-A2aR HCVRs and/or LCVRs encoding nucleic acids or expression vectors under conditions that allows production of the antibody or fragment, and purifying the antibody from the cell.

In a further aspect, the present invention provides a method for producing an antibody comprising culturing a cell transiently or stably expressing one or more constructs encoding one or more polypeptide chains in the antibody; and purifying the antibody from the cultured cells. Any cell capable of producing a functional antibody may be used. In preferred embodiments, the antibody-expressing cell is of eukaryotic or mammalian origin, preferably a human cell. Cells from various tissue cell types may be used to express the antibodies. In other embodiments, the cell is a yeast cell, an insect cell or a bacterial cell. Preferably, the antibody-producing cell is stably transformed with a vector expressing the antibody.

One or more expression vectors encoding the antibody heavy or light chains can be introduced into a cell by any conventional method, such as by naked DNA technique, cationic lipid-mediated transfection, polymer-mediated transfection, peptide-mediated transfection, virus-mediated infection, physical or chemical agents or treatments, electroporation, etc. In addition, cells may be transfected with one or more expression vectors for expressing the antibody along with a selectable marker facilitating selection of stably transformed clones expressing the antibody. The antibodies produced by such cells may be collected and/or purified according to techniques known in the art, such as by centrifugation, chromatography, etc.

Examples of suitable selectable markers for mammalian cells include dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR− cells and mouse LTV cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Exemplary antibody-expressing cells include human Jurkat, human embryonic kidney (HEK) 293, Chinese hamster ovary (CHO) cells, mouse WEHI fibrosarcoma cells, as well as unicellular protozoan species, such as *Leishmania tarentolae*. In addition, stably transformed, antibody producing cell lines may be produced using primary cells immortalized with c-myc or other immortalizing agents.

In one embodiment, the cell line comprises a stably transformed *Leishmania* cell line, such as *Leishmania tarentolae*. *Leishmania* are known to provide a robust, fast-growing unicellular host for high level expression of eukaryotic proteins exhibiting mammalian-type glycosylation patterns. A commercially available *Leishmania* eukaryotic expression kit is available (Jena Bioscience GmbH, Jena, Germany).

In some embodiments, the cell lines express at least 1 mg, at least 2 mg, at least 5 mg, at least 10 mg, at least 20 mg, at least 50 mg, or at least 100 mg of the antibody/liter of culture.

The antibodies in the present invention may be isolated from antibody expressing cells following culture and maintenance in any appropriate culture medium, such as RPMI, DMEM, and AIM V®. The antibodies can be purified using conventional protein purification methodologies (e.g., affinity purification, chromatography, etc.), including the use of Protein-A or Protein-G immunoaffinity purification. In some embodiments, antibodies are engineered for secretion into culture supernatants for isolation therefrom.

VII. PHARMACEUTICAL COMPOSITIONS AND DOSING METHODOLOGIES

In one aspect, a pharmaceutical composition of the present invention includes an antigen binding molecule, e.g., an A2aR antibody or antigen binding fragment(s) thereof as described herein in combination with a pharmaceutically acceptable carrier. In other embodiments, the A2aR antibody or antigen binding fragment(s) thereof are administered in combination with a pharmaceutically acceptable carrier. Anti-A2aR compositions may include one or more different antibodies, one or more multispecific antibodies, one or more fusion proteins, one or more immunoconjugates, or a combination thereof as described herein.

The present invention provides pharmaceutical compositions comprising the antigen binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen binding molecule administered to a patient may vary depending upon the age and the size of the patient, target disease, conditions, route of administration, and the like. The preferred dose is typically calculated according to body weight or body surface area. When a bispecific antigen binding molecule of the present invention is used for therapeutic purposes in an adult patient, it may be advantageous to intravenously administer the bispecific antigen binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

In another aspect, a method for treating a cell proliferative disorder, such as cancer, a chronic infection, or an immunologically compromised disease state includes administering to a subject in need thereof a pharmaceutical composition containing an anti-A2aR antibody or antigen binding fragment as described herein in combination with a pharmaceutically acceptable carrier. In some embodiments, the method restores, potentiates or enhances the activity of lymphocytes in a subject in need thereof. In certain preferred embodiments, the antibody or fragment is a human or humanized anti-A2aR antibody that reduces or abrogates signaling through the A2aR.

In some embodiments, administration of the pharmaceutical composition increases the activity of lymphocytes (e.g., T cells) in patients having a disease in which increased lymphocyte activity is beneficial or which is caused or characterized by immunosuppression, immunosuppressive cells, or, e.g., adenosine generated by CD4 T cells, CD8 T cells, B cells). The methods described herein are particularly useful, e.g., in patients having a solid tumor in which it is suspected the tumor microenvironment (and adenosine production therein) may contribute to the lack of recognition by the immune system (immune escape). The tumor may, for example, be characterized by A2aR-expressing (or overexpressing) immune cells, e.g., CD4 T cells, CD8 T cells, T-regs, B cells.

In certain embodiments, the methods and compositions are utilized for the treatment of a variety of cancers and other proliferative diseases. Because these methods serve to reduce adenosine levels, which can inhibit the anti-tumor activity of lymphocytes, they are applicable to a very broad range of cancers, particularly solid tumors where adenosine in the tumor microenvironment is known to suppress anti-tumor immune responses.

Non-limiting cancers for treatment using the antigen binding molecules, e.g., anti-A2aR antibodies or antigen binding fragments thereof, of the present invention include, for example, liver cancer, bone cancer, pancreatic cancer, skin cancer, cancer of the head or neck, breast cancer, lung cancer, non-small cell lung cancer (NSCLC), castrate resistant prostate cancer (CRPC), melanoma, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, or any combination of these cancers. The present disclosure is also applicable to treatment of metastatic cancers. Patients can be tested or selected for one or more of the above-described clinical attributes prior to, during or after treatment.

In one embodiment, the anti-A2aR antibody is administered an amount effective to achieve and/or maintain in an individual (e.g., for 1, 2, 3, 4 weeks, and/or until the subsequent administration of antigen binding compound) a blood concentration of at least the $EC_{50}$, optionally the $EC_{70}$, optionally substantially the $EC_{100}$, for neutralization of the enzymatic activity of A2aR. In one embodiment, the active amount of anti-A2aR antibody is an amount effective to achieve the $EC_{50}$, optionally the $EC_{70}$, optionally substantially the $EC_{100}$, for neutralization of the enzymatic activity of A2aR in an extravascular tissue of an individual. In one embodiment, the active amount of anti-A2aR antibody is an amount effective to achieve (or maintain) in an individual the $EC_{50}$, optionally the $EC_{70}$, optionally substantially the $EC_{100}$, for inhibition of neutralize the enzymatic activity of A2aR.

Optionally, in one embodiment, in contrast to some antibodies that are directed to the depletion of A2aR-expressing tumor cells by ADCC (which, e.g., can provide full efficacy at concentrations equal or substantially lower than that which provides receptor saturation), the anti-A2aR antibody is a mainly blocker (no substantial Fcγ receptor-mediated activity) and is administered in an amount effective to neutralize the enzymatic activity of A2aR for a desired period of time, e.g., 1 week, 2 weeks, a month, until the next successive administration of anti-A2aR antibody.

In one embodiment, the anti-A2aR antibody is administered in an amount effective to achieve and/or maintain (e.g., for 1, 2, 3, 4 weeks, and/or until the subsequent administration of anti-A2aR antibody) in an individual a blood concentration of at least the $EC_{50}$, optionally the $EC_{70}$, optionally substantially the $EC_{100}$, for inhibition of A2aR-mediated catabolism of AMP to adenosine. In one embodiment, the amount of anti-A2aR antibody is an amount effective to achieve (or maintain) the $EC_{50}$, optionally the $EC_{70}$, optionally substantially the $EC_{100}$, for inhibition of A2aR-mediated catabolism of AMP to adenosine in an extravascular tissue of an individual.

In one embodiment, provided is a method for treating or preventing cancer in an individual, the method comprising administering to an individual having disease an anti-A2aR antibody in an amount that achieves or maintains for a specified period of time a concentration in circulation, optionally in an extravascular tissue of interest (e.g., the tumor or tumor environment), that is higher than the concentration required for 50%, 70%, or full (e.g., 90%) receptor saturation A2aR-expressing cells in circulation (for example as assessed in PBMC). Optionally the concentration achieved is at least 20%, 50% or 100% higher than the concentration required for the specified receptor saturation.

In one embodiment, provided is a method for treating or preventing cancer in an individual, the method comprising administering to the individual an anti-A2aR antibody in an amount that achieves or maintains for a specified period of time a concentration in circulation, optionally in an extravascular tissue of interest (e.g., the tumor or tumor environment), that is higher than the $EC_{50}$, optionally $EC_{70}$ or optionally $EC_{100}$, for binding to A2aR-expressing cells. Optionally the concentration achieved is at least 20%, 50% or 100% higher than the $EC_{50}$, optionally $EC_{70}$ or optionally $EC_{100}$, for binding to A2aR-expressing cells.

In any embodiment, the antibody can for example have an $EC_{50}$, optionally $EC_{70}$ or optionally $EC_{100}$, for binding to A2aR-expressing cells in human PBMC of between 0.5-100 ng/ml, optionally 1-100 ng/ml, optionally 30-100 ng/ml, e.g., about 30-90 ng/ml. For example, the $EC_{50}$ may be about 30, 37, 39, 43, 57, 58, 61, 62, 90, 95, 143 ng/ml.

The $EC_{50}$ for neutralization of the enzymatic activity of A2aR with the anti-A2aR antibody can be for example between about 0.01 μg/ml and 1 μg/ml, optionally between 0.1 μg/ml and 10 μg/ml, optionally between 0.1 μg/ml and 1 μg/ml. For example, the $EC_{50}$ may be about 0.1 μg/ml, about 0.2 μg/ml or about 0.3 μg/ml. Thus, an amount of this anti-A2aR antibody is for example administered so at to achieve and/or maintain a blood concentration of at least 0.1 μg/ml, optionally at least 0.2 μg/ml, optionally at least 1 μg/ml, or optionally at least 2 μg/ml.

When tissues outside of the vasculature are targeted (the tumor environment, e.g., in the treatment of solid tumors), an approximately 10-fold higher dose is typically believed to be needed, compared to the dose that provides the corresponding concentration in circulation. An amount of anti-A2aR antibody administered so at to achieve (and/or maintain) a concentration in circulation (blood) of about 1 μg/ml, 2 μg/ml, 10 μg/ml, or 20 μg/ml is expected to achieve (and/or maintain) an extravascular tissue (e.g., tumor tissue) concentration of about 0.1 μg/ml, 0.2 μg/ml, 1 μg/ml, 2 μg/ml, respectively.

In one embodiment, an anti-A2aR antibody is for example administered in an amount so at to achieve and/or maintain a tissue (e.g., tumor environment) concentration of at least 0.1 μg/ml, optionally at least 0.2 μg/ml, optionally at least 1 μg/ml, or optionally at least 2 μg/ml. The antibody can for example be administered in an amount to achieve and/or maintained a blood concentration of at least about 1 μg/ml, 2 μg/ml, 10 μg/ml, or 20 μg/ml, e.g., between 1-100 μg/ml, 10-100 μg/ml, 1-50 μg/ml, 1-20 μg/ml, or 1-10 μg/ml. The amount administered can be adjusted to as to provide for maintenance of the desired concentration for the duration of a specified period of time following administration (e.g., 1, 2, 3, 4 weeks, etc.).

In some embodiments, an amount of anti-A2aR antibody is administered so as to obtain a concentration in blood (serum) or an extravascular tissue (e.g., tumor environment) that corresponds to at least the $EC_{70}$ or the $EC_{100}$ for neutralization of the enzymatic activity of A2aR. The antibody can for example be administered in an amount to achieve and/or maintained a blood concentration or an extravascular tissue (e.g., tumor environment) of at least about 1 μg/ml, 2 μg/ml, 10 μg/ml, or 20 μg/ml.

$EC_{50}$, $EC_{70}$ and $EC_{100}$ values for a given A2aR antibody can be assessed for example in a cellular assay for neutralization of the enzymatic activity of A2aR. "$EC_{50}$" with respect to neutralization of the enzymatic activity of A2aR, refers to the concentration of anti-A2aR antibody which produces 50% of its maximum response or effect with respect to neutralization of the enzymatic activity). "$EC_{70}$" with respect to neutralization of the enzymatic activity of A2aR, refers to the concentration of anti-A2aR antibody which produces 70% of its maximum response or effect. "$EC_{100}$" with respect to neutralization of the enzymatic activity of A2aR, refers to the efficient concentration of anti-A2aR antibody which produces its maximum response or effect with respect to such neutralization of the enzymatic activity. In certain embodiments and depending on the context, $EC_{50}$, $EC_{70}$, or $EC_{100}$, may be referred to as $IC_{50}$, $IC_{70}$, or $IC_{100}$, respectively, to reflect that the antigen binding molecule, e.g., the anti-A2aR antibody or the antigen binding fragment thereof inhibits the activities of the A2aR. $IC_{xx}$ refers to the concentration of a drug that is needed to inhibit a biological process by xx %.

In some embodiments, particularly for the treatment of solid tumors, the concentration achieved is designed to lead to a concentration in tissues (outside of the vasculature, e.g., in the tumor or tumor environment) that corresponds to at least the $EC_{50}$ for neutralization of the enzymatic activity, optionally at about, or at least about, the $EC_{100}$.

In one embodiment, the amount of anti-A2aR antibody is between 1 and 20 mg/kg body weight. In one embodiment, the amount is administered to an individual weekly, every two weeks, monthly or every two months.

In one embodiment, a method of treating a cancer in a subject in need thereof, includes administering to the individual an effective amount of an anti-A2aR antibody of the disclosure for at least one administration cycle (optionally at least 2, 3, 4 or more administration cycles), wherein the cycle is a period of eight weeks or less, wherein for each of the at least one cycles, one, two, three or four doses of the anti-A2aR antibody are administered at a dose of 1-20 mg/kg body weight. In one embodiment, the anti-A2aR antibody is administered by intravenous infusion.

Suitable treatment protocols for treating e.g., a human subject include, for example, administering to the patient an amount as disclosed herein of an anti-A2aR antibody, wherein the method includes at least one administration cycle in which at least one dose of the anti-A2aR antibody is administered. Optionally, at least 2, 3, 4, 5, 6, 7 or 8 doses of the anti-A2aR antibody are administered. In one embodiment, the administration cycle is between 2 weeks and 8 weeks.

In one embodiment, a method for treating or preventing a disease (e.g., a cancer, a solid tumor, a hematological tumor) in an individual, includes administering to the individual an anti-A2aR antibody that neutralizes the enzymatic activity of A2aR for at least one administration cycle, the administration cycle comprising at least a first and second (and optionally a 3rd, 4th, 5th 6th, 7th and/or 8th or further) administration of the anti-A2aR antibody, wherein the anti-A2aR antibody is administered in an amount effective to achieve, or to maintain between two successive administrations, a blood (serum) concentration of anti-A2aR antibody of at least 0.1 μg/ml, at least 0.2 μg/ml, at least 1 μg/ml, at least 2 μg/ml, at least 10 μg/ml, at least 20 μg/ml, between 1-100 μg/ml, between 1-50 μg/ml, between 1-20 μg/ml, between 1-10 μg/ml or a range between any of the aforementioned concentrations.

In one embodiment, a specified continuous blood concentration is maintained, wherein the blood concentration does not drop substantially below the specified blood concentration for the duration of the specified time period (e.g., between two administrations of antibody, number of weeks, 1 week, 2 weeks, 3 weeks, 4 weeks). In other words, although the blood concentration can vary during the specified time period, the specified blood concentration maintained represents a minimum or "trough" concentration.

In one embodiment, a therapeutically active amount of an anti-A2aR antibody is an amount of such antibody capable of providing (at least) the $EC_{50}$ concentration, optionally the $EC_{70}$ concentration optionally the $EC_{100}$ concentration, in blood and/or in a tissue for neutralization of the enzymatic activity of A2aR for a period of at least about 1 week, about 2 weeks, or about one month, following administration of the antibody.

Prior to or during a course of treatment with an anti-A2aR antibody of the disclosure, expression levels of A2aR, CD39 and/or CD73 in cells; percentages of A2aR-expressing, CD39-expressing, and/or CD73-expressing cells; and/or levels of adenosine, ADP and/or AMP can be assessed within and/or adjacent to a patient's tumor to assess whether the patient is suitable for treatment and is likely to respond to treatment. Increased levels or expression of the foregoing may indicate an individual is suitable for treatment with (e.g., likely to benefit from) an anti-A2aR antibody of the present disclosure.

In some embodiments, assessing the expression levels of A2aR, CD39, and/or CD73 and the concentrations of adenosine, ADP and/or AMP within and/or adjacent to a patient's tumor the tissue sample includes the step of obtaining from a subject a biological sample of a human tissue selected from the group consisting of tissue from a cancer patient, e.g., cancer tissue, tissue proximal to or at the periphery of a cancer, cancer adjacent tissue, adjacent non-tumorous tissue or normal adjacent tissue, and expression levels of A2aR, CD39, and/or CD73 and the concentrations of adenosine, ADP and/or AMP within the tissue. The expression levels or nucleotide concentrations from the patient can be comparing the level to a reference level, e.g., corresponding to a healthy individual.

Decreased levels of adenosine, ADP and/or AMP compared following an administration (or dosing of antibody) compared to levels prior to treatment (or dosing of antibody) may indicate an individual is benefitting from treatment with an anti-A2aR antibody of the disclosure (including but not limited to an antibody that inhibits substrate-bound A2aR). Optionally, if a patient is benefiting from treatment with the anti-A2aR antibody, methods can further include administering a further dose of the anti-A2aR antibody to the patient (e.g., continuing treatment) alone or in combination with another active agent.

In view of the foregoing, in certain embodiments, the method includes the steps of: (a) determining the expression levels of A2aR, CD39, and/or CD73 and/or the concentrations of adenosine, ADP and/or AMP in the tumor environment, optionally within the tumor and/or within adjacent tissue, and upon a determination that tumor environment exhibits levels of A2aR, CD39, CD73, adenosine, ADP and/or AMP that is/are increased compared to their corresponding reference level(s), (b) administering to the individual an anti-A2aR antibody.

In certain embodiments, determining the levels of A2aR, CD39, CD73, adenosine, ADP and/or AMP within the tumor environment includes the step of obtaining from the subject a biological containing cancer tissue and/or tissue proximal to or at the periphery of a cancer (e.g., cancer adjacent tissue, adjacent non-tumorous tissue or normal adjacent tissue), and detecting levels and/or relative percentages of A2aR– CD39– and/or CD73-expressing cells and/or levels of adenosine, ADP and/or AMP. A2aR– CD39– and/or CD73-expressing cells may include, for example, tumor cells, CD4 T cells, CD8 T cells, B cells, and combinations thereof. Expression levels of A2aR, CD39, CD73 may be determined by evaluating their mRNA expression (by e.g., RT-PCR) or polypeptide expression (by e.g., western blotting, immunofluorescent staining) compared to a reference level corresponding to a healthy subject or compared to a reference level before treatment using techniques well known to those of ordinary skill in the art.

A subject with cancer can be treated with the anti-A2aR antibody with or without assessing the A2aR, CD39, CD73, adenosine, ADP and/or AMP levels in the tumor microenvironment (e.g., on tumor cells, CD4 T cells, CD8 T cells, B cells).

A determination that a biological sample includes cells overexpressing A2aR, CD39 and/or CD73, and/or containing high concentrations of adenosine, ADP and/or AMP compared to a reference, indicates that the subject has a cancer that may benefit from treatment with an agent that inhibits A2aR. In some embodiments, the term "overexpressed" is used with reference to an A2aR, CD39 and/or CD73 polypeptide that is expressed in a substantial number of cells taken from a given patient, for example, on at least 10%, at least 20%, at least 30%, at least 40%, at least 50%, at least 60%, at least 70%, at least 80%, at least 90%, at least 95% or more of the tumor cells or lymphocytes taken from a subject.

In one embodiment, a method for the treatment or prevention of a cancer in an subject in need thereof includes the steps of: (a) detecting the percentage of cells and/or extent of expression corresponding to A2aR, CD39 and/or CD73 within the tumor environment, optionally within the tumor and/or within adjacent tissue, and upon a determination that the tumor environment includes cells overexpressing A2aR, CD39 and/or CD73, optionally at level(s) that are increased compared to suitable reference levels, (b) administering to the subject an anti-A2aR antibody. In one embodiment, the cells are tumor cells. In another embodiment, the cells within the tumor environment, tumor and/or adjacent tissue are non-malignant immune cells, e.g., T cells.

In some embodiments, determining the extent of A2aR, CD39 and/or CD73 expression within the tumor environment includes the step of obtaining from the individual a biological sample that comprises cancer tissue and/or tissue proximal to or at the periphery of a cancer (e.g., cancer adjacent tissue, adjacent non-tumorous tissue or normal adjacent tissue), contacting the cells with an antibody that binds an A2aR polypeptide, CD39 polypeptide and/or CD73 polypeptide and detecting the percentage of cells and/or the extent of expression corresponding to the A2aR, CD39 and/or CD73. In certain embodiments, expression of A2aR, CD39 and/or CD73 is evaluated by their cell surface expression using an immunohistochemistry assay.

The antibody compositions may be used in as monotherapy or combined treatments with one or more other therapeutic agents, including agents normally utilized for the particular therapeutic purpose for which the antibody is being administered. See "Combination therapies" above. The additional therapeutic agent will normally be administered in amounts and treatment regimens typically used for that agent in a monotherapy for the particular disease or condition being treated. Such therapeutic agents include, but are not limited to anti-cancer agents and chemotherapeutic agents.

As described above, methods for using the pharmaceutical compositions described herein include the step of administering to a subject in need thereof an effective amount of the pharmaceutical composition according to the present disclosure.

Any suitable route or mode of administration can be employed for providing the patient with a therapeutically or prophylactically effective dose of the antibody. Exemplary routes or modes of administration include parenteral (e.g., intravenous, intraarterial, intramuscular, subcutaneous, intratumoral), oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising an anti-A2aR antibody in accordance with the present disclosure may be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions may comprise suitable solid or gel phase carriers or excipients. Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agents.

In certain preferred embodiments, the therapeutically active agents can be incorporated into a pharmaceutical composition suitable for parenteral administration. Pharmaceutical composition for parenteral administration may be formulated by injection e.g., by bolus injection or continuous infusion.

Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

Therapeutic agent preparations can be lyophilized and stored as sterile powders, preferably under vacuum, and then reconstituted in bacteriostatic water (containing, for example, benzyl alcohol preservative) or in sterile water prior to injection. The therapeutic agents in the pharmaceutical compositions may be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of an antibody or active agent may vary depending on the condition to be treated, the severity and course of the condition, the mode of administration, whether the antibody or agent is administered for preventive or therapeutic purposes, the bioavailability of the particular agent(s), the ability of the antibody to elicit a desired response in the individual, previous therapy, the age, weight and sex of the patient, the patient's clinical history and response to the antibody, the type of the antibody used, discretion of the attending physician, etc. A therapeutically effective amount is also one in which any toxic or detrimental effects of the recombinant vector is outweighed by the therapeutically beneficial effects. A "prophylactically effective amount" refers to an amount effective, at dosages and for periods of time necessary, to achieve the desired prophylactic result.

Preferably, the polypeptide domains utilized in the antibodies or other active agents described herein are derived from the same host in which they are to be administered in order to reduce inflammatory responses against the administered therapeutic agents. As suggested above, the therapeutic agent(s) are suitably administered to the subject at one time or over a series of treatments and may be administered to the patient at any time from diagnosis onwards. The A2aR antibody may be administered as the sole treatment or in conjunction with other active agents or therapies useful in treating the condition in question.

As a general proposition, a therapeutically effective amount or prophylactically effective amount of the A2aR antibody (or other active agent) will be administered in a range from about 1 ng/kg body weight/day to about 100 mg/kg body weight/day whether by one or more administrations. In a particular embodiment, each A2aR antibody or active agent is administered in the range of from about 1 ng/kg body weight/day to about 10 mg/kg body weight/day, about 1 ng/kg body weight/day to about 1 mg/kg body weight/day, about 1 ng/kg body weight/day to about 100 μg/kg body weight/day, about 1 ng/kg body weight/day to about 10 μg/kg body weight/day, about 1 ng/kg body weight/day to about 1 μg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 μg/kg body weight/day, about 10 ng/kg body weight/day to about 10 μg/kg body weight/day, about 10 ng/kg body weight/day to about 1 μg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 μg/kg body weight/day, about 100 ng/kg body weight/day to about 10 μg/kg body weight/day, about 100 ng/kg body weight/day to about 1 μg/kg body weight/day, about 1 μg/kg body weight/day to about 100 mg/kg body weight/day, about 1 μg/kg body weight/day to about 10 mg/kg body weight/day, about 1 μg/kg body weight/day to about 1 mg/kg body weight/day, about 1 μg/kg body weight/day to about 100 μg/kg body weight/day, about 1 μg/kg body weight/day to about 10 g/kg body weight/day, about 10 μg/kg body weight/day to about 100 mg/kg body weight/day, about g/kg body weight/day to about 10 mg/kg body weight/day, about 10 μg/kg body weight/day to about 1 mg/kg body weight/day, about 10 μg/kg body weight/day to about 100 μg/kg body weight/day, about 100 μg/kg body weight/day to about 100 mg/kg body weight/day, about 100 μg/kg body weight/day to about 10 mg/kg body weight/day, about 100 μg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In other embodiments, the A2aR antibody and/or active agent is administered at a dose of 500 g to 20 g every three days, or 25 mg/kg body weight every three days.

In other embodiments, each A2aR antibody and/or active agent is administered in the range of about 10 ng to about 100 ng per individual administration, about 10 ng to about 1 μg per individual administration, about 10 ng to about 10 μg per individual administration, about 10 ng to about 100 g per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 μg per individual administration, about 100 ng to about 10 g per individual administration, about 100 ng to about 100 μg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 μg to about 10 μg per individual administration, about 1 μg to about 100 μg per individual administration, about 1 μg to about 1 mg per individual administration, about 1 μg to about 10 mg per individual administration, about 1 μg to about 100 mg per individual administration, about 1 μg to about 1000 mg per injection, about 1 μg to about 10,000 mg per individual administration, about 10 μg to about 100 μg per individual administration, about 10 μg to about 1 mg per individual administration, about g to about 10 mg per individual administration, about 10 μg to about 100 mg per individual administration, about 10 μg to about 1000 mg per injection, about 10 μg to about 10,000 mg per individual administration, about 100 μg to about 1 mg per individual administration, about 100 μg to about 10 mg per individual administration, about 100 μg to about 100 mg per individual administration, about 100 μg to about 1000 mg per injection, about 100 μg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The antibodies of the present disclosure may be administered daily, every 2, 3, 4, 5, 6 or 7 days, or every 1, 2, 3 or 4 weeks.

In other particular embodiments, the amount of each A2aR antibody or active agent may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day.

In certain embodiments, the coding sequences for the A2aR antibody and/or other active agent(s) are incorporated into a suitable expression vector (e.g., viral or non-viral vector) for expressing an effective amount of the A2aR antibody or other active agent in a subject in need of treatment in accordance with the above-described methods. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Dosages can be tested in one or several art-accepted animal models suitable for any particular cell proliferative disorder or immune-compromised disease state.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

VIII. DIAGNOSTIC USES OF THE ANTIBODIES

The antigen binding molecules, e.g., antibodies or the antigen binding fragment thereof, of the present invention may also be used to detect and/or measure human or cynomolgus A2aR, or human or cynomolgus A2aR expressing cells in a sample, e.g., for diagnostic purposes. For example, an anti-A2aR antibody, or the antigen binding fragment thereof, may be used to diagnose a condition or disease characterized by aberrant expression (e.g., over-expression, under-expression, lack of expression, etc.) of A2aR. Exemplary diagnostic assays for A2aR, e.g., contacting a sample, obtained from a patient, with an antibody of the invention, wherein the antibody is labeled with a detectable label or reporter molecule. Alternatively, an unlabeled antibody can be used in diagnostic applications in combination with a secondary antibody which is itself detectably labeled. The detectable label or reporter molecule can be a radioisotope, such as $^{3}H$, $^{14}C$, $^{18}F$, $^{32}p$, $^{35}S$, or $^{125}I$; a fluorescent or chemiluminescent moiety such as fluorescein isothiocyanate, or rhodamine; or an enzyme such as alkaline phosphatase, betagalactosidase, horseradish peroxidase, or luciferase. Specific exemplary assays that can be used to detect or measure A2aR in a sample include enzyme-linked immunosorbent assay (ELISA), radioimmunoassay (RIA), and fluorescence-activated cell sorting (FACS). Samples that can be used in A2aR diagnostic assays according to the present invention include any tissue or fluid sample obtainable from a patient which contains detectable quantities of A2aR protein, or fragments thereof, under normal or pathological conditions. Generally, levels of A2aR in a particular sample obtained from a healthy patient (e.g., a patient not afflicted with a disease or condition associated with abnormal A2aR levels or activity) will be measured to initially establish a baseline, or standard, level of A2aR. This baseline level of A2aR can then be compared against the levels of A2aR measured in samples obtained from individuals suspected of having a A2aR related disease or condition.

Moreover, the anti-A2aR antibodies described herein can be used to purify human A2aR via immunoaffinity purification.

IX. KITS

Any of the compositions described herein, e.g., the anti-A2aR antigen binding molecules of the present invention, and/or the additional therapeutic agent, may be comprised in a kit. In a non-limiting example, the kit comprises an antigen binding molecule, e.g., an antibody or antigen binding fragment thereof. In certain embodiments, the kit further includes an additional therapeutic agent described herein.

The kit may further include reagents or instructions for treating a disease or disorder. It may also include one or more buffers.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also generally contains a second, third or other additional container into which the additional components may be separately placed. The kits may also comprise a second container means for containing a sterile, pharmaceutically acceptable buffer and/or other diluent. However, various combinations of components may be comprised in a vial. The kits of the present invention also typically include a means for containing the compositions of the invention, e.g., the anti-A2aR antigen binding molecules and/or the additional therapeutic agent, and any other reagent containers in close confinement for commercial sale.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The present invention is further illustrated by the following examples which should not be construed as limiting. The contents of all references, patents and published patent applications cited throughout this application, as well as the Figures and Tables are incorporated herein by reference.

EXAMPLES

Example 1: Generation of Anti-A2aR Monoclonal Antibodies

Immunization of Mice

Six to eight (6-8) weeks old C57BL/6 mice were immunized by injecting the plasmid encoding human A2aR (human A2aR: SEQ ID No: 50) into the mice under an IACUC approved protocol. Briefly, the human A2aR gene insert was cloned into the modified expression vector. The DNA plasmid was then produced from *Escherichia coli* (HB101 strain) with a Mega purification kit (Qiagen, Cat. 12981). Six to eight weeks old C57/B6 mice (Taconic Farms) each received multiple rounds of immunizations with human A2aR-encoding plasmids delivered by either Gene gun (Bio-rad) system or Intradermal (ID) injection followed by Electroporation (BTX-Harvard Apparatus). Serum samples were taken prior to the first immunization and 7 days after the last immunization.

Serum titration was performed using Fluorescence-Activated Cell Sorting (FACS) pursuant to standard procedures. Human A2aR-expressing Expi293 cells were first added to 96-well plate ($1\times10^{5}$ cells per well), 50 μl of serial diluted serum (1:50, 1;150, 1:450, 1:1350, 1:4053, 1:12150) from each individual mouse was incubated with cells for 30 min. on ice. After washing with FACS buffer (2% Fetal bovine serum, 2 mM EDTA in PBS), Alex Fluor 647-conjugated anti mouse IgG was added and incubated for 20 min on ice. Cells were resuspending with 100 μl FACS buffer after two times wash and ready for FACS analysis (BD LSR II Flow Cytometer, HTS). As shown in FIG. 1, several mice showed strong A2aR-specific antibody responses after A2aR-encoding DNA immunization, no binding from pre-bleed serum. (MFI: mean fluorescence intensity).

Mice with high specific titers were then selected for euthanization to isolate spleen aseptically.

Fusion of Sp2/0 Cells and Spleen Cells

Spleen tissues were homogenized. Single-cell suspension from the spleen were prepared, then fused with the SP2/0 myeloma cells at 1:1 ratio by electrofusion (BTX-Harvard Apparatus). The cells were then plated in 96-well plates with hypxanthine-aminopterin-thymidine (HAT) medium (Millipore-Sigma, Cat. H0262). The cells were cultured for 12-14 days with two medium changes to reduce nonspecific background for the next step screening.

Primary Screening of Hybridoma

Primary screening of the hybridoma supernatants in the 96-well plates was performed using the same FACS procedure as described for serum titration except following changes: 1) Human A2aR-expressing Expi293 cells (expressing GFP) were mixed at 1:1 ratio with parental Expi293 (no A2aR expression) and added to 96-well plates ($2\times10^5$ cells per well), 2) 50 μl hybridoma supernatant transferred from each well of 96-well plates was incubated with cells for 30 min. on ice. Positive wells to human A2aR-expressing cells, but not to parental Expi293 cells were selected and processed for sub-cloning.

Sub-Cloning

Figure 2:
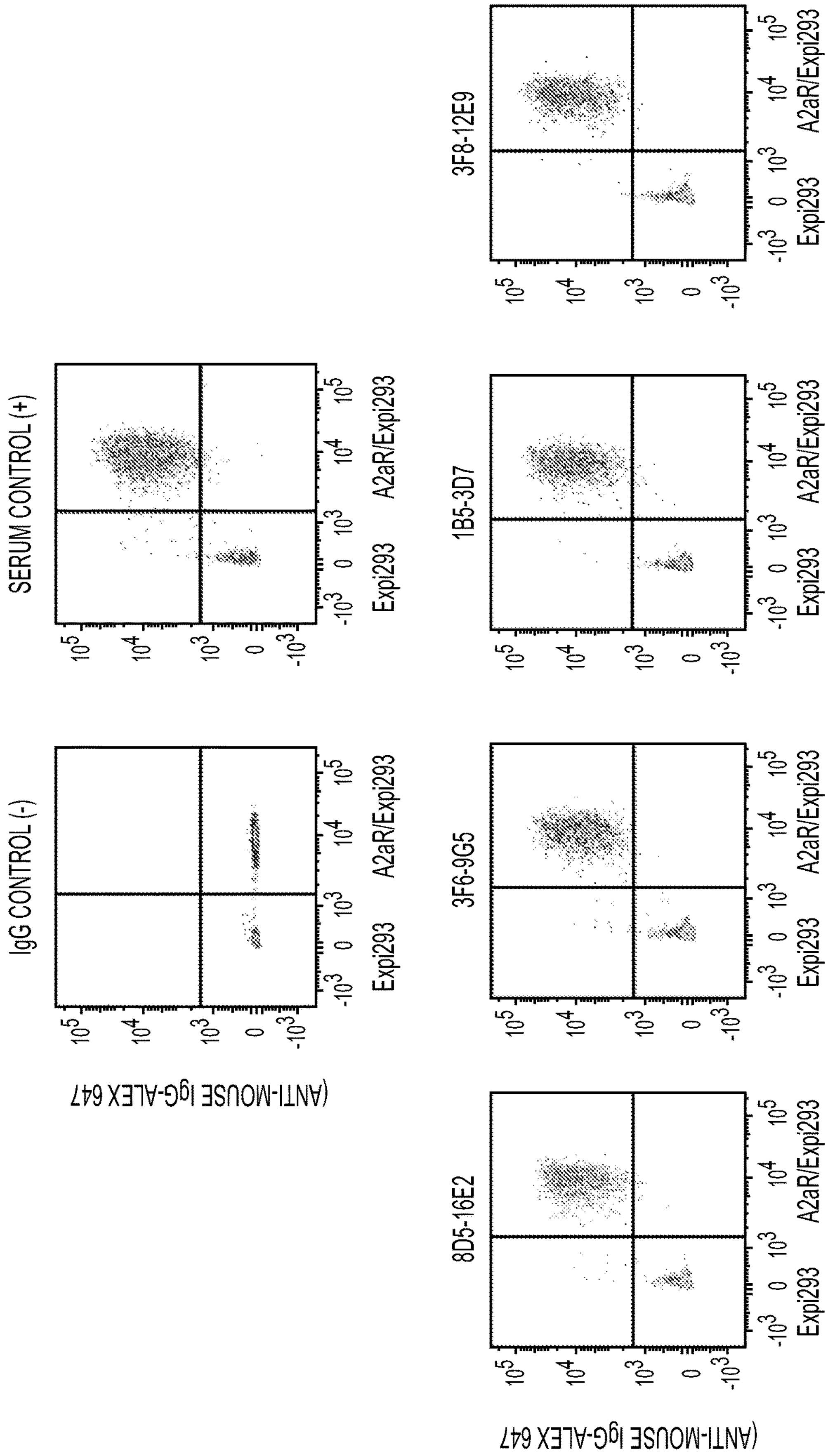
FIG. 2 includes fluorescence-activated cell sorting (FACS) plots showing the binding of anti-A2aR antibodies isolated from hybridoma cell culture medium of four hybridoma clones, 1B5-3D7, 3F6-9G5, 3F8-12E9, and 8D5-16E2. As used herein, the clone designation, i.e., 1B5-3D7, 3F6-9G5, 3F8-12E9, and 8D5-16E2, also represents the monoclonal antibody isolated from these clones depending on the context. Expi293: Expi293 cells; A2aR/Expi293: Expi293 cells transfected with vector expressing human A2aR.

Sub-cloning was performed by limiting dilution method. In short, the positive wells identified by FACS were seeded into 96-well plate at an average density of 1 cell/well. The 9-well plate was placed in incubator for 7-10 days to allow the growth of the cells. The growth of cells was monitored periodically. At about day 4, the wells on the plate were observed under phase contrast microscopy and the wells which appeared to have single colony growing (i.e., only one clumping of hybridomas) were recorded. The cells from the single colony wells were screed by FACS using the same procedure as described for primary screening of hybridoma when the confluence of the cell reached about 50%. As shown in FIG. 2, the antibodies isolated from the hybridoma clones 1B5-3D7, 3F6-9G5, and 3F8-12E9, 8D5-16E2 showed specific binding to human A2aR-expressing cells, but not to parental Expi293 cells.

Hybridoma Cell Culture and Antibody Purification

Hybridoma cells were grown in BD Cell mAb Quantum yield medium (Thermo Fisher, Cat. 220511) supplemented with low IgG Fetal Bovine Serum (Millipore Sigma, Cat. F1283). Supernatant were collected when cell viability dropped to about to 50%. Antibodies were purified using Protein G resin following manufactory protocol.

Example 2: Cloning of Antibody Variable Regions from Anti-A2aR Mouse Hybridomas SMARTer RACE kit (TaKaRa, Cat. 634858) was used to clone the DNA fragments that encode the variable regions of the exemplary antibodies (i.e., HCVR and LCVR) from 4 mouse hybridomas. Each of the four mouse hybridomas were cultured and confirmed via subclass testing to produce monoclonal antibodies with H and L chain consisting of γ2a and κ chains, respectively. Total RNA was prepared from $3\times10^6$ cells using a Qiagen RNA Kit.

Following the protocol for the SMARTer RACE cDNA Amplification Kit, the first-strand cDNA was first synthesized with the addition of the SMART sequence at the 5' end enabling the use of this site for downstream amplification and cloning using total RNA as a template. For each sample, two PCR reactions were performed at the same time, using universal forward primer (provided in kit) and reverse primers (designed based on the constant region sequence of mouse IgG2a and mouse Kappa classes registered in the NCBI-nucleotide database) for H and L chain, respectively.

The amplified PCR products from above reactions were purified by gel extraction with the NuceloSpin Gel and PCR Clean-Up Kit (Qiagen, Cat. 740609) after agarose gel electrophoresis and cloned into the linearized pRACE vector (provided in SMARTer RACE kit) with In-Fusion HD Cloning (provided in SMARTer RACE kit). H and L variable region sequences were analyzed and determined via Sanger sequencing.

The amino acid sequences of the CDRs, HCVRs, and LCVRs of exemplary antibodies 1B5-3D7, 3F6-9G5, and 3F8-12E9 are shown in Tables 1-5 as defined using Kabat and IMGT numbering scheme. Tables 10 and 11 show exemplary nucleic acid sequences that encode the exemplary antibodies 1B5-3D7, 3F6-9G5, and 3F8-12E9.

Example 3: Recombinant Expression and Purification of Mouse IgG Antibodies

For expression in mammalian cell line, antibody genes encoding 1B5-3D7 and 3F6-9G5 were first recloned into suitable expression vectors. Following small-scale preparation of plasmid DNA, Expi293 cell line was used for transient transfection. Supernatants were collected after 5 to 7 days post transfection and antibodies in IgG format were purified using Protein G resin following manufactory protocol (GE, Cat. GE17-0618-01).

Example 4: In Vitro Blocking Activity of the Anti-Human A2aR mAbs 8D5-16E2, 3F6-9G5, 1B5-3D7, and 3F8-12E9

The activity of A2aR is mediated by Gas protein which activates adenylyl cyclase, resulting in the synthesis of intracellular cAMP. The level of cAMP correlates with the respective adenosine (agonist) level. cAMP can be detected using a variety of commercial cAMP assay kit.

HEK293 cells that stably express human A2aR (BPS Bioscience, Cat. 79381) were seeded at 5000 cells/well in 200 μl starvation media (MEM (Hyclone Cat. SH30024.01)+2% charcoal stripped serum (Thermo Fisher Cat. A3382101)) and cultured at 37° C. overnight. On the next day, after washing 3 times with 200 μl of warm PBS, either purified A2aR mAb (1B5-3D7, 3F6-9G5, and 3F8-12E9) or ZM241385 control (standard small molecule antagonist for A2aR) in induction buffer (PBS w/500 μM 3-Isobutyl-1-methylxanthine (IBMX) (Millipore Sigma, Cat. 17018)+100 μM Ro 20-1724, Millipore Sigma, Cat. B8279) in 2-fold or 3-fold serially diluted concentration, was pre-incubated with the cells for 15 min at 37° C. After the incubation with the antibodies or ZM241385 (Millipore Sigma, Z0153), a stable adenosine agonist, NECA (Millipore Sigma, E2387) was added thereafter to a final concentration of 300 nM or 500 nM. The cells were then incubated for another 1 hour at 37° C. cAMP-Glo™ Assay kit (Promega, Cat. V1501) was used to perform cell lysis and detected cAMP. Result (Relative Light Unit, RLU) was read using Luminometer. RLU can be converted to cAMP (nM) using cAMP standard curve and Prism software.

Figure 3:
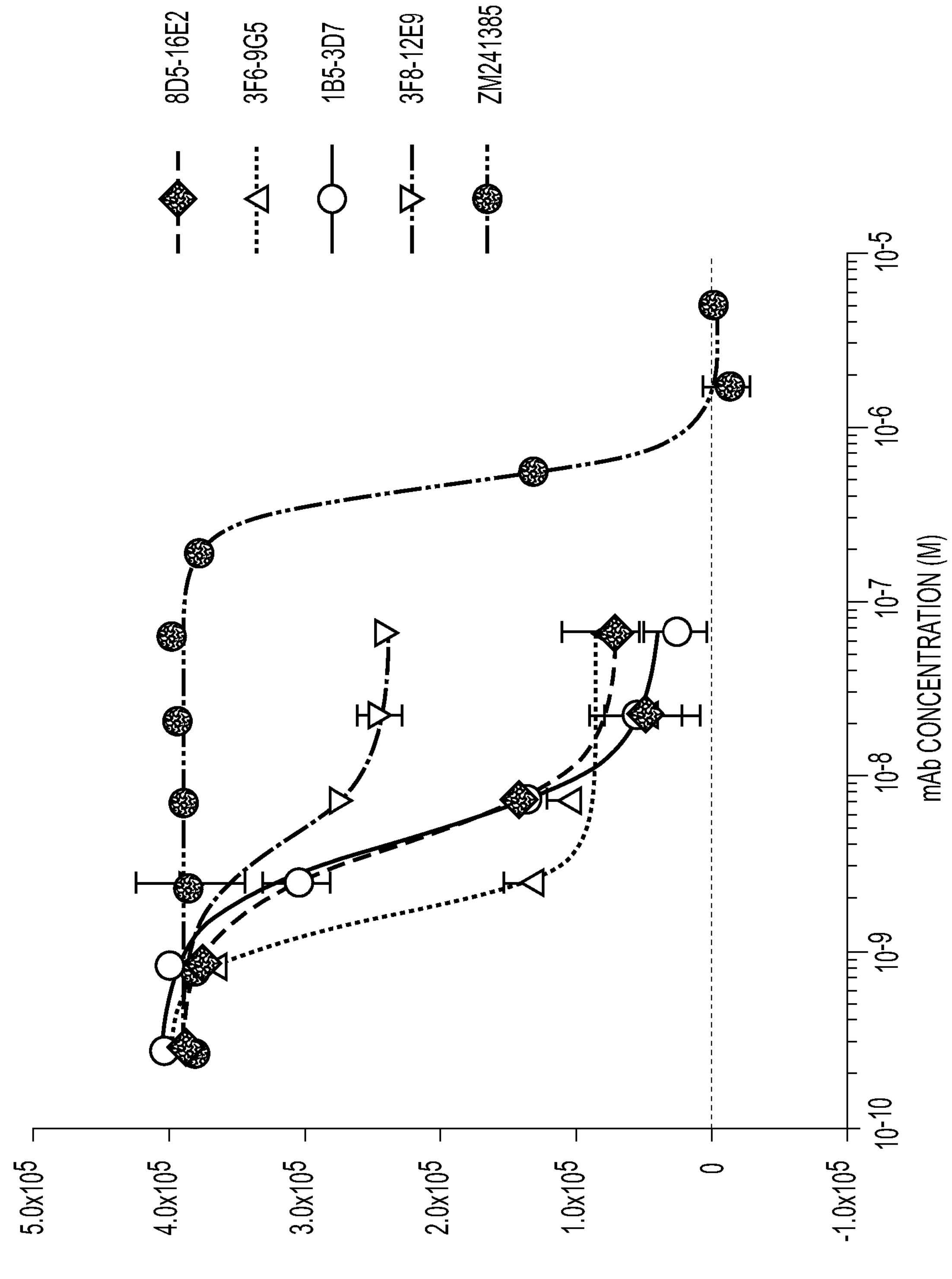
FIG. 3 is a graph showing in vitro blocking activity of anti-human A2aR mAbs 1B5-3D7, 3F6-9G5, 3F8-12E9, and 8D5-16E2 in cell-based cAMP assay with the exemplary antibodies of the invention in whole IgG molecule format purified from hybridoma medium. RLU: Relative Light Unit; ZM241385: a small molecule A2aR antagonist (Sigma, Cat. Z0153)

As shown in FIG. 3, the exemplary antibodies of the present invention, anti-human A2aR mAbs 1B5-3D7, 3F6-9G5, and 3F8-12E9, in the mouse IgG2a format purified from hybridoma supernatants, blocked the activities of human A2aR expressed on a cell surface with an $IC_{50}$ value between about $4.5\times10^{-9}$ M to about $1.5\times10^{-9}$ M. Table 11 shows the $IC_{50}$ value of the exemplary antibodies for blocking the cAMP production induced upon NECA binding to cell surface human A2aR. $IC_{50}$ value of the exemplary antibodies is 100 fold lower that for small molecule inhibitor (SMI) ZM241385, indicating the in vitro inhibition of the exemplary antibodies are at least 100-fold more potent than SMI ZM241385.

TABLE 11

$IC_{50}$ Value of Exemplary Antibodies for Binding to Cell Surface Human A2aR

| | 1B5-3D7 | 3F6-9G5 | 3F8-12E9 | ZM241385 |
|---|---|---|---|---|
| $IC_{50}$ (M) | 4.48E−09 | 1.57E−09 | 4.35E−09 | 4.72E−07 |

Figure 4:
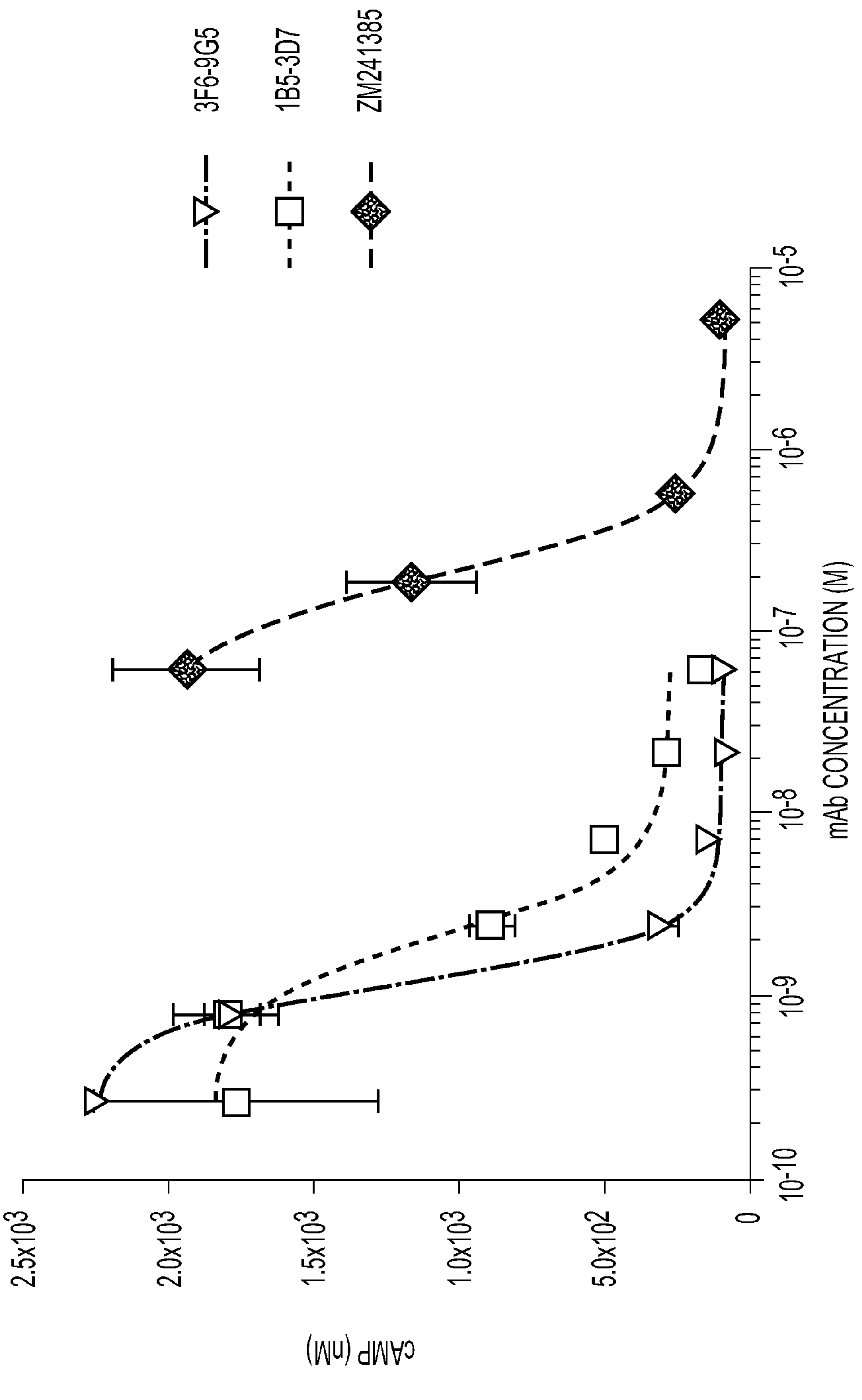
FIG. 4 is a graph showing in vitro blocking activities of anti-human A2aR mAbs 1B5-3D7, and 3F6-9G5 in a cell-based cAMP assay with the exemplary antibodies of the invention in recombinant whole IgG molecule format purified from culture supernatant of Expi293 cells transiently transfected with vector encoding the sequences of the exemplary antibodies of invention.

As shown in FIG. 4, the exemplary antibodies of the present invention, anti-human A2aR mAbs 1B5-3D7, 3F6-9G5, in the mouse IgG2a format purified from Expi293 cells transiently transfected with recombinant expression vectors that expressed the antibody genes, showed similar $IC_{50}$ blocking the activities of human A2aR expressed on a cell surface.

Example 5: Determination of Specificity of Anti-Human A2aR Antibodies

The purpose of this assessment was to determine the specificity of the exemplary anti-human A2aR antibodies (clones 1B5-3D7 and 3F6-9G5) to adenosine receptor family members including human AIR, A2bR and A3R, as well as their cross-reactivity to mouse A2aR.

Methods

To test the specificity of the antigen binding molecules of the invention, e.g., anti-A2aR antibodies or antigen binding fragments thereof to human A2aR and not towards any of the other 3 adenosine receptor family members, a flow cytometry-based cell-binding assay was performed by Multispan Inc (Hayward, CA). HEK293T cells stably expressing various adenosine receptors, i.e., human A1R, A2bR, and A3R, and mouse A2R, generated by Multispan Inc and HEK293T parental cell lines were used in the assay. Briefly, adenosine receptor-overexpressing cell lines and HEK293T parental cell lines were incubated with 2, 10, and 50 nM of anti-human A2aR monoclonal antibodies (clones 1B5-3D7 and 3F6-9G5) and 10 and 50 nM of mouse IgG2a Isotype control at 4° C. in the dark for 60 minutes. Anti-FLAG antibody (Abcam, ab72469, 2 μg/mL) was used as positive control for cell lines over-expressing various adenosine receptors, respectively. After 3 washes with FACS buffer (PBS plus 0.1% BSA and 0.2% sodium azide), cells were stained with an anti-mouse-IgG-PE (Invitrogen, cat. P852) detection antibody for 45 minutes at 4° C. The cells were then washed 3 times with FACS buffer and analyzed on FACSort (Becton Dickinson). Data was analyzed using CellQuest Pro (Becton Dickinson).

Results

The two exemplary antibodies of the invention, 1B5-3D7 and 3F6-9G5, specifically bound to human A2aR. The binding to other human adenosine receptors or mouse A2aR was either similar to the level of the binding detected in negative control (HEK293T) or significantly weaker (HEK293T-A1) than the binding to human A2aR (Table 12).

Table 12 summarizes binding signal of exemplary antibodies 1B-3D7 and 3F6-9G5 to parental HEK293T cell s or HEK293 cells expressing different adenosine receptors performed in duplicate by FACS assay.

TABLE 12

Binding of Exemplary Antibodies to HEK293 Cells Expressing Different Adenosine Receptor

| | 1B5-3D7 | | | 3F6-9G5 | | | Isotype Ctrl mIgG2a | | anti- |
|---|---|---|---|---|---|---|---|---|---|
| Geo Mean | 50 nM | 10 nM | 2 nM | 50 nM | 10 nM | 2 nM | 50 nM | 10 nM | FLAG |
| HEK293T- | 27.59 | 18.4 | 10.15 | 22.97 | 15.26 | 8.35 | 2.5 | 2.48 | 53.32 |
| A1 | 30.66 | 24.97 | 11.83 | 22.51 | 15.56 | 8.81 | 2.7 | 2.24 | 121.29 |
| HEK293T- | 260.67 | 261.79 | 97.49 | 270 | 273.51 | 112.47 | 2.92 | 2.97 | 183.3 |
| A2A | 377.56 | 221.91 | 95.04 | 289.37 | 290.29 | 109.2 | 2.83 | 2.82 | 223.45 |
| HEK293T- | 3.42 | 7.23 | 5.42 | 7.27 | 6.07 | 3.13 | 2.33 | 2.42 | 78.57 |
| A2B | 2.79 | 3.58 | 3.8 | 3.74 | 2.93 | 2.8 | 2.69 | 2.41 | 50.12 |
| HEK293T- | 2.45 | 2.23 | 2.11 | 2.66 | 2.49 | 2.07 | 1.87 | 1.9 | 48.17 |
| A3 | 2.3 | 2.32 | 2.09 | 2.25 | 2.33 | 1.96 | 1.84 | 1.81 | 47.36 |
| HEK293T- | 3.48 | 4.13 | 2.96 | 4.98 | 3.7 | 2.9 | 2.05 | 2 | 70.36 |
| mA2A | 6.03 | 6.16 | 3.82 | 4.76 | 3.25 | 3.08 | 2.06 | 2.39 | 104.61 |
| HEK293T | 5.24 | 5.42 | 3.69 | 4.19 | 4.01 | 3.98 | 3.78 | 3.75 | 3.8 |
| | 4.96 | 4.07 | 4.11 | 6.16 | 4.27 | 4.33 | 3.29 | 3.73 | 4.22 |

HEK293T-A1: HEK293T cell expressing human adenosine receptor A1
HEK293T-A2A: HEK293T cell expressing human adenosine receptor A2A
HEK293T-A2B: HEK293T cell expressing human adenosine receptor A2B
HEK293T-A3: HEK293T cell expressing human adenosine receptor A3
HEK293T-mA2A: HEK293T cell expressing mouse adenosine receptor A2A
HEK293T: HEK293T cell without exogenous adenosine receptor Example 6: Comparison of Binding Affinity Between Exemplary Anti-Human A2aR Antibodies of the Present Invention and Other Anti-Human A2aR Antibodies Human A2aR-expressing Expi293 cells or parental Expi293 cells were first added to 96-well plate ($1\times10^5$ cells per well). Fifty microliters (50 μl) of 12-point 1:2 serial diluted samples starting from 7.5 ug/ml for each antibody was incubated with cells for 30 minutes on ice. After being washed with FACS buffer (2% Fetal bovine serum in DPBS), 100 d of 1 g/ml of Alex Fluor 633-conjugated anti mouse IgG (Life technology, Cat.A21050) or Alex Fluor 647-conjugated anti-human IgG was added and incubated for 30 minutes on ice. Cells were resuspended with 100 μl of FACS buffer after two washes. One hundred microliters 100 μl of 1:50 diluted 7-AAD for live/dead staining was added to the cell suspension, which was ready for FACS analysis (BD Accuri C6 plus or LSR II Flow Cytometer, HTS).

Figure 5:
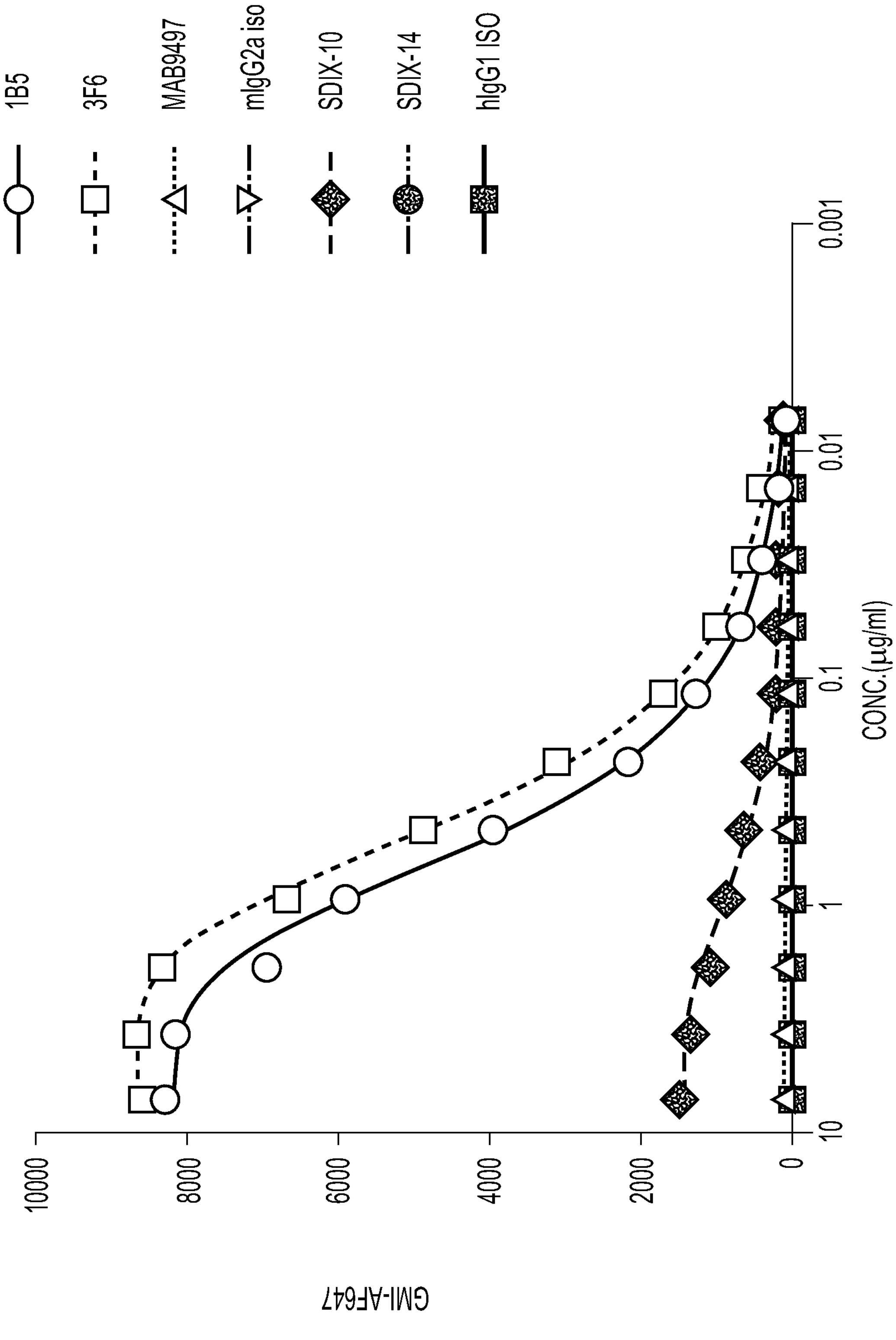
FIG. 5 is a graph showing that the exemplary antibodies of the invention, 1B5-3D7 and 3F6-9G5, specifically binds to human A2aR expressed on a cell surface. The graph also shows that the binding of anti-human A2aR antibodies from other sources to human A2aR expressed on a cell surface is undetected or weak. 1B5: 1B5-3D7; 3F6: 3F6-9G5; MAB9497: human adenosine A2aR antibody, R&D Systems, Cat. MAB9497; SDIX-10: human adenosine A2aR antibody disclosed in US Patent Publication US2014/0322236A1, clone 864H10; SDIX-14: human adenosine A2aR antibody disclosed in US Patent Publication US2014/0322236A1, clone 864H14; mIgG2a iso: mouse IgG2a isotype control; hIgG1 iso: human IgG1 isotype control.

As shown in FIG. 5, the exemplary antibody 1B5-3D7 and 3F6-9G5 at mIgG2a format showed strong dose-dependent specific binding to hA2aR-Expi293, but not to parental Expi293. Surprisingly, no binding to hA2aR-Expi293 cells was detected for staining with anti-A2aR monoclonal antibodies MAB9497R (R&D Systems, clone 599717R) or SDIX-14 (US Patent Publication US2014/0322236A1, clone 864H14). In addition, anti-hA2aR monoclonal antibodies SDIX-10 (US Patent Publication US2014/0322236A1, clone 864H10) showed non-specific binding with similar lower GMI (<2000 at 50 nM concentration) to both hA2aR-Expi293 cells and parental Expi293 cells. (GMI: Geometric mean fluorescence intensity).

Example 7: Determination of Anti-Human A2aR Antibody Binding to Human and Cynomolgus Primary Cells and Cross-Reactivity to Non-Human Primates In human, A2aR has been reported to be expressed by T cells. Adenosine-blocking anti-human A2aR antibody (clone 3F6-9G5) was tested for potential binding to human and cynomolgus PBMC.

Methods

Human and cynomolgus PBMCs were purchased from Cytologics LLC (San Diego, CA) and iQ Biosciences (Berkeley, CA), respectively. Primary cell binding was determined using anti-human A2aR clone 3F6-9G5 at rabbit Fc format. In brief, $10^6$ human and/or cynomolgus PBMCs in 100 μl FACS buffer were incubated with 3F6-9G5 (2 μg/ml) at 4° C. for 60 minutes. Cynomolgus cross-reactive anti-human CD3 (clone SP34, BD), anti-human CD8 (clone RPA-T8, Biolegend) and Zombie Green fixable Viability dye (Biolegend, Cat. 423111) were used according to manufacturer's instruction to define live immune cell subsets. After 3 washes with FACS buffer, cells were stained with PE-conjugated donkey anti-rabbit Fc detection antibody (1:200, Biolegend, Cat. 406421) for 30 minutes at 4° C. After 3 washes with FACS buffer, cells were analyzed on LSRII (Becton Dickinson). Data was analyzed using FlowJo (Becton Dickinson).

Results

Figure 6:
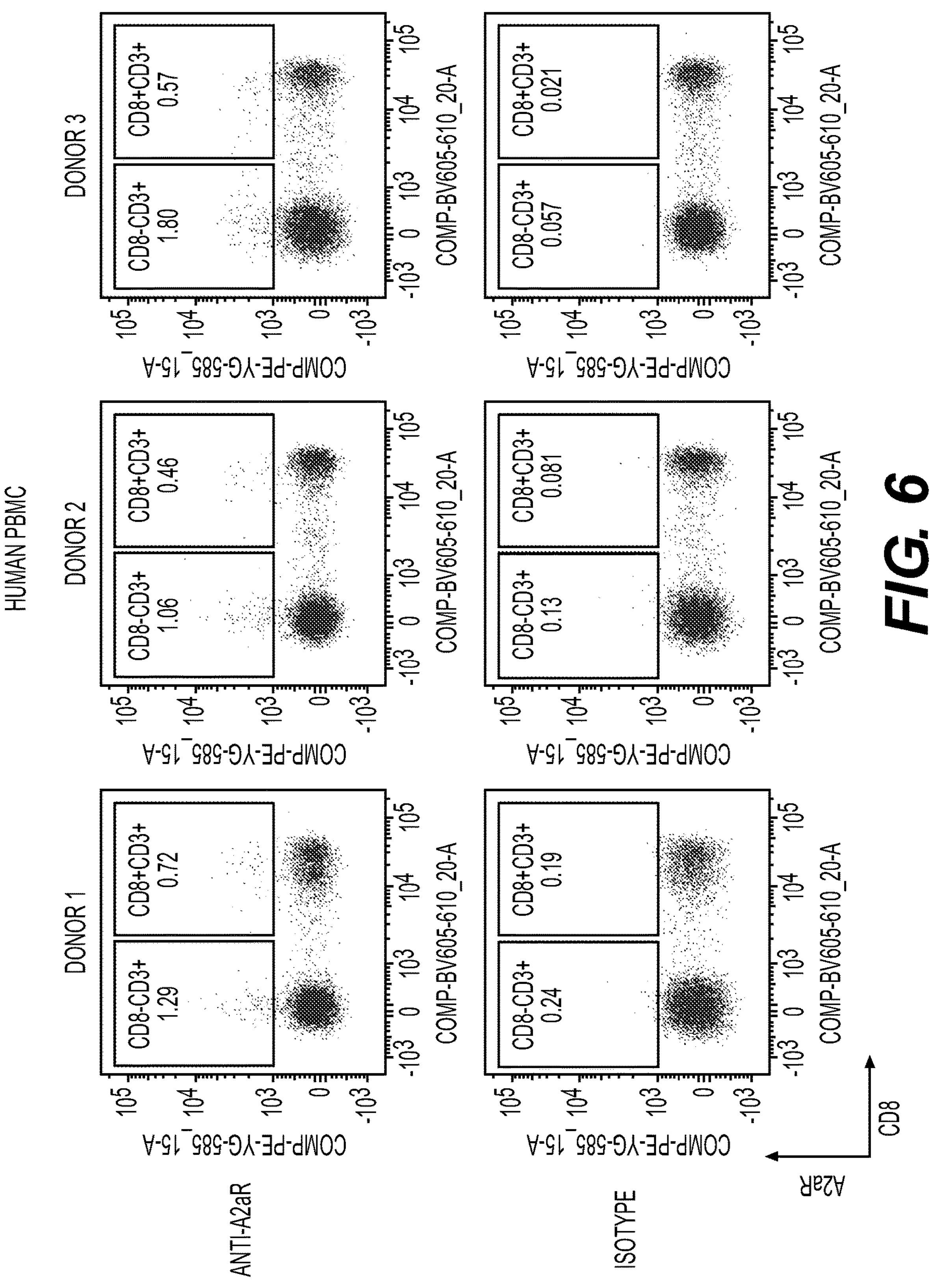
FIG. 6 includes flow cytometry assay dot plots showing that an exemplary antibody of the invention, 3F6-9G5, binds to human A2aR and cynomolgus A2aR expressed on cell surface of $CD8^{+}CD3^{+}$ CD8 T cells and $CD8^{-}CD3^{+}$ CD4 T cells from human and cynomolgus periphery blood mononuclear cells (PBMC). GMI: Geometric mean fluorescence intensity.
Figure 6:
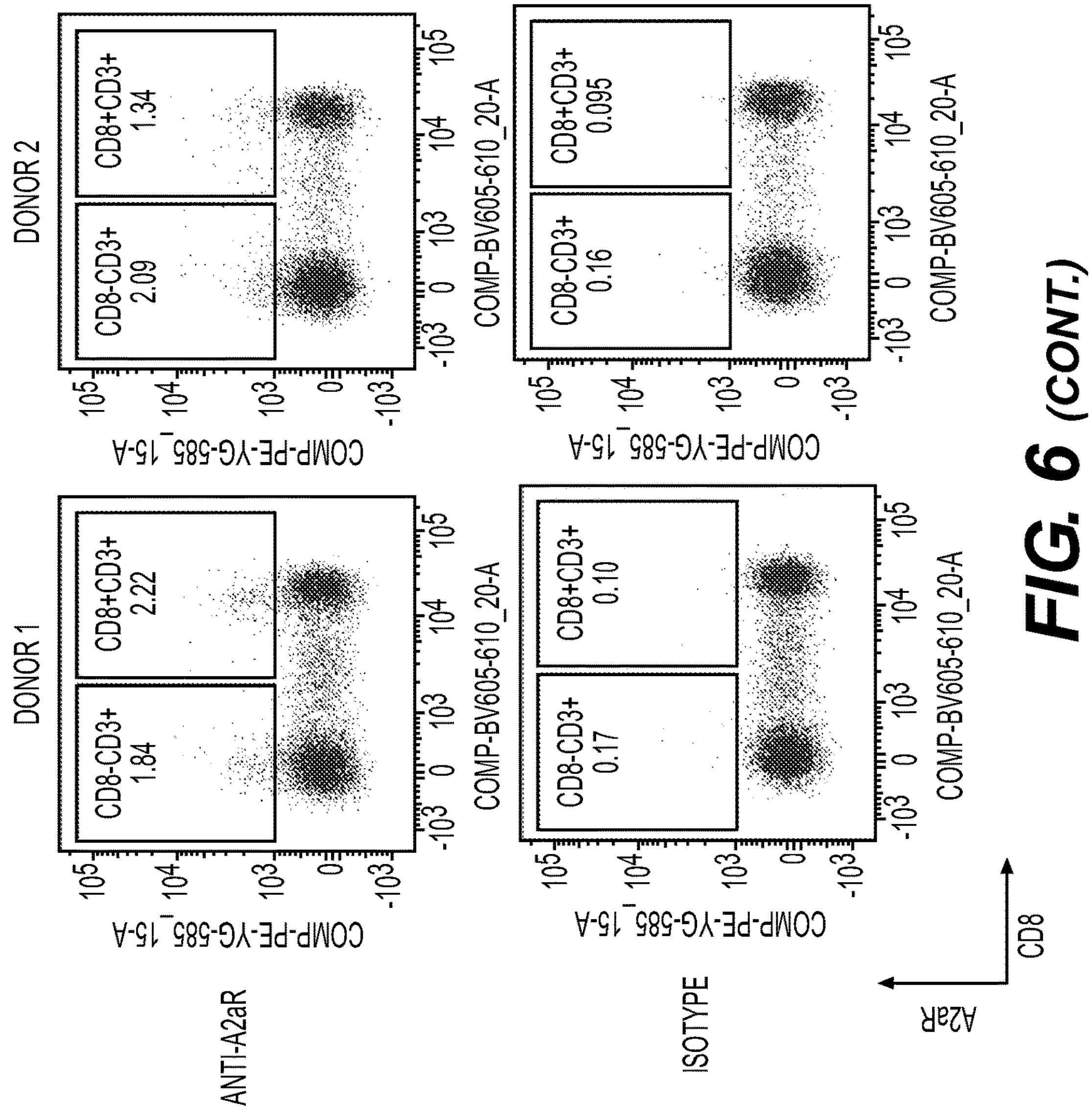

Anti-human A2aR clone 3F6-9G5, but not Anti-HEL rabbit Fc isotype control (Biointron, Cat. B730001) bound to a small subset of human T cells (both CD4+ and CD8+) (FIG. 6). It also cross-reacted with cynomolgus T cells (both CD4+ and CD8+) (FIG. 6).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. An isolated antibody or antigen-binding fragment thereof that binds to human adenosine A2A receptor (A2aR), comprising a heavy chain variable (VH) domain comprising from N-terminus to C-terminus, three heavy chain complementarity-determining regions (CDRs), HCDR1, HCDR2, and HCDR3; and a light chain variable (VL) domain comprising from N-terminus to C-terminus, three light chain complementarity-determining regions (CDRs), LCDR1, LCDR2, and LCDR3; wherein (a) the HCDR1 comprises an amino acid sequence $X_1$-$X_2$-W-M-N(SEQ ID NO: 8), wherein $X_1$ is S or R, and $X_2$ is Y or F;

(b) the HCDR2 comprises an amino acid sequence R-I-D-P-$X_3$-D-S-E-$X_4$-$X_5$-Y-$X_6$-H-K-F-W-$X_7$ (SEQ ID NO: 9), wherein $X_3$ is S or Y, $X_4$ is A or T, $X_5$ is H or Q, $X_6$ is H or N, and $X_7$ is D or G;

(c) the HCDR3 comprises an amino acid sequence SLYGKGDY (SEQ ID NO: 3)

(d) the LCDR1 comprises an amino acid sequence R-S-S-Q-S-$X_{17}$-V-H-$X_{18}$-N-G-N-T-Y-L-E (SEQ ID NO: 30), wherein $X_{17}$ is L or I, $X_{18}$ is R or S;

(e) the LCDR2 comprises an amino acid sequence K-V-S-N-R-F-S(SEQ ID NO: 26); and (f) the LCDR3 comprises an amino acid sequence $X_{19}$-Q-G-S-H-V-P-L-T (SEQ ID NO: 31), wherein $X_{19}$ is Y or F.

2. The isolated antibody or the antigen binding fragment thereof of claim 1, wherein:

(a) the HCDR1 comprises an amino acid sequence selected from the group consisting of SEQ ID NOs: 1, 4, and 6;

(b) the HCDR2 comprises an amino acid sequence selected from the group consisting of SEQ ID NOs: 2, 5, and 7;

(c) the HCDR3 comprises an amino acid sequence as set forth in SEQ ID NO: 3;

(d) the LCDR1 comprises an amino acid sequence as set forth in SEQ ID NO: 25 or 28;

(e) the LCDR2 comprises an amino acid sequence as set forth in SEQ ID NO: 26; and (f) the LCDR3 comprises an amino acid sequence as set forth in SEQ ID NO: 27 or 29.

3. The isolated antibody or the antigen binding fragment thereof of claim 2, wherein the antibody comprises:

(a) the HCDR1 comprising an amino acid sequence set forth in SEQ ID NO: 1, the HCDR2 comprising an amino acid sequence set forth in SEQ ID NO: 2, the HCDR3 comprising an amino acid sequence set forth in SEQ ID NO: 3, the LCDR1 comprising an amino acid sequence set forth in SEQ ID NO: 25, the LCDR2 comprising an amino acid sequence set forth in SEQ ID NO: 26, and the LCDR3 comprising an amino acid sequence set forth in SEQ ID NO: 27;

(b) the HCDR1 comprising an amino acid sequence set forth in SEQ ID NO: 4, the HCDR2 comprising an amino acid sequence set forth in SEQ ID NO: 5, the HCDR3 comprising an amino acid sequence set forth in SEQ ID NO: 3, the LCDR1 comprising an amino acid sequence set forth in SEQ ID NO: 28, the LCDR2 comprising an amino acid sequence set forth in SEQ ID NO: 26, and the LCDR3 comprising an amino acid sequence set forth in SEQ ID NO: 29; or (c) the HCDR1 comprising an amino acid sequence set forth in SEQ ID NO: 6, the HCDR2 comprising an amino acid sequence set forth in SEQ ID NO: 7, the HCDR3 comprising an amino acid sequence set forth in SEQ ID NO: 3, the LCDR1 comprising an amino acid sequence set forth in SEQ ID NO: 25, the LCDR2 comprising an amino acid sequence set forth in SEQ ID NO: 26, and the LCDR3 comprising an amino acid sequence set forth in SEQ ID NO: 29.

4. The isolated antibody or the antigen binding fragment thereof of claim 1, wherein (a) the HCDR1 comprises an amino acid sequence selected from the group consisting of SEQ ID NOs: 21, 22, 23, and 24; and (b) the HCDR3 comprises an amino acid sequence selected from the group consisting of SEQ ID NOs: 12, 15, and 20.

5. The isolated antibody or the antigen binding fragment thereof of claim 1, wherein the antibody comprises:

(a) a heavy chain variable region (HCVR) comprising an amino acid sequence selected from the group consisting of SEQ ID NOs: 35, 36, 37, 38, 39, and 40; and (b) a light chain variable region (LCVR) comprising an amino acid sequence selected from the group consisting of SEQ ID NOs: 41, 42, and 43.

6. The isolated antibody or the antigen binding fragment thereof of claim 5, wherein the antibody comprises:

(a) the HCVR comprising an amino acid sequence set forth in SEQ ID NO: 35 or 38, and the LCVR comprising an amino acid sequence set forth in SEQ ID NO: 41;

(b) the HCVR comprising an amino acid sequence set forth in SEQ ID NO: 36 or 39, and the LCVR comprising an amino acid sequence set forth in SEQ ID NO: 42; or (c) the HCVR comprising an amino acid sequence set forth in SEQ ID NO: 37 or 40, and the LCVR comprising an amino acid sequence set forth in SEQ ID NO: 43.

7. An isolated antibody or antigen binding fragment thereof that binds human adenosine A2A receptor (human A2aR), comprising:

a heavy chain variable (VH) domain comprising from N-terminus to C-terminus, three heavy chain complementarity-determining regions (CDRs), HCDR1, HCDR2, and HCDR3; and a light chain variable (VL) domain comprising from N-terminus to C-terminus, three light chain complementarity-determining regions (CDRs), LCDR1, LCDR2, and LCDR3; wherein (a) the HCDR1 comprises an amino acid sequence SYWMN (SEQ ID NO: 4);

(b) the HCDR2 comprises an amino acid sequence RIDPSDSEAHYHHKFWG (SEQ ID NO: 5);

(c) the HCDR3 comprises an amino acid sequence SLYGKGDY (SEQ ID NO: 3);

(d) the LCDR1 comprises an amino acid sequence RSSQSLVHRNGNTYLE (SEQ ID NO: 28);

(e) the LCDR2 comprises an amino acid sequence KVSNRFS (SEQ ID NO: 26); and (f) the LCDR3 comprises an amino acid sequence YQGSHVPLT (SEQ ID NO: 29).

8. The isolated antibody or antigen binding fragment thereof of claim 7, comprising:

(a) a heavy chain variable region (HCVR) comprising an amino acid sequence as set forth in SEQ ID NO: 36 or 39; and (b) a light chain variable region (LCVR) comprising an amino acid sequence as set forth in SEQ ID NO: 42.

9. The antibody or the antigen binding fragment thereof of claim 1, wherein the antibody is a humanized antibody or a chimeric antibody.

10. An isolated polynucleotide encoding the antibody or the antigen binding fragment thereof of claim 1, an HCVR thereof, an LCVR thereof, a light chain thereof, a heavy chain thereof, or an antigen binding fragment thereof.

11. An expression vector comprising the polynucleotide of claim 10.

12. A recombinant cell comprising the polynucleotide of claim 10.

13. A method of treating a cancer in a subject having the cancer, comprising administering an isolated antibody or the antigen binding fragment thereof of claim 1, thereby treating the cancer.

14. The method of claim 13, further comprising administering an additional therapeutic agent.

15. The method of claim 14, wherein the additional therapeutic agent comprises an anti-tumor agent, radiotherapy, a chemotherapeutic agent, a surgery, a cancer vaccine, an agonist to a stimulatory receptor of an immune cell, a cytokine, a cell therapy, or a checkpoint inhibitor.

16. The method of claim 15, wherein the checkpoint inhibitor is an agent that inhibits PD-1, PD-L1, TIGIT, CTLA-4, PD-1, PD-LI, PD-L2, LAG-3, TIM-3, neuritin, BTLA, CECAM-1, CECAM-5, IL-1R8, VISTA, LAIR1, LILRB1, LILRB2, LILRB3, LILRB4, LILRB5, CD96, CD112R, CD 160, 2B4, TGFβ-R, KIR, NKG2A, and any combination thereof.

17. The method of claim 16, wherein the agent inhibits the interaction between PD-1 and PD-L1, and the agent is selected from the group consisting of pembrolizumab, nivolumab, atezolizumab, avelumab, durvalumab, BMS-936559, sintilimab, toripalimab, tislelizumab, camrelizumab, sugemalimab, penpulimab, and cadonilimab.

18. The method of claim 16, wherein the CTLA4 inhibitor is ipilimumab, or cadonilimab.

19. The method of claim 15, wherein the additional therapeutic agent is an agonist to a stimulatory receptor of an immune cell selected from OX40, CD2, CD27, CDS, ICAM-1, LFA-1, ICOS (CD278), 4-1 BB (CD137), GITR, CD28, CD30, CD40, BAFFR, HVEM, CD7, LIGHT, NKG2C, NKG2D, SLAMF7, NKp46, NKp80, CD160, B7-H3, CD83 ligand, and any combination thereof.

20. The method of claim 13, wherein the isolated antibody or the antigen binding fragment thereof comprises a heavy chain variable (VH) domain comprising from N-terminus to C-terminus, three heavy chain complementarity-determining regions (CDRs), HCDR1, HCDR2, and HCDR3; and a light chain variable (VL) domain comprising from N-terminus to C-terminus, three light chain complementarity-determining regions (CDRs), LCDR1, LCDR2, and LCDR3; wherein (a) the HCDR1 comprises an amino acid sequence SYWMN (SEQ ID NO: 4);

(b) the HCDR2 comprises an amino acid sequence RIDPSDSEAHYHHKFWG (SEQ ID NO: 5);

(c) the HCDR3 comprises an amino acid sequence SLYGKGDY (SEQ ID NO: 3);

(d) the LCDR1 comprises an amino acid sequence RSSQSLVHRNGNTYLE (SEQ ID NO: 28);

(e) the LCDR2 comprises an amino acid sequence KVSNRFS (SEQ ID NO: 26); and (f) the LCDR3 comprises an amino acid sequence YQGSHVPLT (SEQ ID NO: 29).

* * * * *

```
                         SEQUENCE LISTING


<160> NUMBER OF SEQ ID NOS: 51

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Phe Trp Met Asn
1               5


<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Asp Pro Tyr Asp Ser Glu Thr Gln Tyr Asn His Lys Phe Trp
1               5                   10                  15

Asp


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Leu Tyr Gly Lys Gly Asp Tyr
1               5
```

```
<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Trp Met Asn
1               5


<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ile Asp Pro Ser Asp Ser Glu Ala His Tyr His His Lys Phe Trp
1               5                   10                  15

Gly


<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Tyr Trp Met Asn
1               5


<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ile Asp Pro Ser Asp Ser Glu Thr His Tyr Asn His Lys Phe Trp
1               5                   10                  15

Gly


<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S or R
<220> FEATURE:
<221> NAME/KEY: MOD_RES
<222> LOCATION: (2)..(2)
<223> OTHER INFORMATION: Y or F

<400> SEQUENCE: 8
```

Xaa Xaa Trp Met Asn
1 5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: S or Y
<220> FEATURE:
<221> NAME/KEY: MOD_RES
<222> LOCATION: (9)..(9)
<223> OTHER INFORMATION: A or T
<220> FEATURE:
<221> NAME/KEY: MOD_RES
<222> LOCATION: (10)..(10)
<223> OTHER INFORMATION: H or Q
<220> FEATURE:
<221> NAME/KEY: MOD_RES
<222> LOCATION: (12)..(12)
<223> OTHER INFORMATION: H or N
<220> FEATURE:
<221> NAME/KEY: MOD_RES
<222> LOCATION: (17)..(17)
<223> OTHER INFORMATION: D or G

<400> SEQUENCE: 9

Arg Ile Asp Pro Xaa Asp Ser Glu Xaa Xaa Tyr Xaa His Lys Phe Trp
1 5 10 15

Xaa

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Gly Phe Thr Phe Thr Arg Phe Trp
1 5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ile Asp Pro Tyr Asp Ser Glu Thr
1 5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Gly Arg Ser Leu Tyr Gly Lys Gly Asp Tyr 1 5 10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Gly Phe Ala Phe Thr Ser Tyr Trp
1 5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Ile Asp Pro Ser Asp Ser Glu Ala
1 5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Leu Arg Ser Leu Tyr Gly Lys Gly Asp Tyr
1 5 10

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Gly Phe Thr Phe Thr Arg Tyr Trp
1 5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Ile Asp Pro Ser Asp Ser Glu Thr
1 5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (3)..(3)
<223> OTHER INFORMATION: A or T
<220> FEATURE:
<221> NAME/KEY: MOD_RES
<222> LOCATION: (6)..(6)
<223> OTHER INFORMATION: R or S
<220> FEATURE:
<221> NAME/KEY: MOD_RES
<222> LOCATION: (7)..(7)
<223> OTHER INFORMATION: F or Y

<400> SEQUENCE: 18

Gly Phe Xaa Phe Thr Xaa Xaa Trp
1               5


<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: S or Y
<220> FEATURE:
<221> NAME/KEY: MOD_RES
<222> LOCATION: (8)..(8)
<223> OTHER INFORMATION: A or T

<400> SEQUENCE: 19

Ile Asp Pro Xaa Asp Ser Glu Xaa
1               5


<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G or L

<400> SEQUENCE: 20

Xaa Arg Ser Leu Tyr Gly Lys Gly Asp Tyr
1               5                   10


<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Phe Thr Phe Thr Arg Phe Trp Met Asn
1               5                   10


<210> SEQ ID NO 22
<211> LENGTH: 10
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 22

Gly Phe Ala Phe Thr Ser Tyr Trp Met Asn
1 5 10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gly Phe Thr Phe Thr Arg Tyr Trp Met Asn
1 5 10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: A or T
<220> FEATURE:
<221> NAME/KEY: MOD_RES
<222> LOCATION: (6)..(6)
<223> OTHER INFORMATION: R or S
<220> FEATURE:
<221> NAME/KEY: MOD_RES
<222> LOCATION: (7)..(7)
<223> OTHER INFORMATION: F or Y

<400> SEQUENCE: 24

Gly Phe Xaa Phe Thr Xaa Xaa Trp Met Asn
1 5 10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Arg Ser Ser Gln Ser Ile Val His Ser Asn Gly Asn Thr Tyr Leu Glu
1 5 10 15

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Lys Val Ser Asn Arg Phe Ser
1 5

<210> SEQ ID NO 27
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Gln Gly Ser His Val Pro Leu Thr
1               5


<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Ser Gln Ser Leu Val His Arg Asn Gly Asn Thr Tyr Leu Glu
1               5                   10                  15


<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Gln Gly Ser His Val Pro Leu Thr
1               5


<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: L or I
<220> FEATURE:
<221> NAME/KEY: MOD_RES
<222> LOCATION: (9)..(9)
<223> OTHER INFORMATION: R or S

<400> SEQUENCE: 30

Arg Ser Ser Gln Ser Xaa Val His Xaa Asn Gly Asn Thr Tyr Leu Glu
1               5                   10                  15


<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y or F

<400> SEQUENCE: 31

Xaa Gln Gly Ser His Val Pro Leu Thr
1               5
```

```
<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ile Val His Ser Asn Gly Asn Thr Tyr
1               5                   10


<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ser Leu Val His Arg Asn Gly Asn Thr Tyr
1               5                   10


<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: L or I
<220> FEATURE:
<221> NAME/KEY: MOD_RES
<222> LOCATION: (6)..(6)
<223> OTHER INFORMATION: R or S

<400> SEQUENCE: 34

Gln Ser Xaa Val His Xaa Asn Gly Asn Thr Tyr
1               5                   10


<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Pro Gly Thr Glu Leu Val Lys Pro Gly Ala
1               5                   10                  15

Pro Val Lys Leu Ser Cys Lys Thr Ser Gly Phe Thr Phe Thr Arg Phe
            20                  25                  30

Trp Met Asn Trp Val Arg Gln Arg Pro Gly Arg Gly Leu Glu Trp Ile
        35                  40                  45

Gly Arg Ile Asp Pro Tyr Asp Ser Glu Thr Gln Tyr Asn His Lys Phe
    50                  55                  60

Trp Asp Arg Ala Thr Leu Thr Val Asp Lys Ser Ser Ser Thr Val Tyr
65                  70                  75                  80

Ile Gln Leu Ser Ser Leu Thr Ser Glu Asp Ser Ala Val Tyr Tyr Cys
                85                  90                  95
```

Gly Arg Ser Leu Tyr Gly Lys Gly Asp Tyr Trp Gly Gln Gly Thr Thr
100 105 110

Leu Thr Val Ser Ser
115

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Gln Val Gln Leu Gln Gln Pro Gly Thr Glu Leu Val Lys Pro Gly Ala
1 5 10 15

Pro Val Arg Leu Ser Cys Lys Ala Ser Gly Phe Ala Phe Thr Ser Tyr
20 25 30

Trp Met Asn Trp Val Arg Gln Arg Pro Gly Arg Gly Leu Glu Trp Ile
35 40 45

Gly Arg Ile Asp Pro Ser Asp Ser Glu Ala His Tyr His His Lys Phe
50 55 60

Trp Gly Lys Ala Thr Leu Thr Val Asp Lys Ser Ser Ser Thr Val Tyr
65 70 75 80

Ile Gln Leu Asn Gly Leu Thr Ser Glu Asp Ser Ala Val Tyr Tyr Cys
85 90 95

Leu Arg Ser Leu Tyr Gly Lys Gly Asp Tyr Trp Gly His Gly Thr Thr
100 105 110

Leu Thr Val Ser Ser
115

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Gln Val Gln Leu Gln Gln Pro Gly Thr Glu Leu Val Lys Pro Gly Ala
1 5 10 15

Pro Val Lys Leu Ser Cys Lys Ala Ser Gly Phe Thr Phe Thr Arg Tyr
20 25 30

Trp Met Asn Trp Val Lys Gln Arg Pro Gly Arg Gly Leu Glu Trp Ile
35 40 45

Gly Arg Ile Asp Pro Ser Asp Ser Glu Thr His Tyr Asn His Lys Phe
50 55 60

Trp Gly Lys Ala Thr Leu Thr Val Asp Lys Ser Ser Ser Thr Ala Tyr
65 70 75 80

Ile Gln Leu Asn Ser Leu Thr Ser Glu Asp Ser Ala Val Tyr Tyr Cys
85 90 95

Leu Arg Ser Leu Tyr Gly Lys Gly Asp Tyr Trp Gly Gln Gly Thr Thr
100 105 110

Leu Thr Val Ser Ser
115

<210> SEQ ID NO 38
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Gln Gln Pro Gly Thr Glu Leu Val Lys Pro Gly Ala
1               5                   10                  15

Pro Val Lys Leu Ser Cys Lys Thr Ser Gly Phe Thr Phe Thr Arg Phe
            20                  25                  30

Trp Met Asn Trp Val Arg Gln Arg Pro Gly Arg Gly Leu Glu Trp Ile
        35                  40                  45

Gly Arg Ile Asp Pro Tyr Asp Ser Glu Thr Gln Tyr Asn His Lys Phe
    50                  55                  60

Trp Asp Arg Ala Thr Leu Thr Val Asp Lys Ser Ser Ser Thr Val Tyr
65                  70                  75                  80

Ile Gln Leu Ser Ser Leu Thr Ser Glu Asp Ser Ala Val Tyr Tyr Cys
                85                  90                  95

Gly Arg Ser Leu Tyr Gly Lys Gly Asp Tyr Trp Gly Gln Gly Thr Thr
            100                 105                 110

Leu Thr Val Ser Ser
        115


<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Gln Gln Pro Gly Thr Glu Leu Val Lys Pro Gly Ala
1               5                   10                  15

Pro Val Arg Leu Ser Cys Lys Ala Ser Gly Phe Ala Phe Thr Ser Tyr
            20                  25                  30

Trp Met Asn Trp Val Arg Gln Arg Pro Gly Arg Gly Leu Glu Trp Ile
        35                  40                  45

Gly Arg Ile Asp Pro Ser Asp Ser Glu Ala His Tyr His His Lys Phe
    50                  55                  60

Trp Gly Lys Ala Thr Leu Thr Val Asp Lys Ser Ser Ser Thr Val Tyr
65                  70                  75                  80

Ile Gln Leu Asn Gly Leu Thr Ser Glu Asp Ser Ala Val Tyr Tyr Cys
                85                  90                  95

Leu Arg Ser Leu Tyr Gly Lys Gly Asp Tyr Trp Gly His Gly Thr Thr
            100                 105                 110

Leu Thr Val Ser Ser
        115


<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Gln Gln Pro Gly Thr Glu Leu Val Lys Pro Gly Ala
```

```
1               5                   10                  15

Pro Val Lys Leu Ser Cys Lys Ala Ser Gly Phe Thr Phe Thr Arg Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn His Lys Phe
    50                  55                  60

Trp Gly Lys Ala Thr Leu Thr Val Asp Lys Ser Ser Ser Thr Ala Tyr
65                  70                  75                  80

Ile Gln Leu Asn Ser Leu Thr Ser Glu Asp Ser Ala Val Tyr Tyr Cys
                85                  90                  95

Leu Arg Ser Leu Tyr Gly Lys Gly Asp Tyr Trp Gly Gln Gly Thr Thr
            100                 105                 110

Leu Thr Val Ser Ser
        115


<210> SEQ ID NO 41
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Leu Thr Phe Gly Ser Gly Thr Thr Leu Glu Leu Lys
            100                 105                 110


<210> SEQ ID NO 42
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Val Leu Met Thr Gln Thr Pro Leu Ser Leu Ser Val Arg Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
65                  70                  75                  80

Ser Arg Val Glu Ala Glu Asp Leu Gly Val Tyr Tyr Cys Tyr Gln Gly
                85                  90                  95

Ser His Val Pro Leu Thr Phe Gly Ser Gly Thr Lys Leu Glu Ile Lys
            100                 105                 110
```

<210> SEQ ID NO 43
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Asp Val Leu Met Thr Gln Thr Pro Leu Ser Leu Ser Val Gly Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Tyr Gln Gly
                85                  90                  95

Ser His Val Pro Leu Thr Phe Gly Ser Gly Thr Lys Leu Glu Ile Lys
            100                 105                 110
```

<210> SEQ ID NO 44
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
caggtccaac ttcagcagcc tgggactgaa cttgtgaagc ctggggctcc agtgaagctg      60

tcctgtaaga cttctggctt caccttcacc aggttctgga tgaactgggt gaggcagagg     120

cctggacgag gcctcgagtg gattggaagg attgatcctt acgatagtga aactcaatat     180

aatcacaaat tctgggacag ggccacactg actgttgaca aatcctccag cacagtctac     240

atccaactca gcagcctgac atctgaggac tctgcggtct attactgtgg aagatcccta     300

tatggtaaag gggactactg gggccaaggc accactctca cagtctcctc a              351
```

<210> SEQ ID NO 45
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
caggtccaac tgcagcagcc tgggactgag cttgtgaagc ctggggctcc agtgaggctg      60

tcctgcaagg cttctggctt cgccttcacc agctactgga tgaactgggt gaggcagagg     120

cctggacgag gcctcgagtg gattggaagg attgatcctt ccgatagtga agctcactat     180
```

catcataaat tctggggcaa ggccacactg actgttgaca aatcctccag caccgtttac 240
atccagctca acggcctgac atctgaggac tctgcggtct attactgtct aagatcccta 300
tatggtaaag gggactactg gggccatggc accactctca cagtctcctc a 351

<210> SEQ ID NO 46
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46
caggtccaac tgcagcagcc tgggactgag cttgtgaagc ctggggctcc agtgaagctg 60
tcctgcaagg cttctggctt caccttcacc cgctactgga tgaactgggt gaagcagagg 120
cctggacgag gcctcgagtg gattggaagg attgatcctt ccgatagtga aactcactat 180
aatcataaat tctggggcaa ggccacactg actgttgaca aatcctccag cacagcctac 240
atccaactca acagcctgac atctgaggac tctgcggtct attactgtct aagatcccta 300
tatggtaaag gggactactg gggccaaggc accactctca cagtctcctc a 351

<210> SEQ ID NO 47
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47
gatgttttga tgacccagtc tccactctcc ctgcctgtca gtcttggaga tcaagcctcc 60
atctcttgca gatctagtca gagcattgta catagtaatg gaaacaccta tttagaatgg 120
tacctgcaga gaccaggcca gtctccaaaa ctcctgatct acaaagtttc caaccgattt 180
tctggggtcc cagacaggtt cagtggcagt ggatcaggga catatttcac actcaggatc 240
agcagagtgg aggctgaaga tctgggaatt tattactgct ttcaaggttc acatgttcct 300
ctcacgttcg gctcggggac aacattggaa ctaaaa 336

<210> SEQ ID NO 48
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48
gatgttttga tgacccaaac cccactctcc ctgtctgtca gacttggaga tcaagcctcc 60
atctcttgca gatctagtca gagtcttgta catagaaatg gaaacaccta tttagaatgg 120
tacctgcaga gaccaggcca gtctccaaag ctcctgatct acaaggtttc caaccgattt 180
tctggggtcc cagacaggtt cagtggcagt ggatcaggga cagatttcac actcaagatc 240
agcagagtgg aggctgaaga tctgggagtt tattactgct atcaaggttc acatgttcct 300
ctcacgttcg gctcggggac aaaattggaa ataaaa 336

<210> SEQ ID NO 49
<211> LENGTH: 336

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

gatgttttga tgacccaaac tccactctcc ctgtctgtcg gtcttggaga tcaagcctcc      60

atctcttgca gatctagtca gagtattgta catagtaatg gaaacaccta tttagaatgg     120

tacctgcaga gaccaggcca gtctccaaag ctcctgatct acaaagtttc caaccgattt     180

tctggggtcc cagacaggtt cagtggcagt ggatcaggga cagatttcac actcaagatc     240

agcagagtgg aggctgaaga tctgggagtt tattactgct atcaaggttc acatgttcct     300

ctcacgttcg gctcggggac aaaattggaa ataaaa                               336


<210> SEQ ID NO 50
<211> LENGTH: 412
<212> TYPE: PRT
<213> ORGANISM: Homo sapiens

<400> SEQUENCE: 50

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270
```

```
Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
    290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
    370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410


<210> SEQ ID NO 51
<211> LENGTH: 412
<212> TYPE: PRT
<213> ORGANISM: Macaca fascicularis

<400> SEQUENCE: 51

Val Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240
```

-continued

```
Leu Phe Ala Leu Cys Trp Leu Pro Leu His Ile Ile Asn Cys Phe Thr
                245                 250                 255

Phe Phe Cys Pro Asp Cys Asn His Ala Pro Leu Trp Leu Met Tyr Leu
            260                 265                 270

Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
    290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Thr Gln Glu Ser Gln Gly Asn Thr Ser Leu Pro Asp Val Glu
    370                 375                 380

Leu Leu Ser His Glu Leu Lys Gly Val Cys Pro Glu Pro Pro Gly Leu
385                 390                 395                 400

Asp Asp Pro Leu Ala Gln Gly Gly Ala Gly Val Ser
                405                 410
```